(12) United States Patent
Ray et al.

(10) Patent No.: US 10,987,036 B2
(45) Date of Patent: Apr. 27, 2021

(54) SYSTEMS, DEVICES, AND METHODS FOR PERFORMING TRANS-ABDOMINAL FETAL OXIMETRY AND/OR TRANS-ABDOMINAL FETAL PULSE OXIMETRY USING DIFFUSE OPTICAL TOMOGRAPHY

(71) Applicant: Raydiant Oximetry, Inc., San Ramon, CA (US)

(72) Inventors: Neil Padharia Ray, Sacramento, CA (US); Mark Andrew Rosen, Piedmont, CA (US); Adam Jacobs, Hollis, NH (US); Denise Zarins, Saratoga, CA (US); Kenneth Holt, Cacadero, CA (US); Jana M Kainerstorfer, Pittsburg, PA (US); David Boas, Boston, MA (US)

(73) Assignee: RAYDIANT OXIMETRY, INC., San Ramon, CA (US)

( * ) Notice: Subject to any disclaimer, the term of this patent is extended or adjusted under 35 U.S.C. 154(b) by 0 days.

(21) Appl. No.: 16/912,627

(22) Filed: Jun. 25, 2020

(65) Prior Publication Data
US 2020/0323467 A1    Oct. 15, 2020

Related U.S. Application Data

(63) Continuation of application No. PCT/US2019/040639, filed on Jul. 3, 2019.
(Continued)

(51) Int. Cl.
*A61B 5/1464* (2006.01)
*A61B 5/024* (2006.01)
*A61B 5/1455* (2006.01)

(52) U.S. Cl.
CPC ........ *A61B 5/1464* (2013.01); *A61B 5/02411* (2013.01); *A61B 5/14551* (2013.01); *A61B 2503/02* (2013.01)

(58) Field of Classification Search
CPC . A61B 5/1455; A61B 5/14551; A61B 5/1464; A61B 5/02411; A61B 5/0011;
(Continued)

(56) References Cited

U.S. PATENT DOCUMENTS

| 4,911,167 A | 3/1990 | Corenman et al. |
| 5,348,002 A | 9/1994 | Caro |

(Continued)

FOREIGN PATENT DOCUMENTS

| CN | 103381094 A | 11/2013 |
| EP | 1054620 B1 | 1/2010 |

(Continued)

OTHER PUBLICATIONS

Delpy, et al., "Quantification in tissue near-infrared spectroscopy," Phil. Trans. R. Soc. Lond. B, 352: 649-659, 1997.
(Continued)

*Primary Examiner* — Chu Chuan Liu
(74) *Attorney, Agent, or Firm* — Resonance IP Law, PC

(57) ABSTRACT

Fetal tissue oxygenation may be performed transabdominally by, for example, receiving a plurality of detected electronic signals that correspond to light emitted from a pregnant mammal's abdomen and a fetus contained therein that has been detected by the detector and converted into the detected electronic signal. An indication of a depth of the fetus within the pregnant mammal's abdomen may be received and a portion of the detected electronic signals that correspond to light that was incident upon the fetus may be isolated responsively to the indication of the depth of the fetus using, for example, time of flight of photons that
(Continued)

correspond to the detected electronic signals. A fetal tissue oxygen saturation level may then be determined using the isolated portion of the detected electronic signals that correspond to light that was incident upon the fetus.

19 Claims, 27 Drawing Sheets

Related U.S. Application Data

(60) Provisional application No. 62/694,122, filed on Jul. 5, 2018, provisional application No. 62/694,130, filed on Jul. 5, 2018, provisional application No. 62/694,135, filed on Jul. 5, 2018, provisional application No. 62/694,146, filed on Jul. 5, 2018, provisional application No. 62/694,170, filed on Jul. 5, 2018, provisional application No. 62/694,184, filed on Jul. 5, 2018, provisional application No. 62/694,199, filed on Jul. 5, 2018, provisional application No. 62/694,261, filed on Jul. 5, 2018.

(58) Field of Classification Search
CPC ............ A61B 5/14542; A61B 5/14552; A61B 5/14553; A61B 5/02416; A61B 5/02433; A61B 5/02444
See application file for complete search history.

(56) References Cited

U.S. PATENT DOCUMENTS

| | | | |
|---|---|---|---|
| 5,524,617 A * | 6/1996 | Mannheimer | A61B 5/14551 356/41 |
| 5,807,271 A | 9/1998 | Tayebi et al. | |
| 5,835,558 A | 11/1998 | Maschke | |
| 6,453,183 B1 * | 9/2002 | Walker | A61B 5/14553 600/322 |
| 6,498,942 B1 | 12/2002 | Esenaliev et al. | |
| 6,690,958 B1 | 2/2004 | Walker et al. | |
| 7,047,055 B2 | 5/2006 | Boas et al. | |
| 7,469,158 B2 | 12/2008 | Cutler et al. | |
| 7,515,948 B1 | 4/2009 | Balberg et al. | |
| 8,275,436 B2 | 9/2012 | Wang et al. | |
| 8,644,900 B2 | 2/2014 | Balberg et al. | |
| 9,757,058 B2 | 9/2017 | Ray | |
| 9,968,286 B2 | 5/2018 | Ray | |
| 10,362,974 B2 | 7/2019 | Ray | |
| 2003/0073910 A1 | 4/2003 | Chance | |
| 2004/0116789 A1 | 6/2004 | Boas et al. | |
| 2006/0122475 A1 | 6/2006 | Balberg et al. | |
| 2008/0208009 A1 | 8/2008 | Shklarski | |
| 2009/0281402 A1 | 11/2009 | Chance | |
| 2010/0081901 A1 | 4/2010 | Buice et al. | |
| 2011/0218413 A1 | 9/2011 | Wang et al. | |
| 2012/0190946 A1 | 7/2012 | Bemreuter | |
| 2013/0338460 A1 | 12/2013 | He et al. | |
| 2015/0099950 A1 | 4/2015 | Al-Ali et al. | |
| 2016/0015304 A1 | 1/2016 | Esenaliev et al. | |
| 2016/0128594 A1 | 5/2016 | Amir et al. | |
| 2017/0188920 A1 | 7/2017 | Ray | |
| 2018/0070871 A1 | 3/2018 | Ray | |
| 2019/0343437 A1 | 11/2019 | Ray | |

FOREIGN PATENT DOCUMENTS

| | | |
|---|---|---|
| WO | 2004086966 A1 | 10/2004 |
| WO | 2009032168 A1 | 3/2009 |
| WO | 2018094391 A2 | 7/2018 |

OTHER PUBLICATIONS

Dildy et al., "Intrapartum fetal pulse oximetry: Past, present, and future," American Journal of Obstetrics & Gynecology, 175(1): 1-9, Jul. 1996.

Dildy, "Fetal Pulse Oximetry," Clinical Obstetrics and Gynecology, 54(1): 66-73, Mar. 2011.

Dildy, et al., "Current status of the multicenter randomized clinical trial on fetal oxygen saturation monitoring in the United States," European Journal of Obstetrics & Gynecology and Reproductive Biology, 72 Suppl. 1, pp. S43-S50, 1997.

Dildy, et al., "Intrapartum fetal pulse oximetry: Fetal oxygen saturation trends during labor and relation to delivery outcome," Am. J. Obstet. Gynecol., 171(3): 679-684, Sep. 1994.

Dildy, et al., "Management of prolonged decelerations," OBG Management, 7 pgs., Nov. 2006.

Dildy, et al., "Preliminary Experience with Intrapartum Fetal Pulse Oximetry in Humans," Obstetrics and Gynecology, 81(4): 630-635, Apr. 1993.

Diniz, In Adaptive Filtering Algorithms and Practical Implemetation, Springer, Third Edition, p. 636, 2008.

Dong, et al., "Simultaneously Extracting Multiple Parameters Via Fitting One Single Autocorrelation Function Curve in Diffuse Correlation Spectroscopy," IEEE Transactions on Biomedical Engineering, 60(2): 361-368, Feb. 2013.

Donlon, et al., "MEG Visual Stimuli Software", MEG Setup Documentation, 3 pages.

Durduran, et al., "Diffuse correlation spectroscopy for non-invasive, micro-vascular cerebral bloodflow measurement," NeuroImage, 85: 51-63, 2014.

Durduran, et al., "Diffuse optics for tissue monitoring and tomography," Reports on Progress in Physics, 73: pp. 44, 2010.

East et al., "Fetal oxygen saturation and uterine contractions during labor," Am J Perinatol, 15(6): 345-349, Jun. 1998 (Abstract only).

East, et al., "A cost-effectiveness analysis of the intrapartum fetal pulse oximetry multicentre randomised controlled trial (the FOREMOST trial)," BJOG An International Journal of Obstetrics and Gynaecology, pp. 1080-1087, 2006.

East, et al., "Fetal oxygen saturation during maternal bearing down efforts in the second stage of labor," Am J. Perinatol, 15(2): 121-124, 1998 (Abstract only).

East, et al., "Fetal Oxygen Saturation Monitoring in Labour: An Analysis of 118 Cases," Aust. and NZ Journal of Obstetrics and Gynaecology, 37(4): 397-401, 1997.

East, et al., "Fetal pulse oximetry for fetal assessment in labour (Review)," The Cochrane Collaboration, pp. 1-76, 2014.

East, et al., "Intrapartum fetal scalp lactate sampling for fetal assessment in the presence of a non-reassuring fetal-heart rate trace (Review)," The Cochrane Database of Systematic Reviews 2015, Issue 5. Art. No. CD006174., pp. 1 to 39, 2015.

East, et al., "Intrapartum Oximetry of the Fetus," Anesthesia & Analgesia, 105(6): S59-S65, Dec. 2007.

East, et al., "The effect of intrapartum fetal pulse oximetry, in thepresence of a nonreassuring fetal heart rate pattern, onoperative delivery rates: A multicenter, randomized,controlled trial (the FOREMOST trial)," American Journal of Obstetrics and Gynecology, 194: 606.e1-606.e16, 2006.

East, et al., "Update on intrapartum fetal pulse oximetry," Aust NZ J Obstet Gynaecol, 42(2): 119-124, 2002.

Eden et al., "Reengineering Electronic Fetal Monitoring Interpretation: Using the Fetal Reserve Index to Anticipate the Need for Emergent Operative Delivery," Reproductive Sciences, 25(4): 487-497, 2018.

Eden, et al., "The "Fetal Reserve Index": Re-Engineering the Interpretation and Responses to Fetal Heart Rate Patterns," Fetal Diagnosis and Therapy, 43: 90-104, Jun. 2017.

Emberson, et al., "Isolating the effects of surface vasculature in infant neuroimaging using short-distance optical channels: a combination of local and globaleffects," Neurophotonics, 3(3); 031406-1-031406-12, Jul.-Sep. 2016.

Eunson, "The long-term health, social, and financial burden ofhypoxic-ischaemic encephalopathy," Developmental Medicine & Child Neurology, 57 (Suppl. 3): 48-50, 2015.

Evans, et al., "Re-engineering the interpretation of electronicfetal monitoring to identify reversible risk forcerebral palsy: a case control series," The Journal of Maternal-Fetal & Neonatal Medicine, pp. 1-10, 2018.

(56) References Cited

OTHER PUBLICATIONS

Fabbri et al., "Optical measurements of absorption changes intwo-layered diffusive media," Physics in Medicine & Biology, 49: 1183-1201, Mar. 18, 2004.
Fantini, et al., "Frequency-domain multichannel optical detector for nonivasive tissue spectroscopy and oximetry," Optical Engineering, 34(1): 32-42, Jan. 1995.
Fantini, et al., "Frequency-domain techniques for tissue spectroscopy and imaging", In Handbook of Optical Biomedical Diagnostics, Second Edition, vol. 1: Light Tissue Interaction, Chapter 7, pp. 1-52, 2002.
Farrell, et al., "Influence of layered tissue architecture on estimates of tissue optical properties obtained from spatially resolved diffuse reflectometry," Applied Optics, 37(10): 1958-1972, Apr. 1, 1998.
Farzam, "Hybrid diffuse optics for monitoring of tissue hemodynamics with applications in oncology," Doctoral Thesis in Photonics, Institute of Photonic Sciences, pp. 1-240, Jul. 2014.
Fatemi, et al., "Hypoxic Ischemic Encephalopathy in the Term Infant," Author manuscript; available in PMC, Dec. 1, 2010, p. 23, 2009.
Figures of Two-minute tracing showing fetal heart rate, and Pulse oximetry tracing from 25-week gestation fetus undergoing open congenital diaphragmatic hernia repair, Anesthesia for Fetal Procedures and Surgery, pp. 280-281.
Firbank, et al., "An investigation of light transport through scattering bodies with non-scattering regions," Phys. Med. Biol., 41: 767-783, 1996.
Fong, et al., "Recovering the Fetal Signal in Transabdominal Fetal Pulse Oximetry," Smart Health, 9-10: 23-26, Jul. 9, 2018.
Fong, et al., "Transabdominal Fetal Blood Oximetry," Website of the University of California, DAVIS, Office of Research, http://research.ucdavis.edu/u/s/ia, pp. 1, 2017.
Fong, et al., "Transabdominal Fetal Pulse Oximetry: The Case of Fetal Signal Optimization," 2017 IEEE 19th International Conference on e-Health Networking, Applications and Services (Healthcom), pp. 1-6, 2017.
Fong, "Recovering the Fetal Signal in Transabdominal Fetal Pulse Oximetry," Article appearing in unedited Manuscript Smart Health, https://doi.org/10.1016/j.smhl.2018.07.011, p. 13, 2017.
Franceschini, et al., "Assessment of Infant Brain Development with Frequency-Domain Near-Infrared Spectroscopy," Pediatr Res., 61(5): 546-551, 2007.
Franceschini, et al., "Influence of a superficial layer in the quantitative spectroscopic study of strongly scattering media," Applied Optics, 37(31): 7447-7458, Nov. 1, 1998.
Gagnon, et al., "Further improvement in reducing superficial contamination in NIRS using doubleshort separation measurements," NeuroImage, 85: 127-135, 2014.
Gagnon, et al., "Short separation channel location impacts the performance of short channel regression in NIRS," NeuroImage, 59: 2518-2528, 2012.
Ganesan et al., "Diffuse optical spectroscopic imaging of subcutaneous adipose tissue metabolic changes during weight loss," Int J Obes (Lond). Aug. 2016; 40(8). Author Manuscript available in PMC Oct. 22, 2016., pp. 1292-1300, Oct. 2016.
Gardner, et al., "Enhanced Umbilical Blood Flow During Acute HypoxemiaAfter Chronic Umbilical Cord Compression, A Role for Nitric Oxide," Basic Science Reports in Circulation, pp. 331-335, Jun. 30, 2003.
Gardosi, et al., "Adaptation of pulse oximetry for fetal monitoring during labour," The Lancet, 337: 1265-1267, May 25, 1991.
Gardosi, et al., "Continuous Intrapartum Monitoring Offectal Oxygen Saturation," The Lancet, Sep. 16, 1989, pp. 692-693.
Garite, et al., "Transactions of the Twentieth Annual Meeting of the Society for Maternal-Fetal Medicine—Continued," American Journal of Obstetrics and Gynecology, 183(5): 1049-1058, Nov. 2000.
Ghiasi, et al., "Transabdominal Fetal Oximetry, Project conducted at the Laboratory for Embedded and Programmable Systems," (LEPS), pp. 1-4.
Giordano, "New ANSI guidelines remind users to take stock of industrial laser protections," Laser Focus World, 50(10):41-43+47•Oct. 2014.
Goodlin, "Preliminary experience with intrapartum fetal pulse oximetry in humans," Obstetrics and Gynecology, 82(2): 314-315, Jul. 31, 1993.
International Search Report and the Written Opinion of the International Searching Authority for International Application No. PCT/US19/40639 dated Nov. 12, 2019.
Subramaniam, "An IR Muscle Contraction Sensor", Cornell University, student project (last modified Jun. 10, 2014), retrieved from: https://people.ece.cornell.edu/land/courses/eceprojectsland/STUDENTPROJ/2013to2014/ras578/Writeup/An%20IR%20Muscle%20Contraction%20Sensor.html, 6 pgs., Feb. 2017.
Sutin, et al., "Time-domain diffuse correlation spectroscopy," Optica, vol. 3, Issue 9, pp. 1006-1013, Sep. 2016.
Severinghaus, et al., "History of Blood Gas Analysis. VII. Pulse Oximetry," Journal of Clinical Monitoring, 3(2): 135-138, Apr. 1987.
Shang, et al., "Portable optical tissue flow oximeter based on diffuse correlation spectroscopy," Optics Letters, 34(22): 3556-3558, Nov. 15, 2009.
Siristatidis, et al., "Alterations in Doppler velocimetry indices of the umbilical artery during fetal hypoxia in labor, in relation to cardiotocography and fetal pulse oximetry findings," Arch Gynecol Obstet , 272: 191-195, 2005.
Siristatidis, et al., "Evaluation of fetal intrapartum hypoxia by middle cerebral and umbilical artery Doppler velocimetry with simultaneous cardiotocography and pulse oximetry," Arch Gynecol Obstet, 270: 265-270, 2004.
Siristatidis, et al., "Intrapartum Surveillance of IUGR Fetuses with Cardiotocography and Fetal Pulse Oximetry," Biology of the Neonate, 83: 162-165, 2003.
Spector-Bagdady, et al., "Clinician Self-Interestand the Case of Electronic Fetal Monitoring," Hastings Center Report, pp. 16-24, Nov.-Dec. 2017.
Spencer, et al., "MASS Spectrometer System for Continuous Skin-Surface and Intravascular Blood Gas Measurement of Maternal-Fetal Respiration in Labour," Journal of Biomedical Engineering , 9: 161-168, Apr. 1987.
Spong, et al., "Preventing the First Cesarean Delivery: Summary of a Joint Eunice Kennedy Shriver National Institute of Child Health and Human Development, Society for Maternal-Fetal Medicine, and American College of Obstetricians and Gynecologists Workshop," American Journal of Obstetrics and Gynecology, 120(5): 1181-1193, 2012.
Steinbrink, et al., "Illuminating the BOLD signal: combined fMRI—fNIRS studies," Magnetic Resonance Imaging, 24: 495-505, 2006.
Stipcevic et al., "Characterization of a novel avalanche photodiode for single photon detection in VIS-NIR range," Optics Express, 18(16): 17448-17459, Jul. 30, 2010.
Strangman, et al., "Factors affecting the accuracy of near-infrared spectroscopy concentration calculations for focal changes in oxygenation parameters," NeuroImage, 18: 865-879, 2003.
Tamborini, et al., "Development and characterization of a multi distance and multi wave length diffuse correlation spectroscopy system," Neurophoton, 5(1): 011015-1-011015-10, Jan.-Mar. 2018.
Themelis, et al., "Near-infrared spectroscopy measurement of the pulsatilecomponent of cerebral blood flow and volume from arterial oscillations," Journal of Biomedical Optics, 21(1), pp. 1-15, 2007.
Tomich, "Fetal heart rate monitoring," Power Point—Department of Obstetrics and Gynecology, University of Nebraska College of Medicine, (uploaded Jul. 30, 2014) 69 pages.
Torbenson, et al., "Intrapartum factors associated with neonatal hypoxic ischemic encephalopathy: a case-controlled study," BMC Pregnancy and Childbirth, 17(415): 1-7 , 2017.
Townsend, et al, "Pulse Oximetry," Medical Electronics, Michaelmas Term, 2001.
Truven Health Analytics, The Cost of Having a Baby in the United States—Executive Summary, Truven Health Analytics Marketscan Study, pp. 5, Jan. 2013.

(56) References Cited

OTHER PUBLICATIONS

Truven Health Analytics, The cost of having a baby in the United States, Truven Health Analytics Marketscan® Study, pp. 1 to 84, 2013.
Tu, et al., "An Analytical Model for Optimization of Frequency-domain System," Bioengineering Conference, 2002. Proceedings of the IEEE 28th Annual Northeast, pp. 79-80, 2002.
Uchida, et al., "Reevaluation of intrapartum fetal monitoring using fetaloximetry: A review," The Journal of Obstetrics and Gynaecology Research, pp. 1-8, 2018.
Ultman, et al., "Differential Pathlength Factor for Diffuse Photon Scattering Through Tissue by a Pulse-Response Method," 107: 73-82, 1991.
Valverde, et al., "Effectiveness of pulse oximetry versus fetal electrocardiography for the intrapartum evaluation of non reassuring fetal heart rate," European Journal of Obstetric and Gynecology and Reproductive Biology, 159: 333-337, 2011.
Van't Hooft, In "Improving evaluation of obstetric interventions," pp. 1-243, 2016.
Verkruysse, et al., "Calibration of Contactless Pulse Oximetry," Anathesia & Analgesia, 124(1): 136-145, Jan. 2017.
Vidaeff, et al., "Fetal pulse oximetry: 8 vital questions," OBG Management, pp. 28-44, Mar. 2004.
Vintzileos, et al., "Transabdominal fetal pulse oximetry with near-infrared spectroscopy," American Journal of Obstetrics and Gynecology, 192: 129-133, 2005.
Vishnoi et al., "Photon migration through fetal head in utero using continuous wave, near-infrared spectroscopy: development and evaluation of experimental and numerical models", J. Biomedical Optics 5(2): 163-172, Apr. 2000.
Weyrich, et al., "Development of a Phantom to Modulate the Maternal and Fetal Pulse Curve for Pulse Oximetry Measurements," Biomed Tech 57 (Suppl. 1): 803-806, 2012.
Willmann, et al., "Small-volume frequency-domain oximetry: phantom experiments and first in vivo results," Journal of Biomedical Optics, 8(4): 618-628, Oct. 2003.
Wolfberg, "The Future of Fetal Monitoring," Reviews in Obstetrics & Gynecology, 5(3/4): e132-e136, 2012.
Woo, et al., "Achieving higher-value obstetrical care," American Journal of Obstetrics & Gynecology, pp. 250-255 and 250.e1-250.e8, Mar. 2017.
XP The Xperts in Power, 400-2500 Watts fleX, 400-2500 Watts fleXPower Series, Product information sheet, xppower.com, pp. 1 to 10, Jan. 5, 2016.
Yamaleyeva, et al., "Photoacoustic imaging for in vivo quantification of placental oxygenation in mice," The FASEB Journal, 31(12): 5520-5529, 2017.
Yan, et al., "Reduction of motion artifact in pulse oximetry by smoothed pseudo Wigner-Ville distribution," Journal of NeuroEngineering and Rehabilitation, 2(3), pp. 1-9, Mar. 1, 2005.
Yousefi, et al., "Adaptive Cancellation of Motion Artifact in Wearable Biosensors," 34th Annual International Conference of the IEEE EMBS, San Diego, California USA, Aug. 28-Sep. 1, 2012.
Yuan, et al., "Motion Artefact Minimisation from Photoplethysmography based Non-invasive Hemoglobin Sensor by the Envelope Method," Measurements, 115, pp. 1-18, Feb. 2018.
Zhang et al., "Adaptive filtering for global interference cancellation andreal-time recovery of evoked brain activity: a Monte Carlo simulation study," Journal of Biomedical Optics, 12(4): 044014-1-044014-12, Jul./Aug. 2007.
Zhao, et al., "In vivo determination of the optical propertiesof infant brain using frequency-domain near-infrared spectroscopy," Journal of Biomedical Optics, 10(2): 024028-1-024028-7, Mar./Apr. 2005.
Zhao, et al., "Quantitative real-time pulse oximetry with ultrafast frequency frequency-domain diffuse optics and deep neural network processing," Biomedical Optics Express, 9(12): 5997-6008, 2018.
Zijistra, et al., "Absorption Spectra of Human Fetal and Adult Oxyhemoglobin, De-Oxyhemoglobin, Carboxyhemoglobin, and Methemoglobin," Clinical Chemistry, 37(9): 1633-1638, 1991.
Zourabian, et al., "Trans-abdominal monitoring of fetal arterial blood oxygenation using pulse oximetry," Journal of Biomedical Optics, 5(4): 391-405, Oct. 2000.
McNamara, et al., "Continuous intrapartum pH, pO2, pCO2,and SpO2 monitoring," Obstet Gynecol Clin North Am, 26(4): 671-693, Dec. 1999 (Abstract only).
Mesquita, et al., Direct measurement of tissue blood flow andmetabolism with diffuse optics,: Philosophical Transactions of The Royal Society A, 369: 4390-4403, 2011.
Miller, "Raydiant Oximetry: Provides Crucial Comfort for New Mothers," MedTech Strategist, vol. 5, No. 4—Mar. 27, 2018, 2 pages.
Molavi, et al., "Motion Artifact Removal from Muscle NIR Spectroscopy Measurements," Canadian Conference on Electrical and Computer Engineering, pp. 1-5, May 2010.
Mourant, et al., "Mechanisms of light scattering from biologicalcells relevant to noninvasive optical-tissue diagnostics," Applied Optics, 37(15): 3586-3593, Jun. 1, 1998.
Nasiriavanaki, et al., "High-resolution photoacoustic tomography of resting-state functional connectivity in the mouse brain," PNAS, 111(1): 21-26, Jan. 7, 2014.
Nelson, et al., "Electronic fetal monitoring, cerebralpalsy, and caesarean section: assumptions versus evidence," BMJ, 355: pp. 1-3, Dec. 1, 2016.
Nioka, et al., "Fetal transabdominal pulse oximeter studies using a hypoxic sheep model," The Journal of Maternal-Fetal and Neonatal Medicine, 17(6): 393-399, Jun. 2005.
Nitzan, et al., "Calibration-Free Pulse Oximetry Based on Two Wavelengths in the Infrared—A Preliminary Study," Sensors 2014, 14: 7420-7434, Apr. 23, 2014.
Nonnenmacher, et al., "Predictive value of pulse oximetry for the development of fetal acidosis," J. Perinat. Med, 38: 83-86, 2010.
Noren, et al., "Reduced prevalence of metabolic acidosis at birth: an analysis of established STAN usage in the total population of deliveries in a Swedish district hospital," American Journal of Obstetrics & Gynecology, 202: 546.e1-546.e7, Jun. 2010.
Novak et al., "Perinatal Brain Injury Mechanisms, Prevention, and Outcomes," Clin Pernatol, 45: 357-375, 2018.
OBG Project, "Which Fetal Heart Monitoring Parameters Best Predict Fetal Acidemia?," https://www.obgproject.com/category/grandrounds/) pp. 1-2, date unknown.
Office Action dated Feb. 1, 2018, from the Taiwan Intellectual Property Office, for Taiwan Patent Application No. 105143848, 17 pages.
Olutoye, et al., "Food and Drug Administration warning on anesthesia and brain development: implications for obstetric and fetal surgery," American Journal of Obstetrics & Gynecology, pp. 98-102, Jan. 2018.
Patient Safety Movement Foundation, "Actionable Patient Safety Solution (APSS) #11C: Reducing Unnecessary C-Sections," 2018 Patient Safety Movement Foundation, pp. 1-8, Aug. 15, 2018.
PCT/US2018/068042 International Search Report and Written Opinion, dated Apr. 26, 2019, 16 pages.
PCT/US2018/068049 International Search Report and Written Opinion, dated Apr. 26, 2019, 20 pages.
Peat, et al., "Continuous intrapartum measurement of fetal oxygen saturation," The Lancet, Jul. 23, 1988, pp. 213.
Peebles, et al., "Effect of oxytocin on fetal brain oxgenation during labour," The Lancet, 338: 254-255, Jul. 27, 1991.
Peek, et al., "Fetal Pulse Oximetry and Cesarean Delivery," The New England Journal of Medicine, 356: 1377-1378, Mar. 29, 2007.
Pereira, et al., "Recognition of chronic hypoxia and pre-existing foetal injury on the cardiotocograph (CTG): Urgent need to think beyond the guidelines," Porto Biomedical Journal, 2(4): 124-129, 2017.
Peters, et al., "Beat-to-beat detection of fetal heart rate: Doppler ultrasound cardiotocography compared to direct ECG cardiotocography in time and frequency domain," Physiological Measurement, 25: 585-593, 2004.
Phelan et al., "Fetal Heart Rate Observations in the Brain-Damaged Infant," Seminars in Perinatology, 24(3): 221-229, Jun. 2000.
Philips proprietary camera based monitoring technology is first in the world to measure absolute arterial blood oxygenation (SpO2)

(56) References Cited

OTHER PUBLICATIONS levels without ever touching the patient, Jun. 6, 2016, 4 pages (https://www.usa.philips.com/a-w/about/news/archive/standard/news/press/2016/20160606-philips-proprietary-camera-based-monitoring-technology-is-first-in-the-world-to-measure-absolute-arterial-blood-oxygenation-levels-without-ever-touching-the-patient.html) Jun. 6, 2016.

Pifferi, et al., "Real-time method for fitting time-resolved relectance and transmittance measurements with a Monte Carlo model," Applied Optics, 37(13): 2774-2776, May 1, 1998.

Porreco, et al., "Dystocia in nulliparous patients monitored with fetal pulse oximetry," American Journal of Obstetrics and Gynecology, 190: 113-117, 2004.

Ragozzino, et al., "Average Fetal Depth in Utero: Data for Estimation of Fetal Absorbed Radiation Dose," Radiology, 158(2): 513-515, 1986.

Ramanujam, et al., "Antepartum, Transabdominal Near Infrared Spectroscopy: Feasibility of Measuring Photon Migration Through the Fetal Head in Utero," The Journal of Maternal-Fetal Medicine, 8: 275-288, 1999.

Ramanujam, et al., "Photon migration through fetal head in utero using continuous wave, near infrared spectroscopy," Journal of Biomedical Optics, 5(2): 173-184, Apr. 2000.

Rei, et al., "Neurological damage arising from intrapartum hypoxia/acidosis," Best Practice & Research Clinical Obstetrics and Gynaecolology, 30: 79-86, 2016.

Ren, et al., "Quasi-simultaneous multimodal imaging of cutaneous tissue oxygenation and perfusion," Journal of Biomedical Optics, 20(12): 121307-1-121307-10, Dec. 2015.

Reuss, "Factors Influencing Fetal Pulse Oximetry Performance," Journal of Clinical Monitoring and Computing, 18: 13-24, 2004.

Reuss, "Multilayer Modeling of Reflectance Pulse Oximetry," IEEE Transactions on Biomedical Engineering, 52(2): 153-159, Feb. 2005.

Reuss, et al., "The pulse in reflectance pulse oximetry : modeling and experimental studies," Journal of Clinical Monitoring and Computing , 18: 289-299, 2004.

Rivolta, et al., "Acceleration and Deceleration Capacity of Fetal Heart Rate in an In-Vivo Sheep Model," PLOS One, 98(8): 1-10, Aug. 2014.

Roche-Labarbe, et al., "Noninvasive Optical Measures of CBV, StO2, CBF Index, and rCMRO2in Human Premature Neonates' Brains in the First Six Weeks of Life," Human Brain Mapping , 31: 341-352, 2010.

Roemer, et al., "Sensitivity, specificity, receiver—operating characteristic (ROC) curves and likelihood ratios for electronic foetal heart rate monitoring using new evaluation techniques," Z Geburtshilfe Neonatol, 214(3): 108-118, Jun. 2010.

Ross, "Labor and Fetal Heart Rate Decelerations: Relation to Fetal Metabolic Acidosis," Clinical Obstetrics and Gynecology, 54(1): 74-82, 2011.

Roth, et al, "Unequal Motherhood: Racial-Ethnic and Socioeconomic Disparities in Cesarean Sections in the United States," Social Problems, 59(2): 207-227, May 2012.

Saager, et al., "Direct characterization and removal of interfering absorption trends in two-layer turbid media," J. Opt. Soc. Am. A, 22(8): 1874-1882, Sep. 2005.

Sabiani, et al., "Intra- and interobserver agreement amongobstetric experts in court regarding the reviewof abnormal fetal heart rate tracings andobstetrical management," American Journal of Obstetrics & Gynecology, 213(6): 856. e1-856.e8, Dec. 2015.

Saccone, et al., "Electrocardiogram ST Analysis During Labor A Systematic Review and Meta-analysis of Randomized Controlled Trials," Obstetrics & Gynecology, 127(1): 127-135, Jan. 2016.

Salamalekis, et al., "Computerised intrapartum diagnosis of fetal hypoxia based onfetal heart rate monitoring and fetal pulse oximetry recordingsutilising wavelet analysis and neural networks," BJOG: an International Journal of Obstetrics and Gynaecology, 109: 1137-1142, Oct. 2002.

Salamalekis, et al., "Fetal pulse oximetry and wavelet analysis of the fetal heart rate in the evaluation of abnormal cardiotocography tracings," J. Obstet. Gynaecol. Res., 32(2): 135-139, Apr. 2006.

Sartwelle, et al., "A half century of electronic fetalmonitoring and bioethics: silence speakslouder than words," Maternal Health, Neonatology, and Perinatology, 3:(21): 1-8, 2017.

Sartwelle, et al., "The Ethics of Teaching Physicians Electronic Fetal Monitoring: And Now for the Rest of the Story," 3: e42-e-47, 2017.

Sassaroli, et al., "Comment on the modified Beer-Lambert law for scattering media," Physics in Medicine & Biology, vol. 49, No. 14, pub'd Jul. 5, 2004 (Phys. Med. Biol. 49 (2004) N255-N257).

Schiermeier, et al., "Sensitivity and specificity of intrapartum computerised FIGO criteria for cardiotocography and fetal scalp pH during labour: multicentre, observational study," BJOG An International Journal of Obstetrics and Gynaecology, pp. 1557-1563, Aug. 26, 2008.

Schweiger, et al., "Near-infrared imaging: photon measurement density functions," Proc. SPIE, 2389: 366-377, May 30, 1995.

Seelbach-Göbel, et al., "The prediction of fetal acidosis by means of intrapartum fetalpulse oximetry," American Journal of Obstetrics and Gynecology, 180(1): 73-81, Jan. 1999.

"Anesthesia for Fetal Procedures and Surgery," pp. 280-281.

"Assessing the Photobiological Safety of LEDs," pp. 1-8, 2012.

"Corometrics™ 250 Series Monitor Operator's Manual", GE Healthcare, Revision E (Apr. 28, 2009), 258 pgs.

"Fetal Pulse Oximetry System Clinical Use Guide", OxiFirst, Nellcor (2003), 60 pgs.

"Narrow beam LED in Dragon Dome package (850nm)", OSRAM Opto Semicondutors (Mar. 10, 2014), Version 1.3, SFH 4783, pp. 1-12.

"OSRAM Opto Semiconductors GF CSHPM1.24-3S4S-1", Mouser Electronics (accessed Dec. 2016), 2 pgs.

Aaronson, et al., "Android-Based Tocodynamometer and Fetal Heart Rate Monitor", Tocotronics (2013), 21 pgs.

Ahearne, et al., "Short and long term prognosis in perinatal asphyxia: An update," World Journal of Clinical Pediatrics, 5(1): 67-74, Feb. 8, 2016.

Aldrich, et al., "Late fetal heart decelerations and changes in cerebral oxygenation during the first stage of labour," British Journal of Obstetrics and Gynaecology, 102: 9-13, Jan. 1995.

Alfirevic, et al., "Continuous cardiotocography (CTG) as a form of electronicfetal monitoring (EFM) for fetal assessment during labour (Review)," Cochrane Database of Systematic Reviews 2017, Issue 2. Art. No. CD006066, pp. 1 to 56, 2017.

Amer, et al., "Xenon Combined With Hypothermia in Perinatal Hypoxic-Ischemic Encephalopathy: A Noble Gas, a Noble Mission," Pediatric Neurology, 84: 5-10, Jul. 2018.

Angelo, et al., "Review of structured light in diffuse optical imaging," Journal of Biomedical Optics 24(7), 071602 (Jul. 2019), 20 pages.

Arridge, Inverse Problems in Optical Tomography,: INI Cambridge, pp. 1-74, Aug. 24, 2011.

Arridge, "Optical tomography in medical imaging," Inverse Problems, 15: R41-R93, 1999.

Arridge, et al., "The theoretical basis for the determination of optical path lengths in tissue: temporal and frequency analysis," Physics in Medicine & Biology, 37(7): 1531-1560, 1992.

Ayres-De-Campos, "Electronic fetal monitoring orcardiotocography, 50 years later: what's in a name?," American Journal of Obstetrics & Gynecology, 218(6): 545-546, Jun. 2018.

Bansal; et al., "Wearable Organic Optoelectronic Sensors for Medicine", Advanced Materials (2014), 7 pgs.

Barry, et al., "The Pregnant Sheep as a Model for Human Pregnancy," Theriogenology, 69(1): 55-67, Jan. 1, 2008.

Bauer, et al., "Quantitative photoacoustic imaging:correcting for heterogeneous light fluence distributions using diffuse optical tomography," Journal of Biomedical Optics, 16(9): 096016-1-096016-7, Sep. 2011.

Belfort, et al., "A Randomized Trial of Intrapartum Fetal ECG ST-Segment Analysis," The New England Journal of Medicine, 373(7): 632-641, Aug. 13, 2015.

(56) References Cited

OTHER PUBLICATIONS

Bennet, et al., "The Cerebral Hemodynamic Response to Asphyxia and Hypoxia in the Near-term Fetal Sheep as Measured by Near Infrared Spectroscopy," Pediatric Research, 44: 951-957, Dec. 1, 1998.
Bennet, et al., "The Fetal Heart Rate Response to Hypoxia: Insights from Animal Models," Clin Perinatol, 36: 655-672, 2009.
Bevilacqua, et al., "In vivo local determination of tissue optical properties: applications to human brain," Applied Optics, 38(22): 4939-4950, 1999.
Bloom, et al., "Fetal Pulse Oximetry and Cesarean Delivery," The New England Journal of Medicine, 355: 2195-2202, Nov. 23, 2006.
Bloom, et al., "Fetal Pulse Oximetry: Duration of Desaturation and Intrapartum Outcome," Journal of Obstetrics and Gynecology, 93(6): 1036-1040, Jun. 1999.
Bloom, et al., "What We Have Learned About Intrapartum Fetal Monitoring Trials in the MFMU Network," Author Manuscript, Semin Perinatol, 40(5): 307-317, Aug. 2016.
Boas et al., "Scattering and Imaging with Diffusing Temporal Fields correlation," Physical Review Letters, vol. 75, No. 9, Aug. 28, 1995, pp. 1855-1859.
Boas, et al., "Diffuse optical imaging of brain activation: approaches to optimizing image sensitivity, resolution, and accuracy," NeuroImage, 23: S275-S288, 2004.
Boas, et al., "Spatially varying dynamical properties of turbidmedia probed withdiffusing temporal light correlation," J. Opt. Soc. Am., 14(1): 192-215, Jan. 1997.
Bottrich, et al., "Signal Separation for Transabdominal Non-invasive Fetal Pulse Oximetry using Comb Filters," Conf Proc IEEE Eng Med Biol Soc, pp. 5870-5873, 2018.
Bozkurt, et al., "Safety assessment of near infrared light emitting diodes for diffuse optical measurements," BioMedical Engineering Online, 3(1):9, Mar. 22, 2004.
Buckley, et al., "Diffuse correlation spectroscopy formeasurement of cerebral blood flow: future prospects," Neurophotonics, 1(1): 011009-1-011009-7, Jul.-Sep. 2014.
Buschmann, et al., "Fetal oxygen saturation measurement by transmission pulse oximetry," The Lancet, 339: 615, Mar. 7, 1992.
Cahill, et al., "A prospective cohort study of fetal heart rate monitoring: deceleration area is predictive of feal acidemia," American Journal of Obstetrics & Gynecology, 218(5): 523.e1-523.e12, May 2018.
Caliskan, et al., "Reduction in caesarean delivery with fetal heartrate monitoring and intermittent pulse oximetryafter induction of labour with misoprostol," The Journal of Maternal-Fetal & Neonatal Medicine, 22(5): 445-451, 2009.
Carbonne et al. , "Multicenter oximetry study on the clinical value of fetal pulse oximetry," Am J Obstet Gynecol, 177(3): 593-598, 1997.
Carbonne, et al, "Fetal pulse oximetry: correlation between changes in oxygen saturation and neonatal outcome. Preliminary report on 39 cases," European Journal of Obstetrics & Gynecology and Reproductive Biology, 57: 73-77, 1994.
Carter, et al., "Calibration of a Reflectance Pulse Oximeter in Fetal Lambs for Arterial Oxygen Saturations Below 70%," J Soc Gynecol Invest, 5(5): 255-259, Sep.-Oct. 1998.
Cerebral Palsy Guidance, Cerebral Palsy, Cerebral Palsy Guidance Website, pp. 1 to 14, 2018.
Chan, et al., "Effects of Compression on Soft Tissue Optical Properties," IEEE Journal of Selected Topics in Quantum Electronics, 2(4): 943-950, Dec. 1996.
Chandraharan, "Fetal scalp blood sampling during labour: is it auseful diagnostic test or a historical test that nolonger has a place in modern clinical obstetrics?" Royal College of Obstetricians and Gynaecologists, www.bjog.org, pp. 1056-1062, Mar. 6, 2014.
Cheung, et al., "In vivo cerebrovascular measurement combining diffuse near-infrared absorption and correlation spectroscopies," Physics in Medicine & Biology, 46: 2053-2065, 2001.
Choe, "Diffuse Optical Tomography and Spectroscopy of Breast Cancer and Fetal Brain," Pub'd, Sep. 29, 2005, Faculties of the University of Pennsylvania.
Choe, et al., "Transabdominal near infrared oximetry of hypoxic stress in fetal sheep brain in utero," PNAS, 100(22): 12950-12954, Oct. 28, 2003.
Clark, et al., "Intrapartum management of category II fetal heart ratetracings: towards standardization of care," American Journal of Obstetrics & Gynecology, pp. 89-97, Aug. 2013.
Clark, et al., "The limits of electronic fetal heart rate monitoring in theprevention of neonatal metabolic acidemia," American Journal of Obstetrics & Gynecology, 216, pp. 163.e1-163.e6, Feb. 2017.
Colditz, et al., "Fetal pulse oximetry : Instrumentation and Recent Clinical Experience," Clinics in Perinatology, 26(4): 869-880, Dec. 1999.
Dassel, et al., "Reflectance Pulse Oximetry in Fetal Lambs," Pediatric Research, 31(3): 266-269, 1992.
De Blasi, et al., "Noninvasive measurement of human forearm oxygen consumption by near infrared spectroscopy," European Journal of Applied Physiology, 67: 20-25, 1993.
Delpy, et al., "Estimation of optical pathlength through tissue from direct time of flight measurement," Physics in Medicine & Biology, 33(12): 1433-1442, 1988.
Graham, et al., "A systematic review of the role of intrapartum hypoxia-ischemia in the causation of neonatal encephalopathy," American Journal of Obstetrics & Gynecology, pp. 587-595, Dec. 2008.
Greene, "Obstetricians Still Await a Deus ex Machina," The New England Journal of Medicine, 355: 2247-2248, Nov. 23, 2006.
Gregg, et al., "Brain specificity of diffuse optical imaging: improvements from superficial signal regression and tomography," Frontiers in NeuroEnergetics, 2(13), pp. 1-8, Jul. 14, 2010.
Grimes, et al., "Electronic Fetal Monitoring as a Public Health Screening Program: The Arithmetic of Failure," Obstetrics & Gynecology, 116(6): 1397-1400, Dec. 2010.
Gunn, et al., "Fetal Hypoxia Insults and Patterns of Brain Injury: Insights from Animal Models," Clin Perinatol, 36: 579-593, 2009.
Harini H., et al., "Design and Implementation of a Calibration— Free Pulse Oximeter", In: Goh J. (eds) The 15th International Conference on Biomedical Engineering. IFMBE Proceedings, vol. 43. Springer, Cham, pp. 100-103, 2014.
Haydon, et al., "The effect of maternal oxygen administration on fetal pulse oximetry during labor in fetuses with nonreassuring fetal heart rate patterns," American Journal of Obstetrics and Gynecology, 195: 735-738, 2006.
Haykin, In Kalman Filtering and Neural Networks, Ed. Simon Haykin, John Wiley & Sons, Inc., New York, NY, pp. 298, 2001.
Hiraoka, et al., "A Monte Carlo investigation of optical pathlength in inhomogeneous tissue and its application to near-infrared spectroscopy," Institute of Physics and Engineering in Medicine, 38: 1859-1876, 1993.
Hyvärinen, "Fast and Robust Fixed-Point Algorithms for Independent Component Analysis," IEEE Trans. on Neural Networks, 10(3): 626-634, 1999.
International Commission on Non-Ionizing Radiation Protection (ICNIRP), "ICNIRP Guidelines on Limits of Exposure to Incoherent Visible and Infrared Radiation," Health Physics, 105(1): 74-96; 2013.
International Search Report and the Written Opinion of the International Searching Authority for International Application No. PCT/US2017/062782, dated Feb. 19, 2018.
International Search Report and Written Opinion dated Mar. 13, 2017, from the International Searching Authority, for International Patent Application No. PCT/US2016/068994 (filed Dec. 28, 2016), 13 pages.
Jacques, "Corrigendum: Optical properties of biological tissues: a review," IOP Publishing, Phys. Med. Biol. 58: 5007-5008, Jun. 27, 2013.
Jacques, "Optical properties of biological tissues: a review," IOP Publishing, Phys. Med. Biol. 58: R37-R61, May 10, 2013.
Jezewski, et al., "Extraction of Fetal Heart-Rate Signal as the Time EventSeries From Evenly Sampled Data Acquired Using Doppler

(56) References Cited

OTHER PUBLICATIONS

Ultrasound Technique," IEEE Transactions on Biomedical Engineering, 55(2): 805-810, Feb. 2008.

Johnson et al., "Continuous fetal monitoring with a pulse oximeter: a case of cord compression," Am. J. Obstet. Gynecol., 161(5): 1295-1296, Nov. 1989 (Abstract only).

Johnson, et al., "Continuous Intrapartum Measurement of Fetal Oxygen Saturation," The Lancet, pp. 517, Aug. 27, 1988.

Johnson, et al., "Fetal monitoring with pulse oximetry," British Journal of Obstetrics and Gynaecology, 98: 36-41, Jan. 1991.

Julious, "Sample size of 12 per group rule ofthumb for a pilot study," Pharmaceut. Statist., 4: 287-291, 2005.

Jumadi, et al., "Transabdominal Fetal Pulse Oximeter Using LEDs and Photodiode: A Design Consideration Study," 2015 2nd International Conference on Biomedical Engineering (ICoBE), pp. 1-6, Mar. 30-31, 2015.

Jumadi, et al., Development of theoretical oxygen saturation calibration curve based on optical density ratio and optical simulation approach,: AIP Conference Proceedings 1883, pp. 1-11, Sep. 14, 2017.

Jumadi, et al., "Investigating the Effect of Total Radiated Power on Fetus Using Optical Simulation Approach Based on Exposure Safety Limit for Eye and Tissue Injury," Journal of Life Sciences and Technologies, 2(1): 24-27, Jun. 2014.

Jurovata, et al., "Simulation of Photon Propagation in Tissue Using Matlab", Faculty of Materials Science and Technology in Trnava Slovak University of Techology in Bratislava, Research Papers (2013), 21:31-37.

Kainerstorfer, et al., "Optical oximetry of volume-oscillating vascular compartments: contributions from oscillatory blood flow," Journal of Biomedical Optics, 21(10): 101408-1-101408-13, Oct. 2016.

Kelly, et al., "Dose-dependent relationship between acidosis at birth and likelihood of death or cerebral palsy," Arch Dis Child Fetal Neonatal Ed 2017, pp. F1-F6, 2017.

Kim, et al., "Noise reduction of PPG signal during Free Movements Using Adaptive SFLC (scaled Fourier linear combiner)," IFMBE proceedings, pp. 1083-1086, Jan. 2007.

Kirschbaum, et al., "Oxyhemoglobin dissociation characteristics of human and sheep maternal and fetal blood," Am. J. Obstetric and Gynecology, 96(5): 741-759, 1966.

Klauser, et al., "Use of fetal pulse oximetry among high-risk women in labor: A randomized clinical trial," American Journal of Obstetrics and Gynecology, 192: 1810-1817, 2005.

Kohl, et al., "Determination of the wavelength dependence of the differential pathlength factor from near-infrared pulse signals," Physics in Medicine & Biology, 43: 1771-1782, 1998.

Komalla, "A new method based on complex EMD for motion artifacts reduction in PPG signals for pulse oximeter application," Journal of Engineering Technology, Special Issue on Technology Applications and Innovations, 6: 187-200, 2017.

Konugolu Venkata Sekar, "Broadband Time-Domain Disffuse Optics for Clinical Diagnostics and Diffuse Raman Spectroscopy," Doctoral Dissertation, Politecnico de Milano, Physics Department, pp. 1-288, 2016.

Kuhnert, et al., "Intrapartum management of nonreassuring fetal heart rate patterns: A randomized controlled trial of fetal pulse oximetry," American Journal of Obstetrics and Gynecology, 191: 1989-1995, 2004.

Lakowicz et al., "Frequency-Domain Measurements of Photon Migration in Tissues," Chemical Physics Letters, 166(3): 246-252, Feb. 23, 1990.

Laqua, et al., "A phantom with pulsating artificial vessels for non-invasive fetal pulse oximetry", Conf Proc IEEE Eng Med Biol Soc. (2014), pp. 5631-5634.

Laqua, et al., "Improved FPGA controlled artificial vascular system for plethysmographic measurements", Current Directions in Biomedical Engineering (2016), 2(1): 689-693.

Laqua; et al., "FPGA controlled artificial vascular system", Current Directions in Biomedical Engineering (2015), 1:446-449.

Larosa, et al., Understanding the full Spectrum of Organ Injury Following Intrapartum Asphixia,: Frontiers in Pediatrics, 5(16): 1-11, Feb. 17, 2017.

Larsen, "Pulse Oximetry Devices Market," Meddevicetracker, Pharma Intelligence, pp. 1-58, Dec. 2017.

Lear, et al., "The peripheral chemoreflex: indefatigable guardian offetal physiological adaptation to labour," The Journal of Physiology, pp. 1-13, 2018.

Lemieux, et al., "Investigating non-Gaussian scattering processes by using nth-order intensity correlation functions," 16(7): 1651-1664, Jul. 1999.

Leszczynska-Gorzelak, et al., "Intrapartum cardiotocography and fetal pulse oximetry in assessing fetal hypoxia," International Journal of Gynecology & Obstetrics, 76: 9-14, 2002.

Louie, et al., "Four Types of Pulse Oximeters Accurately Detect Hypoxia during Low Perfusion and Motion," Anesthesiology, pp. 1 to 11, 2017.

Luttkus, et al., "Pulse oximetry during labour—does it give rise to hope? Value of saturation monitoring in comparison to fetal blood gas status," European Journal of Obstetrics & Gynecology and Reproductive Biology, 110: S132-S138, 2003.

Mallinckrodt, Inc., "(N-400) Fetal Oxygen Saturation Monitoring System," Summary of Safety and Eftectivenes Information Data, p. 31, 2000.

Mannheimer, et al., "Wavelength Selection for Low-Saturation Pulse Oximetry," IEEE Transactions on Biomedical Engineering, 44(3): 148-158, Mar. 1997.

Martinek, et al., "Non-Invasive Fetal Monitoring: A Maternal Surface ECG Electrode Placement-Based Novel Approach for Optimization of Adaptive Filter Control Parameters Using the LMS and RLS Algorithms," Sensors, 17: 1154, pp. 1-32, May 19, 2017.

Martinello, et al., Management and investigation of neonatal-encephalopathy: 2017 update,: Arch Dis Child Fetal Neonatal, 102: F346-F-358, 2017.

Mawn, et al., "Trans-abdominal Monitoring of Fetal Arterial Oxygen Saturation Using Pulse Oximetry," IEEE EMBS—NEBE, 227-228, 2002.

Meschia, et al., "A Comparison of the Oxygen Dissociation Curves of the Bloods of Maternal, Fetal and Newborn Sheep at Various pHs," In: Oxgen Dissociation Curves in Sheep at Various pHs, pp. 95-97, Sep. 23, 1960.

* cited by examiner

115A

1200

```
┌─────────────────────────────────────────────┐
│ Receive a first detected electronic signal  │
│ corresponding to a first optical signal     │
│ emitted from the abdomen of a pregnant      │
│ mammal and her fetus                        │
│ 1205                                        │
└─────────────────────────────────────────────┘
                    ↓
┌─────────────────────────────────────────────┐
│ Receive a second detected electronic        │
│ corresponding to a second optical signal    │
│ emitted from the abdomen of the pregnant    │
│ mammal and her fetus                        │
│ 1210                                        │
└─────────────────────────────────────────────┘
                    ↓
┌─────────────────────────────────────────────┐
│ Pre-process received detected electronic    │
│ signal                                      │
│ 1212                                        │
└─────────────────────────────────────────────┘
                    ↓
┌─────────────────────────────────────────────┐
│ Isolate a portion of the first and second   │
│ detected electronic signals that has been   │
│ incident on the fetus (first and second     │
│ fetal signals)                              │
│ 1215                                        │
└─────────────────────────────────────────────┘
                    ↓
┌─────────────────────────────────────────────┐
│ Determine a value of the PPG pulse          │
│ amplitude, at end-diastole ($I_D$), or AC   │
│ signal, for both isolated fetal signals     │
│ 1220                                        │
└─────────────────────────────────────────────┘
                    ↓
┌─────────────────────────────────────────────┐
│ Determine a minimum value of the PPG pulse  │
│ amplitude during systole ($I_S$) or DC      │
│ signal for both isolated fetal signals      │
│ 1225                                        │
└─────────────────────────────────────────────┘
                    ↓
┌─────────────────────────────────────────────┐
│ Determine a value for a ratio of ratios (R) │
│ for the fetus                               │
│ 1230                                        │
└─────────────────────────────────────────────┘
```

```
┌─────────────────────────────────────────┐
│ Receive a first detected electronic     │
│ signal of a first wavelength            │
│ corresponding to a first optical signal │
│ exiting from the abdomen of a pregnant  │
│ mammal and her fetus                    │
│ 1305                                    │
└─────────────────────────────────────────┘
                    ↓
┌─────────────────────────────────────────┐
│ Receive a second detected electronic    │
│ signal of a second wavelength           │
│ corresponding to a second optical signal│
│ exiting from the abdomen of the pregnant│
│ mammal and her fetus                    │
│ 1310                                    │
└─────────────────────────────────────────┘
                    ↓
┌─────────────────────────────────────────┐
│ Pre-process received detected electronic signal │
│ 1312                                    │
└─────────────────────────────────────────┘
                    ↓
┌─────────────────────────────────────────┐
│ Isolate a portion of the first and second│
│ detected electronic signals that has been│
│ incident on the fetus                   │
│ (first and second fetal signals)        │
│ 1315                                    │
└─────────────────────────────────────────┘
                    ↓
┌─────────────────────────────────────────┐
│ Receive a R value for the fetus or a    │
│ pulse oximetry device                   │
│ 1320                                    │
└─────────────────────────────────────────┘
                    ↓
┌─────────────────────────────────────────┐
│ Analyze the first and second fetal      │
│ signals to determine fetal hemoglobin   │
│ oxygen saturation level                 │
│ 1325                                    │
└─────────────────────────────────────────┘
                    ↓
┌─────────────────────────────────────────┐
│ Facilitate provision of an indication of│
│ the fetal hemoglobin oxygen saturation  │
│ level to an operator                    │
│ 1330                                    │
└─────────────────────────────────────────┘
```

FIG. 13

SYSTEMS, DEVICES, AND METHODS FOR PERFORMING TRANS-ABDOMINAL FETAL OXIMETRY AND/OR TRANS-ABDOMINAL FETAL PULSE OXIMETRY USING DIFFUSE OPTICAL TOMOGRAPHY

RELATED APPLICATIONS

This application is a CONTINUATION OF PCT/US19/40639, entitled "SYSTEMS, DEVICES, AND METHODS FOR PERFORMING TRANS-ABDOMINAL FETAL OXIMETRY AND/OR TRANS-ABDOMINAL FETAL PULSE OXIMETRY USING DIFFUSE OPTICAL TOMOGRAPHY," filed Jul. 3, 2019, which is a NON-PROVISIONAL application of U.S. Provisional Patent Application No. 62/694,122 filed on Jul. 5, 2018 entitled "SYSTEMS, DEVICES, AND METHODS FOR PERFORMING TRANS-ABDOMINAL FETAL OXIMETRY AND/OR TRANS-ABDOMINAL FETAL PULSE OXIMETRY USING MATERNAL AND/OR FETAL HEART RATE"; a NON-PROVISIONAL application of U.S. Provisional Patent Application No. 62/694,130 filed on Jul. 5, 2018 entitled "SYSTEMS, DEVICES, AND METHODS FOR PERFORMING TRANS-ABDOMINAL FETAL OXIMETRY AND/OR TRANS-ABDOMINAL FETAL PULSE OXIMETRY USING SHORT SEPARATION MEASUREMENTS"; a NON-PROVISIONAL U.S. Provisional Patent Application No. 62/694,135 filed Jul. 5, 2019 entitled "SYSTEMS, DEVICES, AND METHODS FOR PERFORMING TRANS-ABDOMINAL FETAL OXIMETRY AND/OR TRANS-ABDOMINAL FETAL PULSE OXIMETRY USING DIFFUSE OPTICAL TOMOGRAPHY"; a NON-PROVISIONAL application of U.S. Provisional Patent Application No. 62/694,146 filed on Jul. 5, 2018 entitled "SYSTEMS, DEVICES, AND METHODS FOR DETERMINING AN INDIVIDUALIZED RATIO OF RATIOS FOR A PULSE OXIMETER IN THE CONTEXT OF TRANS-ABDOMINAL FETAL OXIMETRY AND/OR TRANS-ABDOMINAL FETAL PULSE OXIMETRY"; a NON-PROVISIONAL application of U.S. Provisional Patent Application No. 62/694,170 filed on Jul. 5, 2018 entitled "SYSTEMS, DEVICES, AND METHODS FOR PERFORMING TRANS ABDOMINAL FETAL OXIMETRY AND/OR TRANS-ABDOMINAL FETAL PULSE OXIMETRY USING A BROAD SPECTRUM LIGHT SOURCE"; a NON-PROVISIONAL application of U.S. Provisional Patent Application No. 62/694,184 filed on Jul. 5, 2018 entitled "SYSTEMS, DEVICES, AND METHODS FOR PERFORMING TRANS ABDOMINAL FETAL OXIMETRY AND/OR TRANS-ABDOMINAL FETAL PULSE OXIMETRY USING FREQUENCY-DOMAIN SPECTROSCOPY"; a NONPROVISIONAL application of U.S. Provisional Patent Application No. 62/694,199 filed on Jul. 5, 2018 entitled "SYSTEMS, DEVICES, AND METHODS FOR PERFORMING TRANS-ABDOMINAL FETAL OXIMETRY AND/OR TRANS ABDOMINAL FETAL PULSE OXIMETRY USING TIME-DOMAIN DIFFUSE CORRELATION SPECTROSCOPY"; and a NON-PROVISIONAL application of U.S. Provisional Patent Application No. 62/694,261 filed on Jul. 5, 2018 entitled "SYSTEMS, DEVICES, AND METHODS FOR PERFORMING TRANS-ABDOMINAL MECONIUM DETECTION", all of which are incorporated herein by reference in their respective entireties.

FIELD OF INVENTION

The present invention is in the field of medical devices and, more particularly, in the field of trans-abdominal fetal oximetry, trans-abdominal fetal pulse oximetry, diffuse optical tomography and fetal tissue oxygenation.

BACKGROUND

Oximetry is a method for determining the oxygen saturation of hemoglobin in a mammal's blood. Typically, 90% (or higher) of an adult human's hemoglobin is saturated with (i.e., bound to) oxygen while only 30-60% of a fetus's blood is saturated with oxygen. Pulse oximetry is a type of oximetry that uses changes in blood volume through a heartbeat cycle to internally calibrate hemoglobin oxygen saturation measurements of the arterial blood.

Current methods of monitoring fetal health, such as monitoring fetal heart rate, are inefficient at determining levels of fetal distress and, at times, provide false positive results indicating fetal distress that may result in the unnecessary performance of a Cesarean delivery.

SUMMARY

Systems, methods, and devices for determining fetal hemoglobin oxygen saturation levels and/or fetal tissue oxygenation levels using, for example, trans-abdominal fetal oximetry, trans-abdominal fetal pulse oximetry, and/or diffuse optical tomography (DOT) are herein described.

In one embodiment, a processor may receive a plurality of detected electronic signals from one or more detectors communicatively coupled to the processor. The detectors may be arranged in an array with one or more light sources. The detected electronic signals may correspond to light of two or more wavelengths projected into, and emitted from (via, for example, back scattering and/or transmission) a pregnant mammal's abdomen and/or a fetus contained therein that has been detected by the detector(s) and converted into one or more digital signals that is/are the plurality of detected electronic signals. The emitted and detected light may be a portion of light projected into the pregnant mammal's abdomen and fetus contained therein by the one or more light sources. In some embodiments, the received plurality of detected electronic signals are synchronized in a time domain so that each of the signals correspond to one another in time (e.g., have the same start time, same end time, etc.). This synchronization may be achieved via alignment or correlation of timestamps present in the plurality of detected electronic signals. The timestamps may be introduced into the detected electronic signals by a timestamping device (e.g., source of an electrical ground) that simultaneously, or nearly simultaneously, interrupts each of the detected electronic signals so that each of these respective signals have a common start time.

Optionally, an indication of a depth of the fetus within the pregnant mammal's abdomen may be received. Fetal depth may correspond to, for example, a distance between the pregnant mammal's epidermis and the fetus's epidermis or a distance between the pregnant mammal's epidermis and the fetus's brain at a particular location. The depth of the fetus may be received from, for example, an ultra-sound device, a Doppler device, and/or an image (e.g., MRI) of the pregnant mammal's abdomen.

A portion, or portions, of the detected electronic signals that correspond to light that was incident upon the fetus may be isolated from the detected electronic signals responsively to the indication of the depth of the fetus (sometimes referred to herein as "isolated fetal signal" or "fetal signal"). This isolation may be performed using, for example, a time of flight for photons expected to be incident upon the fetus and/or a location, direction, and/or position associated with a detected photon or series of photons.

In some embodiments, the determining of the portion of the detected electronic signals that correspond to light that was incident upon the fetus may include receiving a secondary signal and analyzing the received plurality of detected electronic signals using the secondary signal to isolate a portion of the plurality of detected electronic signals corresponding to light that was incident upon the fetus.

Additionally, or alternatively, the determining of the portion of the detected electronic signals that correspond to light that was incident upon the fetus may include receiving a heartrate signal for the pregnant mammal from, for example, an ECG machine and/or a pulse oximeter. The received plurality of detected electronic signals may then be analyzed and/or processed using the heartrate signal for the pregnant mammal to isolate a portion of the plurality of detected electronic signals corresponding to light that was incident upon the fetus.

Additionally, or alternatively, the determining of the portion of the detected electronic signals that correspond to light that was incident upon the fetus may include receiving a respiratory signal for the pregnant mammal and analyzing/processing the received plurality of detected electronic signals using the respiratory signal for the pregnant mammal to isolate a portion of the plurality of detected electronic signals corresponding to light that was incident upon the fetus.

Additionally, or alternatively, the determining of the portion of the detected electronic signals that correspond to light that was incident upon the fetus may include receiving a heartrate signal for the fetus and analyzing the received plurality of detected electronic signals using the heartrate signal for the fetus to isolate the portion of the received plurality of detected electronic signals corresponding to light that was incident upon the fetus.

Additionally, or alternatively, the determining of the portion of the detected electronic signals that correspond to light that was incident upon the fetus may include receiving one or more short separation signals that may correspond to light that is only incident upon the abdomen of the pregnant mammal (i.e., is not expected to be incident upon the fetus) and analyzing the received plurality of detected electronic signals using the short separation signal to remove portions of the detected electronic signals that correspond to the short separation signal(s).

A fetal tissue oxygen saturation level may then be determined using the isolated portion of the detected electronic signals that correspond to light that was incident upon the fetus. Provision of the fetal tissue oxygen saturation level to a user may then be facilitated by, for example, providing fetal tissue oxygen saturation level to a monitor or other display device.

In some embodiments, the detected electronic signals and/or the isolated fetal signal may be used to generate an image of the fetus, or a portion thereof, using the portion of the detected electronic signals that correspond to light that was incident upon the fetus. The image may, for example, indicate regional variations of an intensity of detected light and/or tissue oxygen saturation level for the fetus and/or pregnant mammal.

In another embodiment, a processor may receive a plurality of detected electronic signals from one or more detectors communicatively coupled to the processor. The detectors may be arranged in an array with one or more light sources. The detected electronic signals may correspond to light of two or more wavelengths projected into, and emitted from (via, for example, back scattering and/or transmission) a pregnant mammal's abdomen and a fetus contained therein that has been detected by the detector(s) and converted into one or more digital signals that is/are the plurality of detected electronic signals. The emitted and detected light may be a portion of light projected into the pregnant mammal's abdomen and fetus contained therein by the one or more light sources. In some embodiments, the received plurality of detected electronic signals are synchronized in a time domain (via, for example, a time stamp) so that each of the signals correspond to one another in time (e.g., have the same start time, same end time, etc.).

A short separation signal corresponding to light that is only incident upon the abdomen of the pregnant mammal may be received and a portion, or portions, of the detected electronic signals that correspond to light that was incident upon the fetus may be isolated from the detected electronic signals (sometimes referred to herein as "isolated fetal signal" or "fetal signal") responsively to the short separation signal.

In some embodiments, the determining of the portion of the detected electronic signals that correspond to light that was incident upon the fetus may also include receiving a secondary signal and analyzing the received plurality of detected electronic signals using the secondary signal to isolate a portion of the plurality of detected electronic signals corresponding to light that was incident upon the fetus.

Additionally, or alternatively, the determining of the portion of the detected electronic signals that correspond to light that was incident upon the fetus may include receiving a heartrate signal for the pregnant mammal from, for example, an ECG machine and/or a pulse oximeter. The received plurality of detected electronic signals may then be analyzed and/or processed using the heartrate signal for the pregnant mammal to isolate a portion of the plurality of detected electronic signals corresponding to light that was incident upon the fetus.

Additionally, or alternatively, the determining of the portion of the detected electronic signals that correspond to light that was incident upon the fetus may include receiving a respiratory signal for the pregnant mammal and analyzing/processing the received plurality of detected electronic signals using the respiratory signal for the pregnant mammal to isolate a portion of the plurality of detected electronic signals corresponding to light that was incident upon the fetus.

Additionally, or alternatively, the determining of the portion of the detected electronic signals that correspond to light that was incident upon the fetus may include receiving a heartrate signal for the fetus and analyzing the received plurality of detected electronic signals using the heartrate signal for the fetus to isolate the portion of the received plurality of detected electronic signals corresponding to light that was incident upon the fetus.

A fetal tissue oxygen saturation level may then be determined using the isolated portion of the detected electronic signals that correspond to light that was incident upon the fetus. Provision of the fetal tissue oxygen saturation level to a user may then be facilitated by, for example, providing the fetal tissue oxygen saturation level to a monitor or other display device.

In some embodiments, the detected electronic signals and/or the isolated fetal signal may be used to generate an image of the fetus, or a portion thereof, using the portion of the detected electronic signals that correspond to light that was incident upon the fetus. The image may, for example, indicate regional variations of fetal tissue oxygen saturation level and/or pregnant mammal.

BRIEF DESCRIPTION OF THE FIGURES

FIG. 12 is a flowchart illustrating a process for determining an individualized ratio of ratios (R) value for a pulse oximeter, consistent with some embodiments of the present invention;

FIG. 13 is a flowchart illustrating a process for determining a level of oxygen saturation for fetal hemoglobin, consistent with some embodiments of the present invention;

DESCRIPTION

Figure 1A:
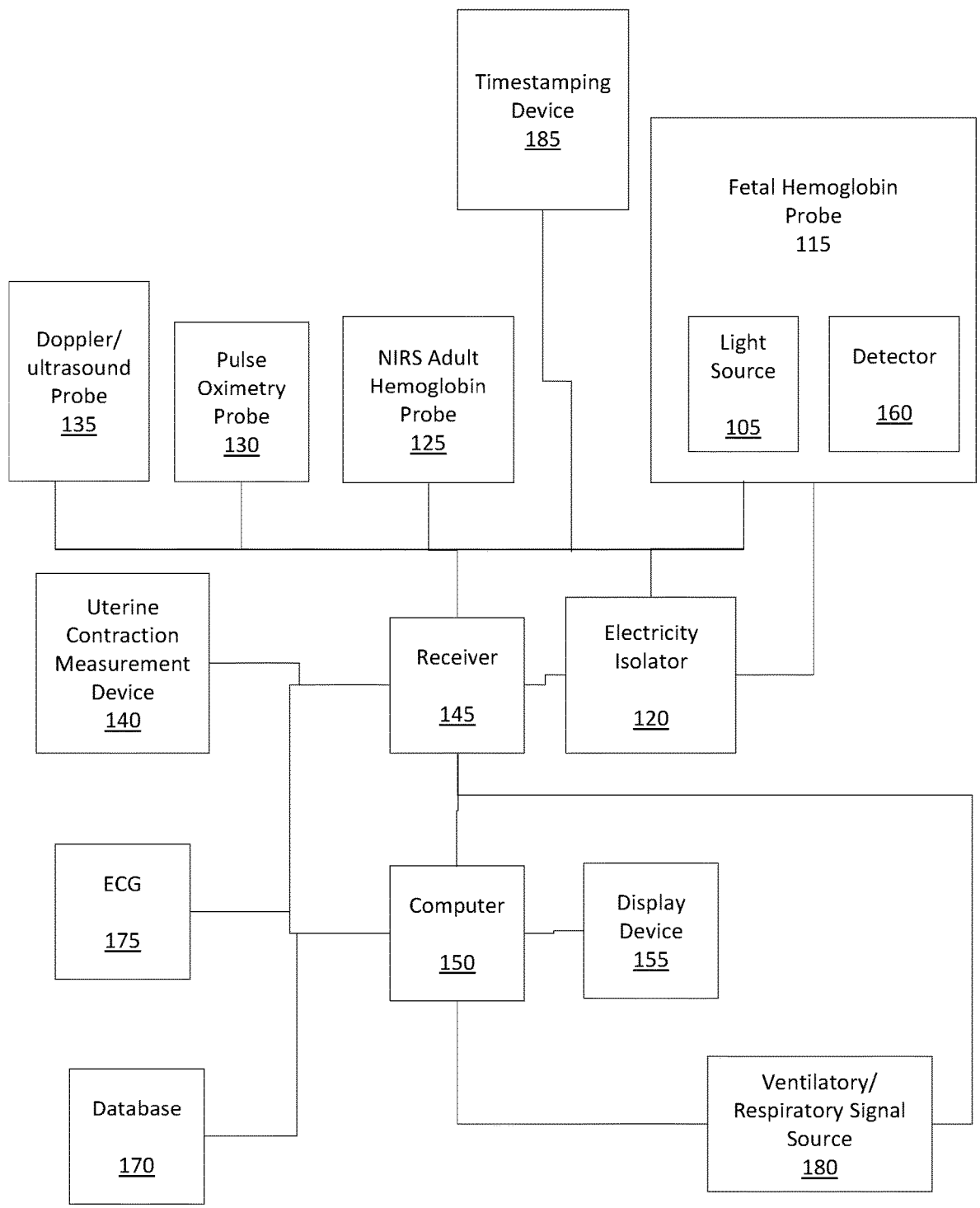
FIG. 1A is a block diagram illustrating an exemplary system for determining a level of oxygen saturation for fetal hemoglobin and/or whether meconium is present in the amniotic fluid of a pregnant mammal, consistent with some embodiments of the present invention.

Described herein are systems, devices, and methods for performing transabdominal fetal oximetry, fetal pulse oximetry, and diffuse optical tomography (DOT). An output of fetal oximetry and/or fetal pulse oximetry is the level of oxygen saturation of the fetus's blood (also referred to herein as "fetal hemoglobin oxygen saturation level" and "oxygen saturation level") which may also be understood as the percentage of hemoglobin present in the fetus's blood that is bound to oxygen. An output of DOT is the level of oxygen saturation of the fetus's tissue (e.g., brain, skin, muscle, etc.). The oxygen saturation level of a fetus's blood and/or fetal tissue oxygenation levels may be used (e.g., by trained medical professionals) to assess the health of a fetus as well as a level of oxygen deprivation stress it may be under during, for example, a labor and delivery process, an in-utero fetal procedure, and/or a procedure or treatment administered to the pregnant mammal. Typically values of oxygen saturation for fetal blood fall within the range of 30-60% with anything lower than 30% indicating that the fetus may be in distress. At times, the oxygen saturation level may be determined using a ratio of rations ("R"), which provides and indicator for how light passes through maternal and/or fetal tissue.

Traditionally, pulse oximetry is performed by using two different beams of light, each of which are of a different wavelength or range of wavelengths. Often times, a beam of light within the red spectrum and a beam of light within the near-infra red (NIR) or two beams within the NIR spectrum are used. These two wavelengths have different path lengths (i.e., depth of penetration into the tissue) when transmitted through tissue that must be accounted for with a calibration factor related to path length ($I_1$ or $I_2$). Traditionally, a standard calibration factor is provided for pulse oximetry equipment by the equipment manufacture. While, use of a such a standard calibration factor works in situations where the light passes through tissue that is relatively homogeneous (e.g., thickness, composition, etc.) as may the case with a finger or ear lobe, when tissue is inhomogeneous (as is the case with a pregnant mammal's abdomen), the robustness of calculations made using this standard calibration factor decreases and confidence in the accuracy of generated values may fall below an acceptable level.

However, because a wavelength of a light beam determines its path length through tissue, if wavelengths of two beams of light are sufficiently close together, then a path length for each respective beam may be sufficiently similar to one another to reduce the effect of the path length on the oximetry calculations to zero or sufficiently close to zero. This may make oximetry calculations that contribute to the determination of fetal hemoglobin oxygen saturation described herein more accurate and easier to perform.

Fetal hemoglobin oxygen saturation may be determined in a variety of ways using, for example, various inputs and equations examples of which are disclosed herein. These examples are provided by way of explanation and not limitation. In some embodiments, two or more methods of determining a fetus's hemoglobin oxygen saturation may be combined to achieve, for example, a more accurate fetal hemoglobin oxygen saturation and/or a fetal hemoglobin oxygen saturation value that has a high level of confidence and/or statistical robustness. In some instances, the fetal hemoglobin oxygen saturation may be determined via oximetry and, in other instances, the fetal hemoglobin oxygen saturation may be determined using pulse oximetry.

In some embodiments, diffuse optical tomography, or DOT, may be used to determine an oxygen saturation of fetal tissue. DOT is a tissue imaging technique that may be used to measure spatial-temporal variations in the light absorption and scattering properties of tissue and regional variations in oxygen concentration. Based on these measurements, spatial maps of tissue properties such as total oxygen concentration and how tissue, or cells, scatter incident light may be obtained using, for example, model-based reconstruction algorithms. In the embodiments disclosed herein, the tissue being imaged is maternal abdominal tissue and fetal tissue including, but not limited to, fetal skin, muscle, and/or brain tissue.

DOT may be performed by projecting low-energy electromagnetic radiation (typically NIR light) into one or more locations on the surface of a body and measuring an intensity (e.g., a number of photons) of transmitted and/or back reflected light detected by one or more photo-electric detector(s). A DOT system typically includes a plurality of lasers (e.g., synchronized picosecond pulsed diode lasers) or optical fibers coupled to one or more lasers, a plurality of sensitive photo-electric detectors (e.g., single photon sensitive detectors), and a processor configured to process the output of the photo-electric detectors. The plurality of lasers or optical fibers and photo-electric detectors may be arranged in an array configured to cover and conform to a portion of a pregnant mammal's abdomen so that a fetus therein may be imaged.

When the incident laser light, or pulses, enter the abdomen, they may be broadened and attenuated by the maternal and fetal tissue layers and reflections of the incident light from and/or light that passes through these tissue layers may be detected by the photo-detectors. Characteristics of the detected light/photons (e.g., shape, time of flight, location of detection, power, intensity, etc.) may then analyzed to generate images of the tissue under study (e.g., the fetal tissue). The analysis may include application of physical models (e.g., a model of tissue layers for a maternal abdomen that may be general models or models specific to the pregnant mammal under study). Often, the propagation of light through tissue depends upon the scattering and absorption characteristics of the tissue, or a particular layer of tissue (when imaging multiple layers). The effects of this scattering may be understood through the use of, for example, models that employ scattering coefficients, absorption coefficients, and other properties to the detected light/photons. That may be specific to a particular type of tissue (e.g., fat, skin, muscle, etc.). In some instances, the scattering and/or absorption coefficients may be specific to a particular pregnant mammal and/or fetus being studied.

In some embodiments, DOT may be used to image the maternal abdomen to examine oxygen concentration of the portions of the image representing the fetus to determine fetal tissue oxygen saturation, which may be interpreted as an indicator of fetal health and/or an indicator of a likelihood of fetal acidosis. In some instances where the fetal location is known (e.g., through ultrasound), only the portions of the DOT image that correspond with the fetus's location may be studied to determine a level of fetal tissue oxygen saturation. In some embodiments, a portion of the DOT image and/or other information gathered via DOT that corresponds with the maternal tissue may be ignored. In other embodiments, a portion of the DOT image and/or other information gathered via DOT that corresponds with the maternal tissue may be used to separate a portion of the DOT image and/or other information gathered via DOT the corresponds with fetal tissue from a portion of the DOT image and/or other information gathered via DOT the corresponds to the mother.

Additionally, or alternatively, diffuse imaging correlation spectroscopy (DCS) may be used to determine a fetal hemoglobin oxygen saturation. DCS is an imaging technique where light is projected into a subject and light exiting (via e.g., transmission and/or back scattering) the subject is detected by a photodetector. Analysis (e.g., quantifying temporal fluctuations of light fields emerging from the tissue, which may be caused by moving blood cells) of the exiting light/photons may enables determination of, for example, blood flow and/or hemoglobin oxygenation of the subject. At times, tissue (e.g., skin, muscle, fat, etc.) overlaying an area of interest may confound the signal. With regard to the present invention, the area of interest may be a fetus within a maternal abdomen and the confounding effects of the layers of maternal tissue positioned between a DCS system and the fetus are undesired. A way to reduce the confounding effects of the maternal tissue is to use a time-domain (TD) DCS system (TD-DCS).

When a TD system is used, DCS may be performed using brief (e.g., 10-50 ps) light pulses that may be sinusoidally modulated with a frequency between, for example, 100 and 1000 MHz that are projected in the pregnant mammal's abdomen at a repetition rate of, for example, 1-50 MHz. These pulses may yield photon-density waves inside the imaged tissue. From there, amplitude differences and phase shifts between the incident light and detected light may be determined as a function of time. Emitted photons (e.g., back reflected or transmitted) may then be either collected by an optical fiber and guided to a detector (e.g., photomultiplier) or directly detected by the detector, which may be a microchannel plate photomultiplier (MCP-PMT). The MCP-PMT signals may then be amplified and/or attenuated and input into a constant fraction discriminator (CFD), the output of which may be provided to a time-to-amplitude converter (TAC). Output of the TAC may be counted as discrete events by a pulse-height analyzer (PHA) and accumulated until a peak count is reached (e.g., 100,000 counts, 1,000,000 counts, etc.). This information may be used to generate a time-response curve that is used to generate an image of the pregnant mammal's abdomen and/or determine a fetal hemoglobin oxygen saturation.

DCS instrumentation consists of three main components: a long-coherence-length (>5 m) laser operating in the NIR to deliver light to the tissue; single photon counting avalanche photodiode (APD) detectors that output an electronic pulse for every photon received; and a photon correlator that keeps track of the arrival times of all photons detected by the APDs and derives an intensity correlation function from the temporal separations of all pairs of photons. The correlator may be a piece of hardware and/or a software computation of temporal correlation functions.

The systems, devices, and methods disclosed herein may be used to monitor the health of a fetus during gestation and/or during the labor and delivery process. Additionally, or alternatively, systems, devices, and methods disclosed herein may be used to monitor the health of a fetus while the pregnant mammal is stressed and/or undergoing a medical procedure that may, or may not be, related to the pregnancy. Additionally, or alternatively, systems, devices, and methods disclosed herein may be used to monitor the health of a fetus during in-utero fetal procedures (e.g., amniocentesis or surgery).

FIG. 1A provides an exemplary system 100 for detecting and/or determining fetal hemoglobin oxygen saturation levels. The components of system 100 may be coupled together via wired and/or wireless communication links. In some instances, wireless communication of one or more components of system 100 may be enabled using short-range wireless communication protocols designed to communicate over relatively short distances (e.g., BLUETOOTH®, near field communication (NFC), radio-frequency identification (RFID), and Wi-Fi) with, for example, a computer or personal electronic device (e.g., tablet computer or smart phone) as described below.

System 100 includes a light source 105 and a detector 160 that, at times, may be housed in a single housing, which may be referred to as fetal probe 115. Light source 105 may include a single, or multiple light sources and detector 160 may include a single, or multiple detectors.

Light sources 105 may transmit light at light of one or more wavelengths, including NIR, into the pregnant mammal's abdomen. Typically, the light emitted by light sources 105 will be focused or emitted as a narrow beam to reduce spreading of the light upon entry into the pregnant mammal's abdomen. Light sources 105 may be, for example, a LED, and/or a LASER, a tunable light bulb and/or a tunable LED that may be coupled to a fiber optic cable. On some occasions, the light sources may be one or more fiber optic cables optically coupled to a laser and arranged in an array. In some instances, the light sources 105 may be tunable or otherwise user configurable while, in other instances, one or more of the light sources may be configured to emit light within a pre-defined range of wavelengths. Additionally, or alternatively, one or more filters (not shown) and/or polarizers may filter/polarize the light emitted by light sources 105 to be of one or more preferred wavelengths. These filters/polarizers may also be tunable or user configurable.

An exemplary light source 105 may have a relatively small form factor and may operate with high efficiency, which may serve to, for example, conserve space and/or limit heat emitted by the light source 105. In one embodiment, light source 105 is configured to emit light in the range of 770-850 nm. Exemplary flux ratios for light sources include, but are not limited to a luminous flux/radiant flux of 175-260 mW, a total radiant flux of 300-550 mW and a power rating of 0.6 W-3.5 W.

Detector 160 may be configured to detect a light signal emitted from the pregnant mammal and/or the fetus via, for example, transmission and/or back scattering. Detector 160 may convert this light signal into an electronic signal, which may be communicated to a computer or processor and/or an on-board transceiver that may be capable of communicating the signal to the computer/processor. This emitted light might then be processed in order to determine how much light, at various wavelengths, passes through the fetus and/or is reflected and/or absorbed by the fetal oxyhemoglobin and/or de-oxyhemoglobin so that a fetal hemoglobin oxygen saturation level may be determined. This processing will be discussed in greater detail below. In some embodiments, detector 160 may be configured to detect/count single photons Exemplary detectors include, but are not limited to, cameras, traditional photomultiplier tubes (PMTs), silicon PMTs, avalanche photodiodes, and silicon photodiodes. In some embodiments, the detectors will have a relatively low cost (e.g., $50 or below), a low voltage requirement (e.g., less than 100 volts), and non-glass (e.g., plastic) form factor. In other embodiments, (e.g., contactless pulse oximetry) a sensitive camera may be deployed to receive light emitted by the pregnant mammal's abdomen. For example, detector 160 may be a sensitive camera adapted to capture small changes in fetal skin tone caused by changes in cardiovascular pressure associated with fetal myocardial contractions. In these embodiments, detector 160 and/or fetal probe 115 may be in contact with the pregnant mammal's abdomen, or not, as this embodiment may be used to perform so-called contactless pulse oximetry. In these embodiments, light sources 105 may be adapted to provide light (e.g., in the visible spectrum, near-infrared, etc.) directed toward the pregnant mammal's abdomen so that the detector 160 is able to receive/detect light emitted by the pregnant mammal's abdomen and fetus. The emitted light captured by detector 160 may be communicated to computer 150 for processing to convert the images to a measurement of fetal hemoglobin oxygen saturation according to, for example, one or more of the processes described herein.

A fetal probe 115, light source 105, and/or detector 160 may be of any appropriate size and, in some circumstances, may be sized so as to accommodate the size of the pregnant mammal using any appropriate sizing system (e.g., waist size and/or small, medium, large, etc.). Exemplary lengths for a fetal probe 115 include a length of 4 cm-40 cm and a width of 2 cm-10 cm. In some circumstances, the size and/or configuration of a fetal probe 115, or components thereof, may be responsive to skin pigmentation of the pregnant mammal and/or fetus. In some instances, the fetal probe 115 may be applied to the pregnant mammal's skin via tape or a strap that cooperates with a mechanism (e.g., snap, loop, etc.) (not shown). In some instances, fetal probe 115 may act to pre-process or filter detected signals.

System 100 includes a number of optional independent sensors/probes designed to monitor various aspects of maternal and/or fetal health and may be in contact with a pregnant mammal. These probes/sensors are a NIRS adult hemoglobin probe 125, a pulse oximetry probe 130, a Doppler and/or ultrasound probe 135, and a uterine contraction measurement device 140. Not all embodiments of system 100 will include all of these components. In some embodiments, system 100 may also include an electrocardiography (ECG) machine (not shown) that may be used to determine the pregnant mammal's and/or fetus's heart rate and/or an intrauterine pulse oximetry probe (not shown) that may be used to determine the fetus's heart rate. The Doppler and/or ultrasound probe 135 may be configured to be placed on the abdomen of the pregnant mammal and may be of a size and shape that approximates a silver U.S. dollar coin and may provide information regarding fetal position, orientation, and/or heart rate. Pulse oximetry probe 130 may be a conventional pulse oximetry probe placed on pregnant mammal's hand and/or finger to measure the pregnant mammal's hemoglobin oxygen saturation. NIRS adult hemoglobin probe 125 may be placed on, for example, the pregnant mammal's 2nd finger and may be configured to, for example, use near infrared spectroscopy to calculate the ratio of adult oxyhemoglobin to adult de-oxyhemoglobin. NIRS adult hemoglobin probe 125 may also be used to determine the pregnant mammal's heart rate.

Optionally, system 100 may include a uterine contraction measurement device 140 configured to measure the strength and/or timing of the pregnant mammal's uterine contractions. In some embodiments, uterine contractions will be measured by uterine contraction measurement device 140 as a function of pressure (e.g., measured in e.g., mmHg) over time. In some instances, the uterine contraction measurement device 140 is and/or includes a tocotransducer, which is an instrument that includes a pressure-sensing area that detects changes in the abdominal contour to measure uterine activity and, in this way, monitors frequency and duration of contractions.

In another embodiment, uterine contraction measurement device 140 may be configured to pass an electrical current through the pregnant mammal and measure changes in the electrical current as the uterus contracts. Additionally, or alternatively, uterine contractions may also be measured via near infrared spectroscopy using, for example, light received/detected by detector 160 because uterine contractions, which are muscle contractions, are oscillations of the uterine muscle between a contracted state and a relaxed state. Oxygen consumption of the uterine muscle during both of these stages is different and these differences may be detectable using NIRS.

Measurements and/or signals from NIRS adult hemoglobin probe 125, pulse oximetry probe 130, Doppler and/or ultrasound probe 135, and/or uterine contraction measurement device 140 may be communicated to receiver 145 for communication to computer 150 and display on display device 155 and, in some instances, may be considered secondary signals. As will be discussed below, measurements provided by NIRS adult hemoglobin probe 125, pulse oximetry probe 130, a Doppler and/or ultrasound probe 135, uterine contraction measurement device 140 may be used in conjunction with fetal probe 115 to isolate a fetal pulse signal and/or fetal heart rate from a maternal pulse signal and/or maternal heart rate. Receiver 145 may be configured to receive signals and/or data from one or more components of system 100 including, but not limited to, fetal probe 115, NIRS adult hemoglobin probe 125, pulse oximetry probe 130, Doppler and/or ultrasound probe 135, and/or uterine contraction measurement device 140. Communication of receiver 145 with other components of system may be made using wired or wireless communication.

In some instances, one or more of NIRS adult hemoglobin probe 125, pulse oximetry probe 130, a Doppler and/or ultrasound probe 135, uterine contraction measurement device 140 may include a dedicated display that provides the measurements to, for example, a user or medical treatment provider. It is important to note that not all of these probes may be used in every instance. For example, when the pregnant mammal is using fetal probe 115 in a setting outside of a hospital or treatment facility (e.g., at home or work) then, some of the probes (e.g., NIRS adult hemoglobin probe 125, pulse oximetry probe 130, a Doppler and/or ultrasound probe 135, uterine contraction measurement device 140) of system 100 may not be used.

In some instances, receiver 145 may be configured to process or pre-process received signals so as to, for example, make the signals compatible with computer 150 (e.g., convert an optical signal to an electrical signal), improve signal to noise ratio (SNR), amplify a received signal, etc. In some instances, receiver 145 may be resident within and/or a component of computer 150. In some embodiments, computer 150 may amplify or otherwise condition the received detected signal so as to, for example, improve the signal-to-noise ratio.

Receiver 145 may communicate received, pre-processed, and/or processed signals to computer 150. Computer 150 may act to process the received signals, as discussed in greater detail below, and facilitate provision of the results to a display device 155. Exemplary computers 150 include desktop and laptop computers, servers, tablet computers, personal electronic devices, mobile devices (e.g., smart phones), and the like. Exemplary display devices 155 are computer monitors, tablet computer devices, and displays provided by one or more of the components of system 100. In some instances, display device 155 may be resident in receiver 145 and/or computer 150. Computer 150 may be communicatively coupled to database 170, which may be configured to store information regarding physiological characteristic and/or combinations of physiological characteristic of pregnant mammals and/or their fetuses, impacts of physiological characteristic on light behavior, information regarding the calculation of hemoglobin oxygen saturation levels, calibration factors, and so on.

In some embodiments, a pregnant mammal may be electrically insulated from one or more components of system 100 by, for example, an electricity isolator 120. Exemplary electricity insulators 120 include circuit breakers, ground fault switches, and fuses.

In some embodiments, system 100 may include an electro-cardio gram (ECG) machine 175 configured to ascertain characteristics of the pregnant mammal's heart rate and/or pulse and/or measure same. These characteristics may be used as, for example, a secondary signal and/or maternal heart rate signal as disclosed herein.

In some embodiments, system 100 may include a ventilatory/respiratory signal source 180 that may be configured to monitor the pregnant mammal's respiratory rate and provide a respiratory signal indicating the pregnant mammal's respiratory rate to, for example, computer 150. Additionally, or alternatively, ventilatory/respiratory signal source 180 may be a source of a ventilatory signal obtained via, for example, cooperation with a ventilation machine. Exemplary ventilatory/respiratory signal sources 180 include, but are not limited to, a carbon dioxide measurement device, a stethoscope and/or electronic acoustic stethoscope, a device that measures chest excursion for the pregnant mammal, and a pulse oximeter. A signal from a pulse oximeter may be analyzed to determine variations in the PPG signal that may correspond to respiration for the pregnant mammal. Additionally, or alternatively, ventilatory/respiratory signal source 180 may provide a respiratory signal that corresponds to a frequency with which gas (e.g., air, anesthetic, etc.) is provided to the pregnant mammal during, for example, a surgical procedure. This respiratory signal may be used to, for example, determine a frequency of respiration for the pregnant mammal.

In some embodiments, system 100 may include a timestamping device 185. Timestamping device 185 may be configured to timestamp a signal provided by, for example, fetal probe 115, Doppler/ultrasound probe 135, pulse oximetry probe 130, NIRS adult hemoglobin probe, uterine contraction measurement device 140, ECG 175, and/or ventilatory/respiratory signal source 180 with a timestamp that represents, for example, an event (e.g., time, or t,=0, 10, 20, etc.) and/or chronological time (e.g., date and time). Timestamping device 185 may time stamp a signal via, for example, introducing a ground signal into system 100 that may simultaneously, or nearly simultaneously, interrupt or otherwise introduce a stamp or other indicator into a signal generated by one or more of, for example, fetal probe 115, Doppler/ultrasound probe 135, pulse oximetry probe 130, NIRS adult hemoglobin probe, uterine contraction measurement device 140, ECG 175, and/or ventilatory/respiratory signal source 180. Additionally, or alternatively, timestamping device 185 may time stamp a signal via, for example, introducing an optical signal into system 100 that may simultaneously, or nearly simultaneously, interrupt or otherwise introduce a stamp or other indicator into a signal generated by one or more of, for example, fetal probe 115, pulse oximetry probe 130, NIRS adult hemoglobin probe, uterine contraction measurement device 140. Additionally, or alternatively, timestamping device 185 may time stamp a signal via, for example, introducing an acoustic signal into system 100 that may simultaneously, or nearly simultaneously, interrupt or otherwise introduce a stamp or other indicator into a signal generated by one or more of, for example, fetal probe 115, Doppler/ultrasound probe 135, and/or ventilatory/respiratory signal source 180.

A timestamp generated by timestamping device 185 may serve as a simultaneous, or nearly simultaneous starting point, or benchmark, for the processing, measuring, synchronizing, correlating, and/or analyzing of a signal from, for example, fetal probe 115, Doppler/ultrasound probe 135, pulse oximetry probe 130, NIRS adult hemoglobin probe, uterine contraction measurement device 140, ECG 175, and/or ventilatory/respiratory signal source 180. In some instances, a time stamp may be used to correlate and/or synchronize two or more signals generated by, for example, fetal probe 115, Doppler/ultrasound probe 135, pulse oximetry probe 130, NIRS adult hemoglobin probe, uterine contraction measurement device 140, ECG 175, and/or ventilatory/respiratory signal source 180 so that, for example, they align in the time domain.

Figure 1B:
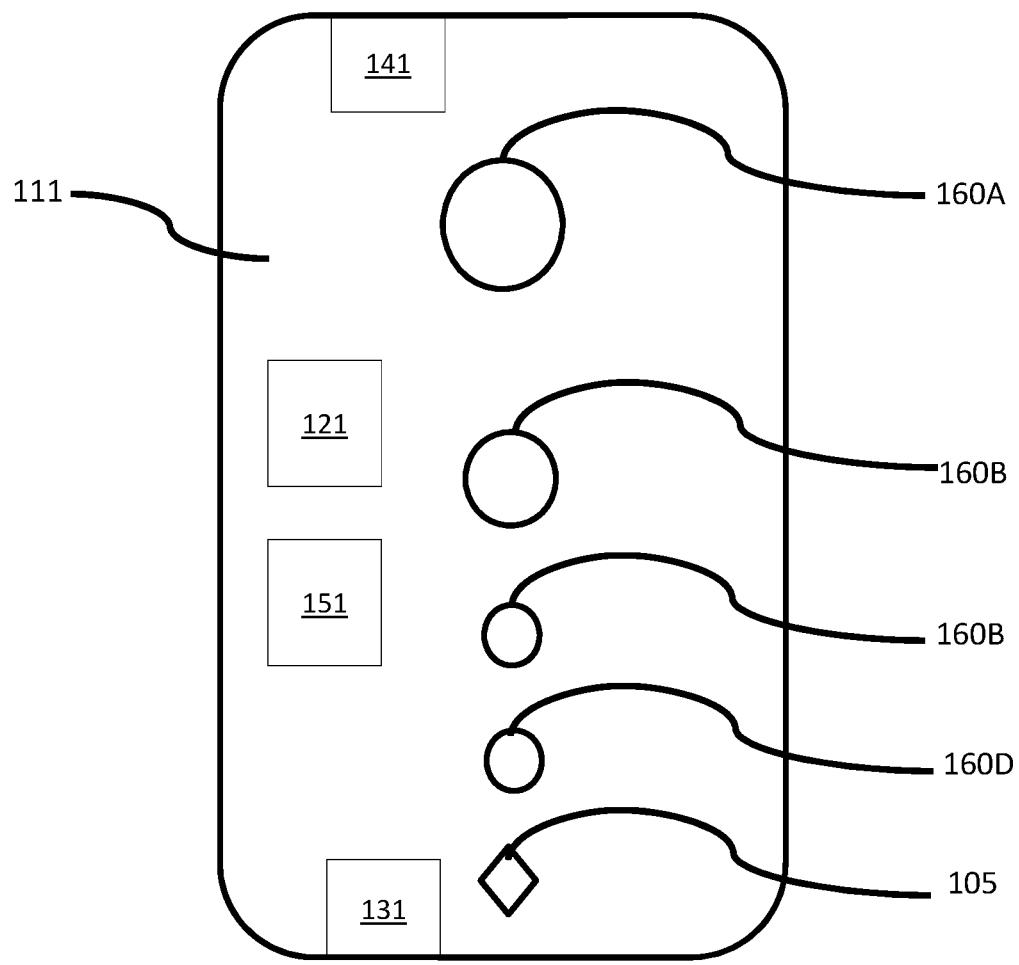
FIG. 1B is a block diagram illustrating an exemplary fetal probe, consistent with some embodiments of the present invention.

FIG. 1B is a block diagram illustrating an exemplary fetal probe 115A with housing 111 that houses a light source and a plurality of detectors arranged in an exemplary array. Housing 111 may be any housing configured to the light source and a plurality of detectors and, in some instances, may include a power source 121 (e.g., battery), a communication device (e.g., antenna), a processor 151, a power port 141, and/or a communication port 131. Exemplary fetal probe 115A includes a light source 105 substantially aligned with along the X-axis with four detectors 160A-160D. In some embodiments, the gain, or sensitivity, of a detector 160A-160D may vary with its position relative to light source 105 so that, for example, detectors positioned further away from light source 105 have a greater gain/sensitivity.

In one example, fetal probe 115A may include a light source 105 configured to emit light of a plurality of wavelengths such as 735 nm, 760 nm, 810 nm, and 850 nm and each of detectors 160A-160D may be configured to detect light/photons of each of these wavelengths. An exemplary distance between light source 105 and detector 160A is 3 cm, an exemplary distance between light source 105 and detector 160B is 5 cm, an exemplary distance between light source 105 and detector 160C is 7 cm, and an exemplary distance between light source 105 and detector 160D is 10 cm.

Figure 1C:
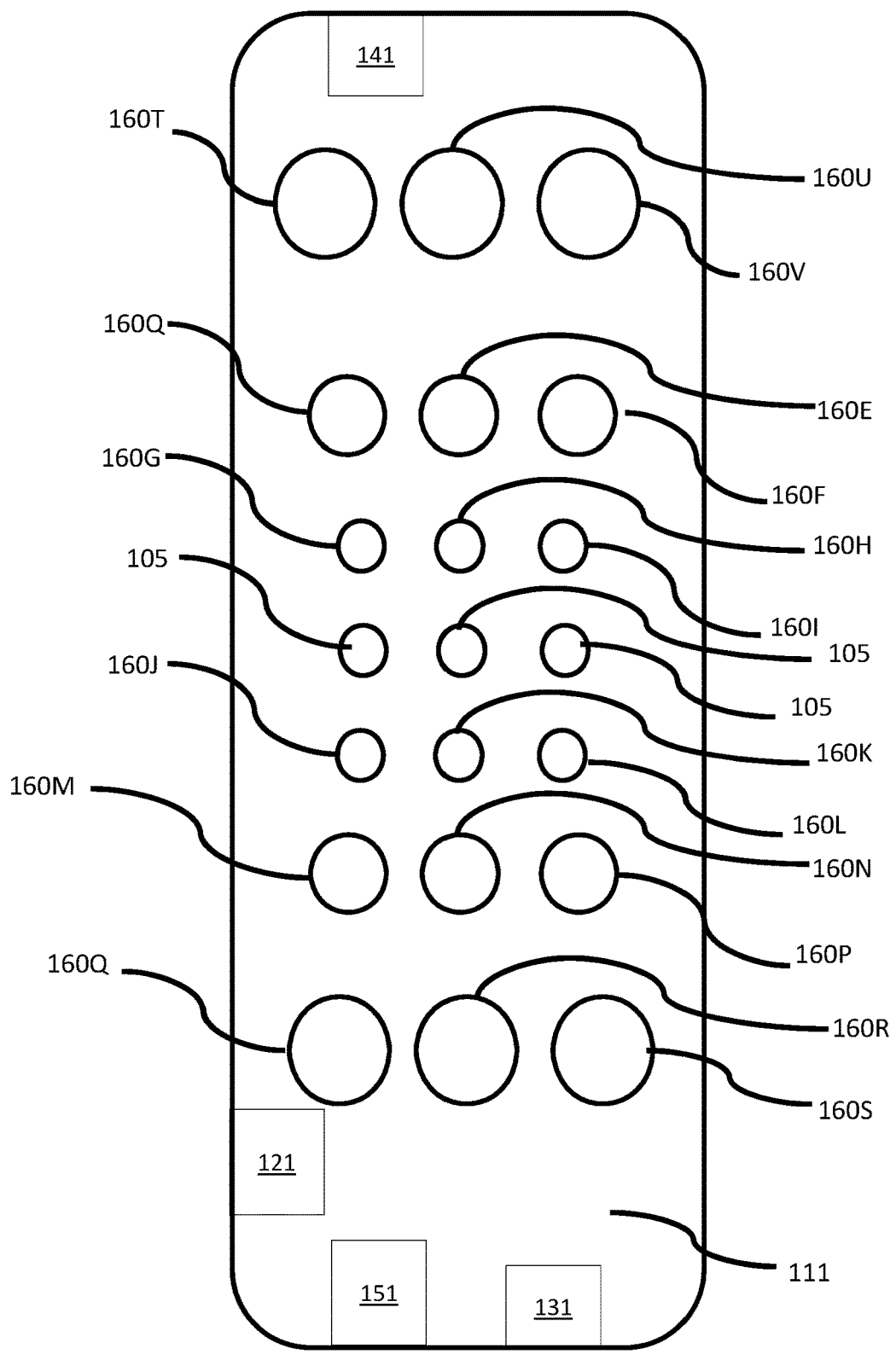
FIG. 1C is a block diagram illustrating an exemplary fetal probe, consistent with some embodiments of the present invention.

FIG. 1C is a block diagram illustrating an exemplary fetal probe 115A' with a plurality of light sources and detectors arranged in an exemplary array. Exemplary fetal probe 115A' includes a row of three light sources 105 substantially aligned with one another along the X-axis with nine detectors 160T-160Q and 160E-160I positioned above the light sources 105 in three rows with three columns and nine detectors 160J-160S positioned below the light sources 105 in three rows with three columns each. In some embodiments, the gain, or sensitivity, of a detector 160E-160S and 160T-160Q may vary with its position relative to a light source 105 so that, for example, detectors positioned further away from light source 105 have a greater gain/sensitivity.

The arrangement sources and detectors of FIGS. 1B and 1C are provided by way of example only and is not intended to limit an array of light sources 105 and/or detectors 160. Any arrangement thereof may be used to detect optical signals and convert them into the detected electronic signal(s) discussed herein.

Figure 2A:
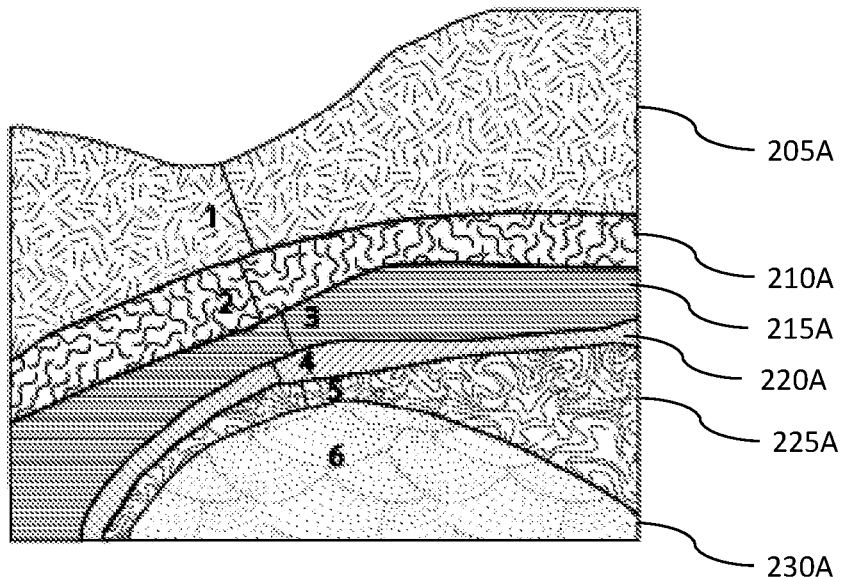
FIGS. 2A and 2B provide illustrations of exemplary dimensions for layers of tissue within two different maternal abdomens with their respective fetuses, consistent with some embodiments of the present invention.
Figure 2B:
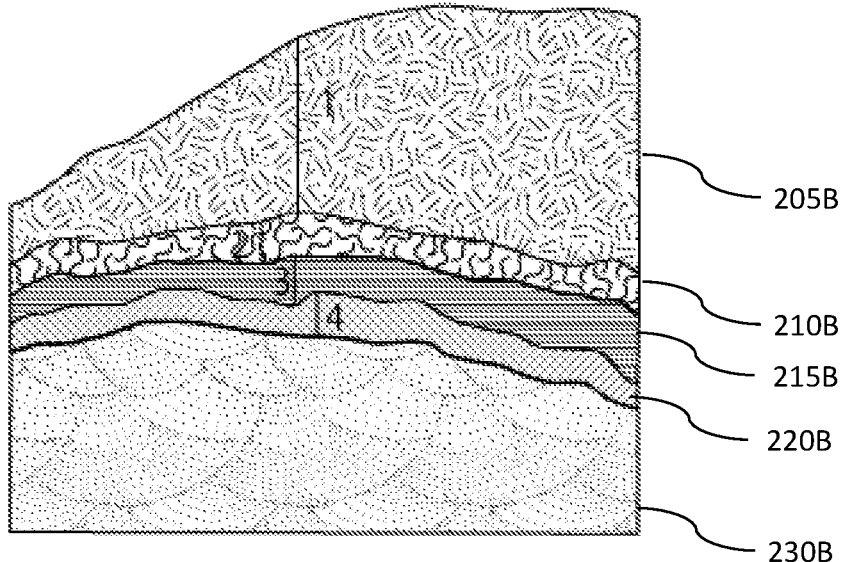

FIGS. 2A and 2B provide illustrations 201 and 202, respectively, of layers of tissue present in two different maternal abdomens with their respective fetuses included in the illustration. Information used to generate illustrations 201 and 202 may be received from, for example, ultrasound imaging devices (e.g., Doppler/ultrasound probe 135) and/or MRI images.

Illustrations 201 and 202 provide exemplary dimensions for layers of maternal tissue positioned proximate to a placement of a fetal probe 115 as well as the fetus including a depth of the fetus within the respective pregnant mammal's abdomen. A depth of a fetus may be understood as, for example, a distance between the epidermis of the pregnant mammal and the epidermis of the fetus and/or the aggregate width of the layers of maternal tissue and amniotic fluid.

Illustration 201 shows maternal abdominal tissue for a fetus that has reached 29 weeks of gestation. The layers of tissue shown in illustration 201 include a subcutaneous fat layer 205A, an abdominal muscle (skeletal muscle) layer 210A, an intraperitoneal fat layer 215A, a uterine wall (smooth muscle) layer 220A, an amniotic fluid layer 225A, and a fetus 230A. Measurements for a width of each of these layers and are taken at a position proximate to (e.g., underneath) fetal probe 115. The approximate location for where width measurements are taken is represented by a line connecting a top and bottom of the layer of interest. For example, in FIG. 2A, a width of subcutaneous fat layer 205A is represented by line 1, a width of abdominal muscle layer 210 is represented by line 2, a width of intraperitoneal fat layer 215A is represented by line 3, a width of uterine wall layer 220A is represented by line 4, and a width of amniotic fluid layer 225A is represented by line 5. Approximate dimensions for these layers of maternal tissue that are positioned proximate to (e.g., underneath) fetal probe 115 are:

Subcutaneous fat layer 205A: 10.2 mm (represented by line 1);
Abdominal muscle layer 210A: 7.1 mm (represented by line 2);
Intraperitoneal fat layer 215A: 2.0 mm (represented by line 3);
Uterine wall layer 220A: 3.1 mm (represented by line 4);
Amniotic fluid layer 225A: 3.6 mm (represented by line 5); and
Fetus 230A.

A total distance from the maternal epidermis to the epidermis of fetus 230A (i.e., fetal depth) in this example is 28 mm.

The fetus shown in illustration 202 of FIG. 2B has reached 35 weeks of gestation. The layers of tissue shown in illustration 202 include a subcutaneous fat layer 205B, an abdominal muscle (skeletal muscle) layer 210B, an intraperitoneal fat layer 215B, a uterine wall (smooth muscle) layer 220B, and a fetus 230B. Measurements for a width of each of these layers and are taken at a position proximate to (e.g., underneath) fetal probe 115. The approximate location for where width measurements are taken is represented by a line connecting a top and bottom of the layer of interest. For example, in FIG. 2B, a width of subcutaneous fat layer 205B is represented by line 1, a width of abdominal muscle layer 210 is represented by line 2, a width of intraperitoneal fat layer 215B is represented by line 3, and a width of uterine wall layer 220B is represented by line 2. Approximate dimensions for the layers of maternal tissue that are positioned proximate to (e.g., underneath) fetal probe 115 are:

Subcutaneous fat layer 205B: 11.3 mm (represented by line 1);
Abdominal muscle layer 210B: 3.1 mm (represented by line 2);
Intraperitoneal fat layer 215B: 3.1 mm (represented by line 3);
Uterine wall layer 220B: 2.3 mm (represented by line 4); and
Fetus 230B.

A total distance from maternal skin to fetus (i.e., fetal depth) in this example is 19.8 mm. Because the fetus is more developed and larger at 35 weeks of gestation, a width of the amniotic fluid is negligible and is not included in this example. In addition, for illustrations 201 and 202, a width of the skin of the pregnant mammal is also negligible at approximately 1-1.5 mm.

In some embodiments, the fetus 230A and/or fetal layer 230B may be divided into one or more additional layer(s) (not shown). These layers may pertain to, for example, one or more of vernix, hair, skin, bone, etc. In some embodiments, information regarding one or more of these layers (e.g., melanin content of fetal skin and/or hair color) may be deduced from, for example, parentage of the fetus, genetic testing of the fetus, and/or direct observation of the fetus via, for example, an optic scope and/or transvaginal examination.

Figure 3:
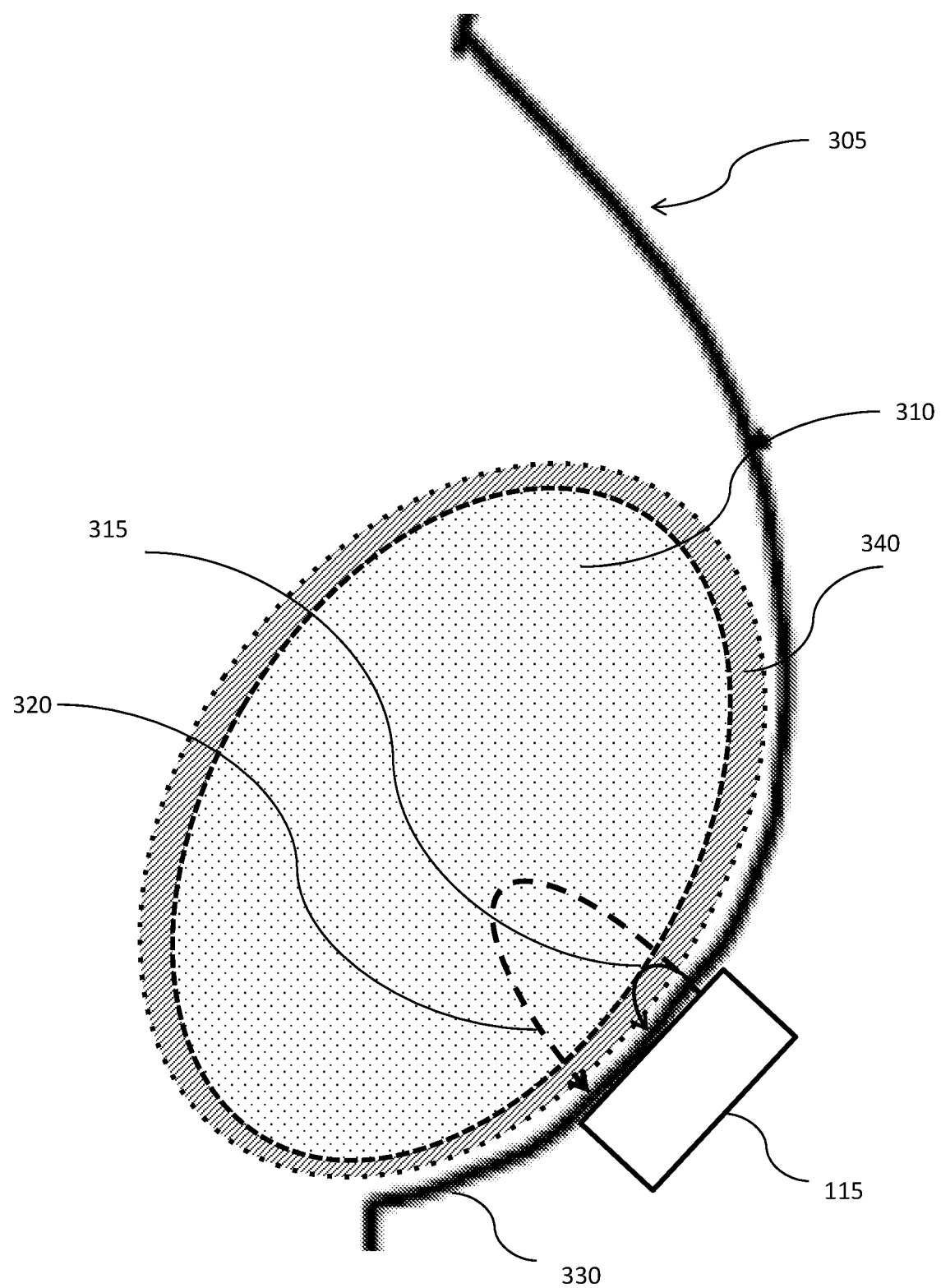
FIG. 3 provides a midsagittal plane view of pregnant mammal's abdomen with fetal probe positioned thereon, consistent with some embodiments of the present invention.

FIG. 3 illustrates provides a midsagittal plane view of pregnant mammal's 305 abdomen with fetal probe 115 positioned thereon. As shown in FIG. 3, the pregnant mammal's abdomen 305 includes an approximation of a fetus 310, a uterus 340, and maternal tissue (e.g., skin, muscle, etc.) 330. Fetal probe 115 may be positioned anywhere on the pregnant mammal's abdomen and, in some instances, more than one fetal probe 115 may be placed on the pregnant mammal's abdomen. FIG. 3 also shows a first optical signal 315 being projected into the pregnant mammal's abdomen where the depth of penetration of first optical signal 315 is only to the edge of the uterine wall 340 and then is back scattered, or transmitted through, into a detector of fetal probe 115 like detector 160. FIG. 3 further shows a second optical signal 320 being projected into the pregnant mammal's abdomen and penetrates fetus 310 prior to being detected by detector 160. First optical signal 315 and/or second optical signal 320 may include light of a single wavelength or a plurality of wavelengths that may be within, for example, the red, NIR, and/or broadband spectrum. Exemplary ranges for wavelengths included within first optical signal 315 and/or second optical signal 320 include light of 700 nm-900 nm. In some embodiments, first optical signal 315 and/or second optical signal 320 may include light of two or more distinct wavelengths or ranges of wavelengths, one red and one NIR. In some embodiments, the wavelength(s) of second optical signal 320 may be different from those of first optical signal 315. Additionally, or alternatively, first optical signal 315 and second optical signal 320 may be projected into the pregnant mammal's abdomen at different times so that second optical signal 320 may be distinguished from first optical signal 315 during processing of detected portions of first and second optical signals 315 and 320, respectively. In some embodiments, first and second optical signals 315 and 320 may include light of two distinct wavelengths or ranges of wavelengths, one red and one NIR that are slightly different from one another. For example, first optical signal 315 may include light of wavelengths within the red spectrum and second optical signal 320 may include light of wavelengths within the NIR spectrum. Additionally, or alternatively, in some embodiments, the wavelengths of first and second optical signals 315 and 320 may be selected so that any differences in their respective path lengths are small, or negligible. In some embodiments, the two or more wavelengths included in first and/or second optical signals 315 and 320 may inputs for pulse oximetry calculations using differences in absorption and/or scattering of an optical signal using, for example, the Lambert-Beer or modified Lambert-Beer equations, examples of which are discussed herein.

Figure 4:
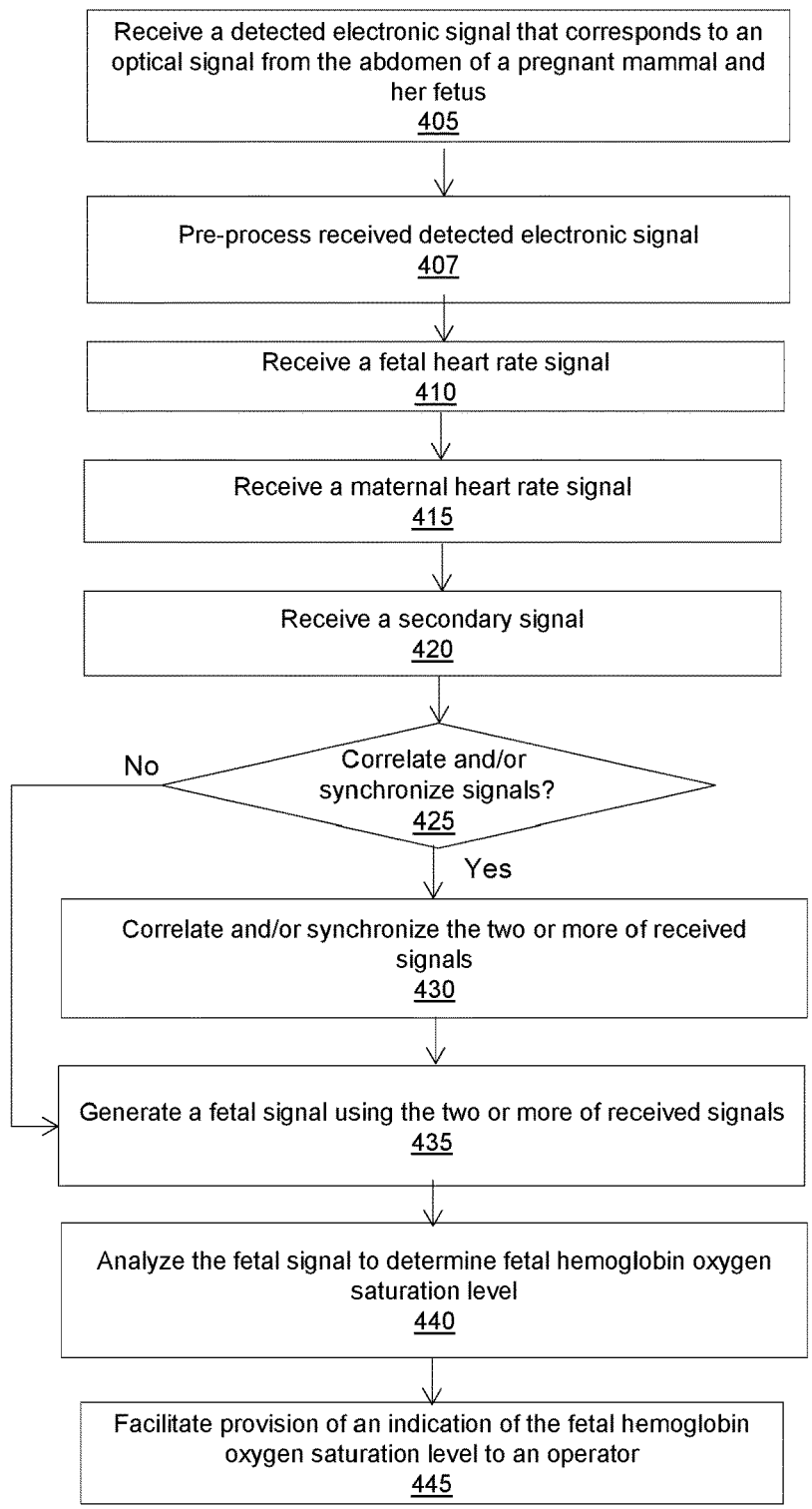
FIG. 4 is a flowchart illustrating a process for determining a level of oxygen saturation for fetal hemoglobin, in accordance with some embodiments of the present invention.

FIG. 4 is a flowchart illustrating a process 400 for non-invasively determining a level of oxygen saturation for fetal hemoglobin. Process 400 may be performed by, for example, system 100 and/or components thereof.

Initially, a detected electronic signal that corresponds to an optical signal exiting from the abdomen of a pregnant mammal and a fetus contained therein may be received (step 405) by, for example, a computer or processor such as computer 150. The optical signal may correspond to an optical signal of one or more wavelengths projected into the pregnant mammal's abdomen by, for example, one or more light sources like light source 105 and exiting therefrom via, for example, reflection, back scattering, and/or transmission (i.e., passing through the maternal abdomen). In some embodiments, the optical signal may be a broadband optical signal (e.g., white light and/or a range of, for example, 10, 15, or 20 wavelengths) and the received detected signal may correspond to an optical signal of a plurality of wavelengths. The optical signal exiting from the pregnant mammal's abdomen may be detected by a detector like detector 160 configured to convert an optical signal (in some cases a single photon) into an electronic signal, which is the detected electronic signal. At times, the detected electronic signal may include an intensity magnitude for different wavelengths of light that may correspond to the optical signal. The detector may then directly and/or indirectly communicate the detected electronic signal to a processor as may be housed in a computer such as computer 150.

The optical signal(s) that correspond to the detected electronic signal(s) may include one or more wavelengths of light generated by, for example, a light source like light source 105 and may be, for example, one or more monochromatic light source(s), one or more broadband light sources. In some embodiments, the optical signal(s) may be filtered and/or polarized. An exemplary range of wavelengths for the optical signal(s) is between 600 and 1000 nm.

Optionally, in step 407, the detected electronic signal may be pre-processed in order to, for example, remove noise from the signal and/or confounding effects of the pregnant mammal's anatomy or physiological signals on the first and/or second detected electronic signals. Execution of the pre-processing may include, but is not limited to, application of filtering techniques to the detected electronic signal, application of amplification techniques detected electronic signal, utilization of a lock-in amplifier on the detected electronic signal, and so on. When the pre-processing of step 407 includes application of a filter (e.g., bandpass or Kalman) to the detected electronic signal, the filtering may to reduce noise or hum in the detected electronic signal that may be caused by, for example, electronic noise generated by equipment generating and/or detecting the detected electronic signal and/or environmental equipment that may, in some instances, be coupled to the pregnant mammal. In some instances, the pre-processing of step 407 may include analysis of the detected electronic signals using information about the pregnant mammal's tissue and/or layers of the pregnant mammal's tissue that may be based upon, for example, ultrasound and/or MRI images, short separation analysis of the pregnant mammal, and/or double short separation analysis of the pregnant mammal to determine optical features and/or oxygenation of the maternal tissue and/or blood. Additionally, or alternatively, the detected electronic signal may be generated using diffuse optical tomography, frequency-domain spectroscopy, and/or time-domain diffuse correlation spectroscopy and use of these techniques may assist with the pre-processing of step 407.

In step 410, a fetal heart rate signal may be received from, for example, Doppler/ultra sound probe 135. In some embodiments, the fetal heart rate signal may be derived from the received detected signal. In step 415, a maternal heart rate signal may be received from, for example, pulse oximetry probe 130, NIRS adult hemoglobin probe 125, and/or a blood pressure sensing device. Optionally, a secondary signal may be received in step 420. Exemplary secondary signals include, but are not limited to, a respiratory signal for the pregnant mammal, a ventilatory signal for the pregnant mammal, an indication of whether meconium has been detected in the amniotic fluid of the pregnant mammal, a signal indicating uterine tone, a signal indicating a hemoglobin oxygen saturation level of the pregnant mammal, a pulse oximetry signal of the pregnant mammal and combinations thereof. In some embodiments, the respiratory signal may be received from a ventilation device providing air, oxygen, and/or other gasses to the pregnant mammal. Often times, this delivery of air, oxygen, and/or other gasses occurs with a periodic frequency (e.g., every 1, 2, 5 seconds) and this periodic frequency and optionally along with when, in time, the ventilation is delivered to the pregnant mammal (e.g., time=0 seconds, 2 seconds, 4 seconds, etc.) and this periodic frequency may be a secondary signal.

In step 425 it may be determined whether or not to correlate and/or synchronize the fetal heart rate signal, maternal heart rate signal, and/or secondary signal (when received). In some embodiments two or more of the received detected electronic signals, fetal heart rate signal, maternal heart rate signal, and/or secondary signal may be time-stamped with, for example, a baseline starting time (e.g., a date, time, etc. which may be associated with an absolute time (e.g., chronological time) and/or a simultaneous starting point of taking a measurement (e.g., time=0) resulting in the respective received detected electronic, maternal heart rate, fetal heart rate, and/or secondary signal. This timestamping may aid with the synchronization of step 425. In some embodiments, the timestamping may take the form of, for example, an electrical ground, an optical signal, and/or an acoustic signal that is introduced into the two or more of the received detected electronic, fetal heart rate, maternal heart rate, and/or secondary signals. In one example, an electrical ground, or other interruption (e.g., an intentionally introduced burst of optical and/or acoustic noise and/or control signal) in the operation of a device that is measuring and/or providing the received detected electronic signals, fetal heart rate signal, maternal heart rate signal, and/or secondary signal may operate as a synchronizing timestamp. This timestamp may serve to provide a synchronized point in time for signals recorded by different devices which may operate on different time scales. This synchronization may assist with alignment of two or more signals so that, for example, a heartbeat provided by maternal heart rate signal may be aligned with a simultaneously generated portion of the detected electronic signal so that, in embodiments where the maternal heart rate is used to isolate the fetal signal from the detected electronic signal, the correct portion of the detected electronic signal is aligned with the proper maternal rate signal. The signals may be timestamped by, for example, timestamping device 185.

If so, a synchronization and/or correlation process may be performed (step 430). At times, execution of step 430 may include synchronization of the signals in the time domain and/or correlation of one or more scales of measurement by which the signals are recorded.

Additionally, or alternatively, in some embodiments, the detected electronic signal, fetal heart rate signal, maternal heart rate signal, and/or secondary signal may be time stamped with a chronological time (as determined by, for example, a clock or other method of synchronizing chronological time across multiple devices). Additionally, or alternatively, in some embodiments, the detected electronic signal, fetal heart rate signal, maternal heart rate signal, and/or secondary signal may be time stamped with a relative time, which may be relative to a singular event (e.g., simultaneously starting the measurements for each of the detected electronic signal, fetal heart rate signal, maternal heart rate signal, and/or secondary signal). Additionally, or alternatively, measurement time lags or other timing features of equipment used to generate and/or communicate the detected electronic signal, fetal heart rate signal, maternal heart rate signal, and/or secondary signal may be used to synchronize, for example, a start time and/or correlate signals initially received/processed by different equipment over time.

When the signals are not to be synchronized and/or correlated or following synchronization and/or correlation, process 400 may proceed to step 435. In step 435, a fetal signal may be generated using two or more of the received signals, at least one of which may be the detected electronic signal. In some instances, execution of step 435 involves using the respiratory signal for the pregnant mammal, fetal heart rate signal, maternal heart rate signal, and/or one or more secondary signals to isolate, amplify, and/or extract, a portion of the received detected electronic signal such as the portion of the signal contributed by the fetus. When the respiratory signal for the pregnant mammal is used in step 435, it may be subtracted from and/or regressed out of the detected electronic signal via, for example, utilization of one or more linear regression equations and/or models.

Further details regarding exemplary ways step 435 may be executed are discussed herein and are provided in FIGS. 3-6. In some embodiments, execution of steps 430 and/or 435 may include execution of one or more procedures to, for example, reduce the signal-to-noise ratio or amplify a portion of the detected electronic signal corresponding to light that was incident upon the fetus. These processes include, but are not limited to, application of filters, subtraction of a known noise component, multiplication of two signals, normalization, and removal of a maternal respiratory signal. In some instances, execution of step 435 may include processing the detected electronic signal with a lock-in amplifier to amplify a preferred portion of the detected electronic signal and/or reduce noise in the detected electronic signal. The preferred portion of the signal may, in some instances, correspond to known quantities (e.g., wavelength or frequency) of the light incident on the pregnant mammal's abdomen.

In some embodiments, execution of step 435 to generate the fetal signal may include filtering the detected electronic signal using, for example, the fetal heart rate signal, the maternal heart rate signal, and/or the secondary signal. In one example, a fetal heart rate signal may be received in step 410 and correlated with the detected electronic signal in step 430. Then, a filter (e.g., bandpass and/or Kalman) that captures a range of frequencies that may correspond to, or approximate (e.g., +/−5, 10, 15, or 20%), the fetal heart rate may be applied to the detected electronic signal so that all frequencies included in the detected electronic signal that do not correspond to the fetal heart rate (or an approximation thereof) are removed from the detected electronic signal. For example, if a fetus's heart rate is 3 Hz, then the filter may be set to filter out portions of the signal above 5 Hz and below 1 Hz. In another example, if a fetus's heart rate is 3 Hz, then the filter may be set to filter out portions of the signal above 4 Hz and below 2 Hz. In another example, if a fetus's heart rate is 3 Hz, then the filter may be set to filter out portions of the signal above 3.8 Hz and below 2.2 Hz.

Additionally, or alternatively, in another example, a maternal heart rate signal may be received in step 415 and correlated with the detected electronic signal in step 430. Then, a filter that captures a range of frequencies that may correspond to, or approximate (e.g., +/−10%, 15%, or 20%), the maternal heart rate frequency may be applied to the detected electronic signal so that all frequencies included in the detected electronic signal that correspond to the maternal heart rate (or an approximation thereof) are removed from the detected electronic signal.

Additionally, or alternatively, in another example, a secondary signal in the form of a maternal respiratory and/or ventilatory signal may be received in step 415 and correlated with the detected electronic signal in step 430. Then, a filter that captures a range of frequencies that may correspond to, or approximate (e.g., +/−5, 10, 15, or 20%), the maternal respiratory and/or ventilatory frequency/signal may be applied to the detected electronic signal so that all frequencies included in the detected electronic signal that correspond to the maternal respiratory and/or ventilatory rate are removed from the detected electronic signal.

In some embodiments, the range of frequencies filtered out from the detected electronic signal may be responsive to how dynamic, or irregular, the fetal heart rate, maternal heart rate, and/or secondary signal is so that, for example, the full (or approximately full) range of fetal signal is isolated and/or the full (or approximately full) range of the maternal signal is removed. For example, if over the course of, for example, a 60 second interval the fetal heart rate, maternal heart rate, and/or secondary signal changes little, the then the band of frequencies filter for may be relatively narrow for that 60 second interval. Alternatively, in another example, if over the course of, for example, a 60 second interval the fetal heart rate, maternal heart rate, and/or secondary signal changes little, the then the band of frequencies filter for may be relatively narrow for that 60 second interval.

The fetal signal may then be analyzed to determine a fetal hemoglobin oxygen saturation level (step 440) by, for example, application of the Beer-Lambert Law to the fetal signal, application of the modified Beer-Lambert Law (see e.g., equations provided herein) to the fetal signal, and/or correlating a component (e.g., intensity, wavelength of light, etc.) of the fetal signal with a known value corresponding fetal hemoglobin oxygen saturation level value, which may, in some instances, be experimentally determined. Provision of an indication of the fetal hemoglobin oxygen saturation level value to a user (e.g., doctor, nurse, or patient) may then be facilitated (step 445) via, for example, providing the indication to a display device (e.g., display device 155), or a computer display provided by, for example, computer 150, or screen of a device (e.g., fetal probe 115).

Figure 5:
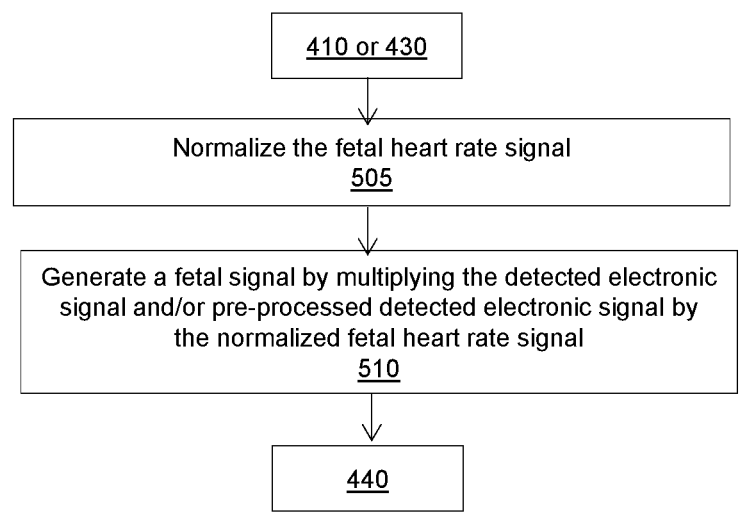
FIG. 5 is a flowchart illustrating an exemplary process for generating a fetal signal, in accordance with some embodiments of the present invention.

FIG. 5 is a flowchart illustrating an exemplary process 500 for generating a fetal signal. Process 500 may be performed by, for example, system 100 and/or components thereof.

Following execution of step 425 and/or 430, the fetal heart rate signal may be normalized (step 505) and the normalized fetal heart rate signal may then be multiplied by the detected electronic signal to generate the fetal signal (step 510). In some embodiments, the fetal signal generated in step 510 may be referred to as a "multiplied signal." In some embodiments, the normalization of step 505 may include adjusting values of one or more measurements and/or components of the detected electronic signal (e.g., intensity magnitudes for different wavelengths of light) to be on a similar, or common, scale so that the different values may be more easily evaluated/analyzed.

Figure 6:
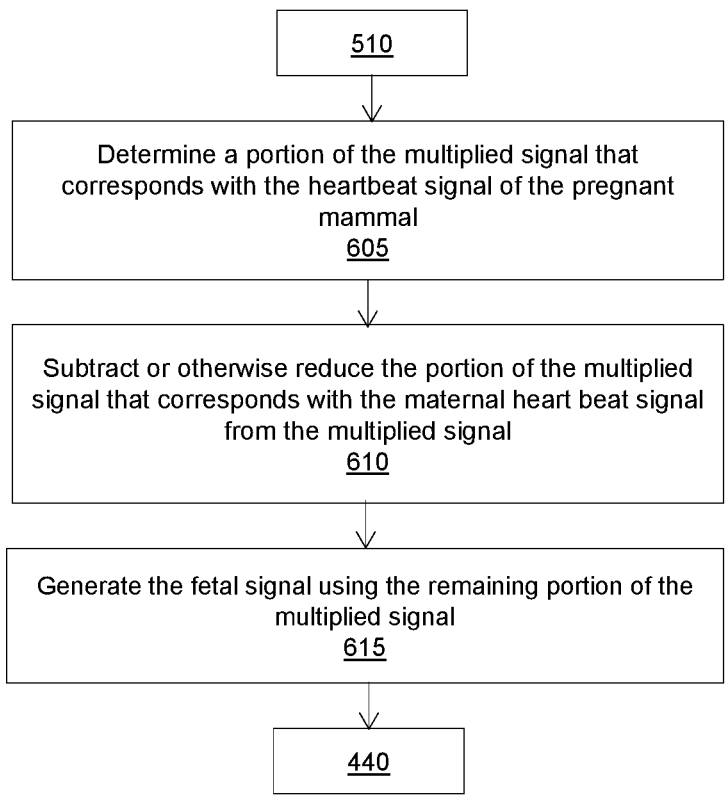
FIG. 6 is a flowchart illustrating an exemplary process for generating a fetal signal, in accordance with some embodiments of the present invention.

FIG. 6 is a flowchart illustrating an exemplary process 600 for generating a fetal signal that may be executed as part of process 500. Process 600 may be performed by, for example, system 100 and/or components thereof.

Following execution of step 510, the multiplied signal may be analyzed to determine a portion of the multiplied signal that corresponds to the heart beat signal of the pregnant mammal (step 605). At times, this analysis may include comparing the multiplied signal with the heart beat signal of the pregnant mammal. Then, the portion of the multiplied signal that corresponds to the heart beat signal of the pregnant mammal may be subtracted from, regressed out of the portion of the multiplied signal via, for example, a linear regression expression, or otherwise reduced, or removed, from the multiplied signal (step 610) and the fetal signal may be generated using the remaining portion of the multiplied signal (step 615). In some embodiments, execution of step 605 may include synchronizing and/or otherwise correlating the maternal heart rate signal with the multiplied signal and/or received detected electronic signal so that, for example, a particular maternal pulse as provided by the maternal heart rate signal is correlated in time with the multiplied signal and/or received detected electronic signal so that the correct maternal pulse is subtracted from the multiplied signal and/or received detected electronic signal. In this way, execution of process 600 does not rely on periodic maternal heart rate signal and, instead, may subtract each maternal pulsatile influence on the multiplied signal and/or received detected electronic signal on a real-time and/or pulse by pulse basis.

Figure 7:
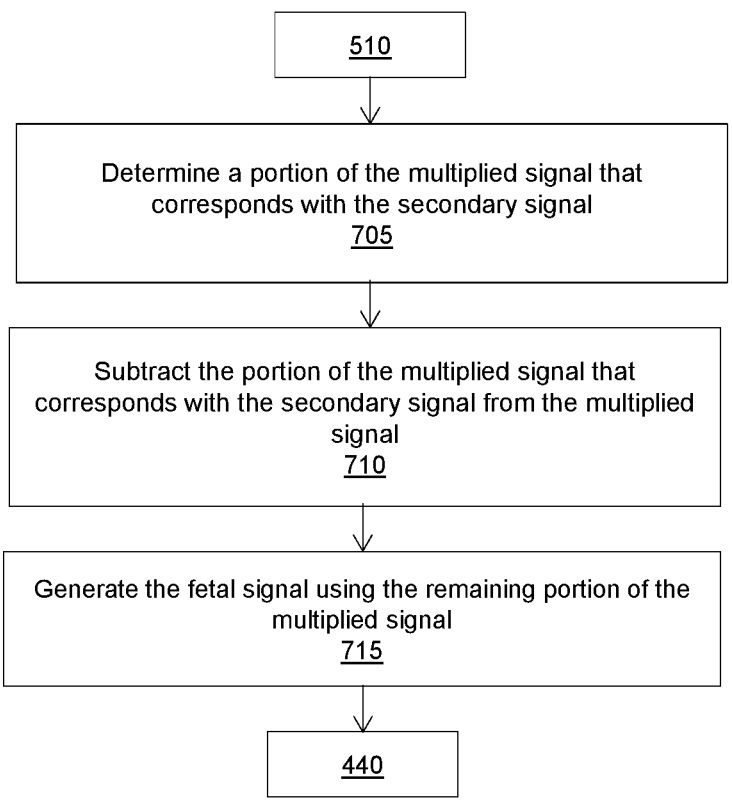
FIG. 7 is a flowchart illustrating an exemplary process for generating a fetal signal, in accordance with some embodiments of the present invention.

FIG. 7 is a flowchart illustrating a third exemplary process 700 for generating a fetal signal that may be executed as part of process 500. Process 700 may be performed by, for example, system 100 and/or components thereof.

Following execution of step 510, the multiplied signal may be analyzed to determine a portion of the multiplied signal that corresponds to the secondary signal (step 705). In some embodiments, execution of step 705 may include synchronizing and/or otherwise correlating the secondary signal with the multiplied signal and/or received detected electronic signal so that, for example, a portion of the secondary signal is correlated in time with the multiplied signal and/or received detected electronic signal so that a correct portion of the multiplied signal and/or received detected electronic signal (corresponding to the secondary signal) is subtracted from the multiplied signal and/or received detected electronic signal. In this way, execution of process 700 does not rely on periodic secondary signals and, instead, may subtract, or regress out via, for example, a linear regression expression, each variation of the secondary signal from the multiplied signal and/or received detected electronic signal on a real-time.

Then, in step 710, the portion of the multiplied signal that corresponds to the secondary signal may be subtracted, or otherwise removed, from the multiplied signal. When multiple secondary signals are under consideration, steps 705 and 710 may be executed for each of the secondary signals and the fetal signal may be generated using the remaining portion of the multiplied signal (step 715).

Figure 8:
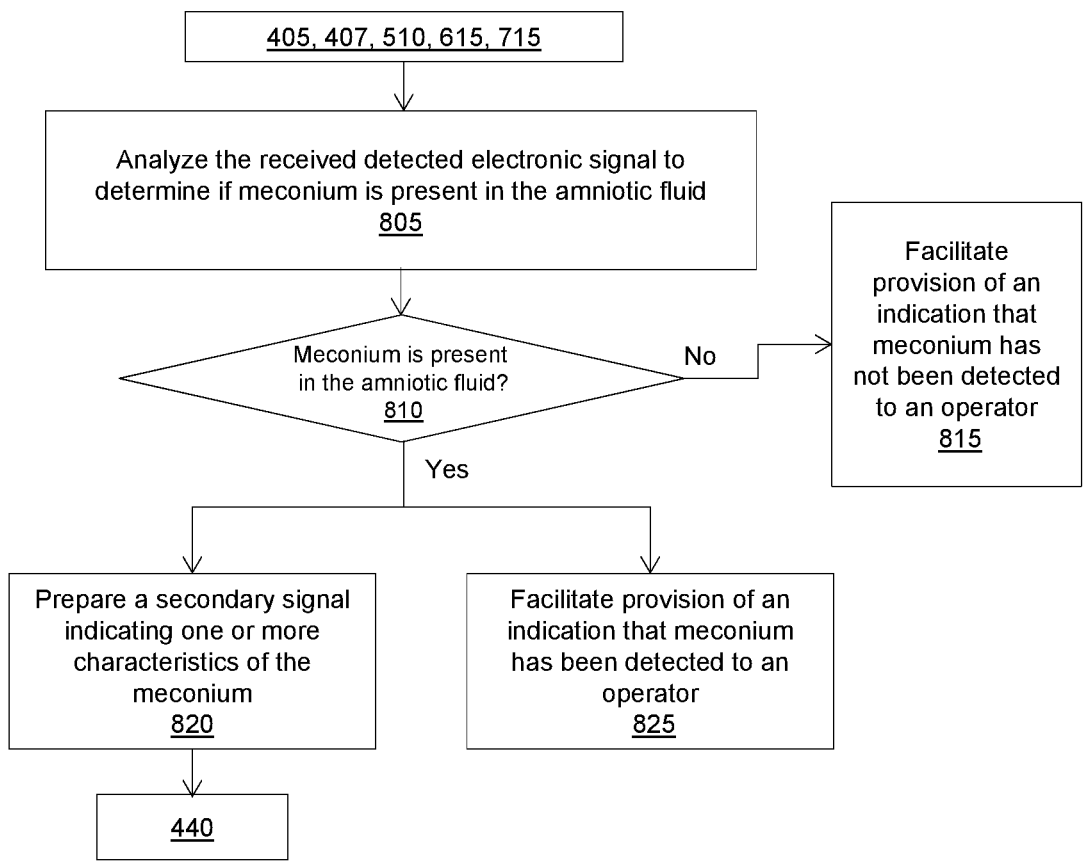
FIG. 8 is a flowchart illustrating an exemplary process for generating a fetal signal and/or determining whether meconium is present in the amniotic fluid of a pregnant mammal, in accordance with some embodiments of the present invention.

FIG. 8 is a flowchart illustrating an exemplary process 800 for generating a fetal signal and/or determining whether meconium is present in the amniotic fluid of a pregnant mammal. Process 800 may be performed by, for example, system 100 and/or components thereof.

Initially, a detected electronic signal of step(s) 405, 407, 510, 615, and/or 715 may be received. The detected electronic signal may then be analyzed to determine whether meconium is present in the amniotic fluid of the pregnant mammal (step 805). This analysis may include, but may not be limited to, determining a wavelength and/or frequency of light incident upon and/or reflected by the pregnant mammal and/or her amniotic fluid and/or an intensity of the exiting light. In some instances, the analysis may include comparatively analyzing the intensity of different wavelengths and/or frequencies of light exiting the pregnant mammal and/or her amniotic fluid.

In some instances, a wavelength and/or range of wavelengths of light corresponding to the detected electronic signal of step (s) 405, 407, 510, 615, and/or 715 may have absorption and/or scattering characteristics that indicate the presence of meconium and the second optical signal may be of a reference wavelength and/or range of wavelengths. For example, it is known that light of 415 nm is absorbed by meconium so, the detected electronic signal corresponds to a wavelength of light that includes 415 nm only or a range of wavelengths (e.g., 400-430 nm) that includes 415 nm.

Following the analysis of step 805, it may be determined whether meconium is present in the amniotic fluid (step 810). In some embodiments, this determination may be facilitated by comparing the results of the analysis with known values for light wavelength/frequency intensity when meconium is, and is not, present within the amniotic fluid. For example, it is known that meconium absorbs light of 415 nm and the detected electronic signal may be analyzed to determine how much light of 415 nm has be absorbed and/or detected.

When meconium is not detected, provision of an indication that meconium has not been detected to a user may be facilitated via, for example, communicating the indication to a display device (e.g., display device 155) (step 815). When meconium is detected, a secondary signal indicating that the meconium has been detected may be prepared and communicated to, for example, a processor executing process 400 (which may be, in some instances, the processor executing process 800) for receipt in step 440. Additionally, or alternatively, when meconium is detected, provision of an indication that meconium has been detected to a user may be facilitated via, for example, communicating the indication to a display device (e.g., display device 155) (step 825). At times, the secondary signal of step 820 and/or the indication of steps 825 may provide information regarding, for example, an amount of meconium detected and/or a characteristic (e.g., color) thereof. This secondary signal may be used as, for example, a filter for the detected electronic signal when generating the fetal signal.

In some embodiments, two or more of the processes herein described may be performed together, in any order, to generate the fetal signal and/or determine a level of oxygen saturation for fetal hemoglobin.

Figure 9:
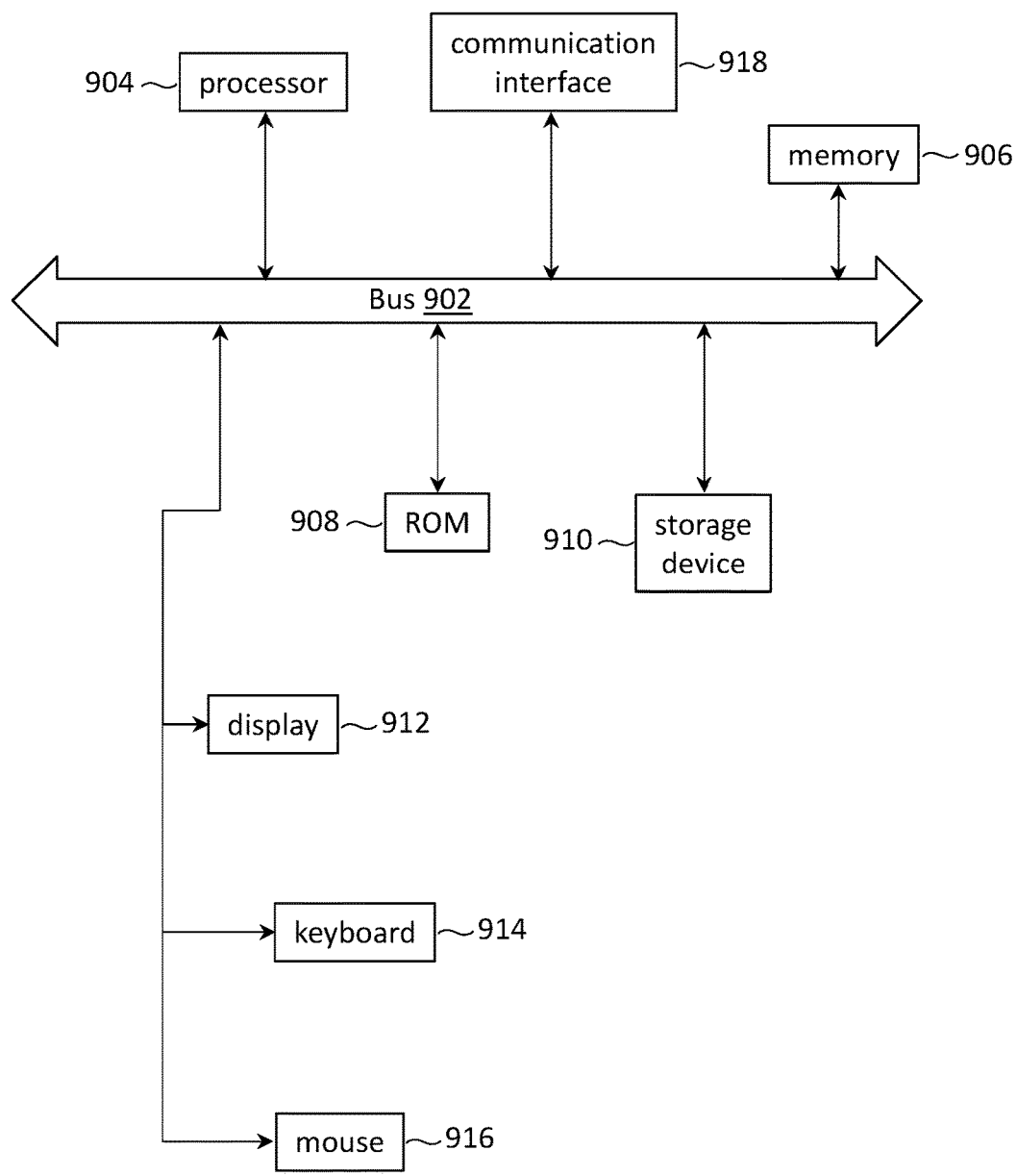
FIG. 9 is a block diagram of an exemplary processor-based system that may store data and/or execute instructions for the processes disclosed herein, consistent with some embodiments of the present invention.

FIG. 9 provides an example of a processor-based system 900 that may store and/or execute instructions for the processes described herein. Processor-based system 900 may be representative of, for example, computing device 1450 and/or the components of housing 125 and/or 605. Note, not all of the various processor-based systems which may be employed in accordance with embodiments of the present invention have all of the features of system 900. For example, certain processor-based systems may not include a display inasmuch as the display function may be provided by a client computer communicatively coupled to the processor-based system or a display function may be unnecessary. Such details are not critical to the present invention.

System 900 includes a bus 902 or other communication mechanism for communicating information, and a processor 904 coupled with the bus 902 for processing information. System 900 also includes a main memory 906, such as a random-access memory (RAM) or other dynamic storage device, coupled to the bus 902 for storing information and instructions to be executed by processor 904. Main memory 906 also may be used for storing temporary variables or other intermediate information during execution of instructions to be executed by processor 904. System 900 further includes a read only memory (ROM) 908 or other static storage device coupled to the bus 902 for storing static information and instructions for the processor 904. A storage device 910, which may be one or more of a flexible disk, a hard disk, flash memory-based storage medium, magnetic tape or other magnetic storage medium, a compact disk (CD)-ROM, a digital versatile disk (DVD)-ROM, or other optical storage medium, or any other storage medium from which processor 904 can read, is provided and coupled to the bus 902 for storing information and instructions (e.g., operating systems, applications programs and the like).

System 900 may be coupled via the bus 902 to a display 912, such as a flat panel display, for displaying information to a user. An input device 914, such as a keyboard including alphanumeric and other keys, may be coupled to the bus 902 for communicating information and command selections to the processor 904. Another type of user input device is cursor control device 916, such as a mouse, a trackball, or cursor direction keys for communicating direction information and command selections to processor 904 and for controlling cursor movement on the display 912. Other user interface devices, such as microphones, speakers, etc. are not shown in detail but may be involved with the receipt of user input and/or presentation of output.

The processes referred to herein may be implemented by processor 904 executing appropriate sequences of processor-readable instructions stored in main memory 906. Such instructions may be read into main memory 906 from another processor-readable medium, such as storage device 910, and execution of the sequences of instructions contained in the main memory 906 causes the processor 904 to perform the associated actions. In alternative embodiments, hard-wired circuitry or firmware-controlled processing units (e.g., field programmable gate arrays) may be used in place of or in combination with processor 904 and its associated computer software instructions to implement the invention. The processor-readable instructions may be rendered in any computer language.

System 900 may also include a communication interface 918 coupled to the bus 902. Communication interface 918 may provide a two-way data communication channel with a computer network, which provides connectivity to the plasma processing systems discussed above. For example, communication interface 918 may be a local area network (LAN) card to provide a data communication connection to a compatible LAN, which itself is communicatively coupled to other computer systems. The precise details of such communication paths are not critical to the present invention. What is important is that system 900 can send and receive messages and data through the communication interface 918 and in that way communicate with other controllers, etc.

For the embodiments herein described, the light directed into the pregnant mammal's abdomen and the fetus may be of at least two separate wavelengths and/or frequencies (e.g., red, infrared, near-infrared, etc.) and the received detected electronic signals may correspond to light of these different wavelengths.

Hence, systems, devices, and methods for determining fetal oxygen level have been herein disclosed. In some embodiments, use of the systems, devices, and methods described herein may be particularly useful during the labor and delivery of the fetus (e.g., during the first and/or second stage of labor) because it is difficult to assess fetal health during the labor and delivery process.

Figure 10:
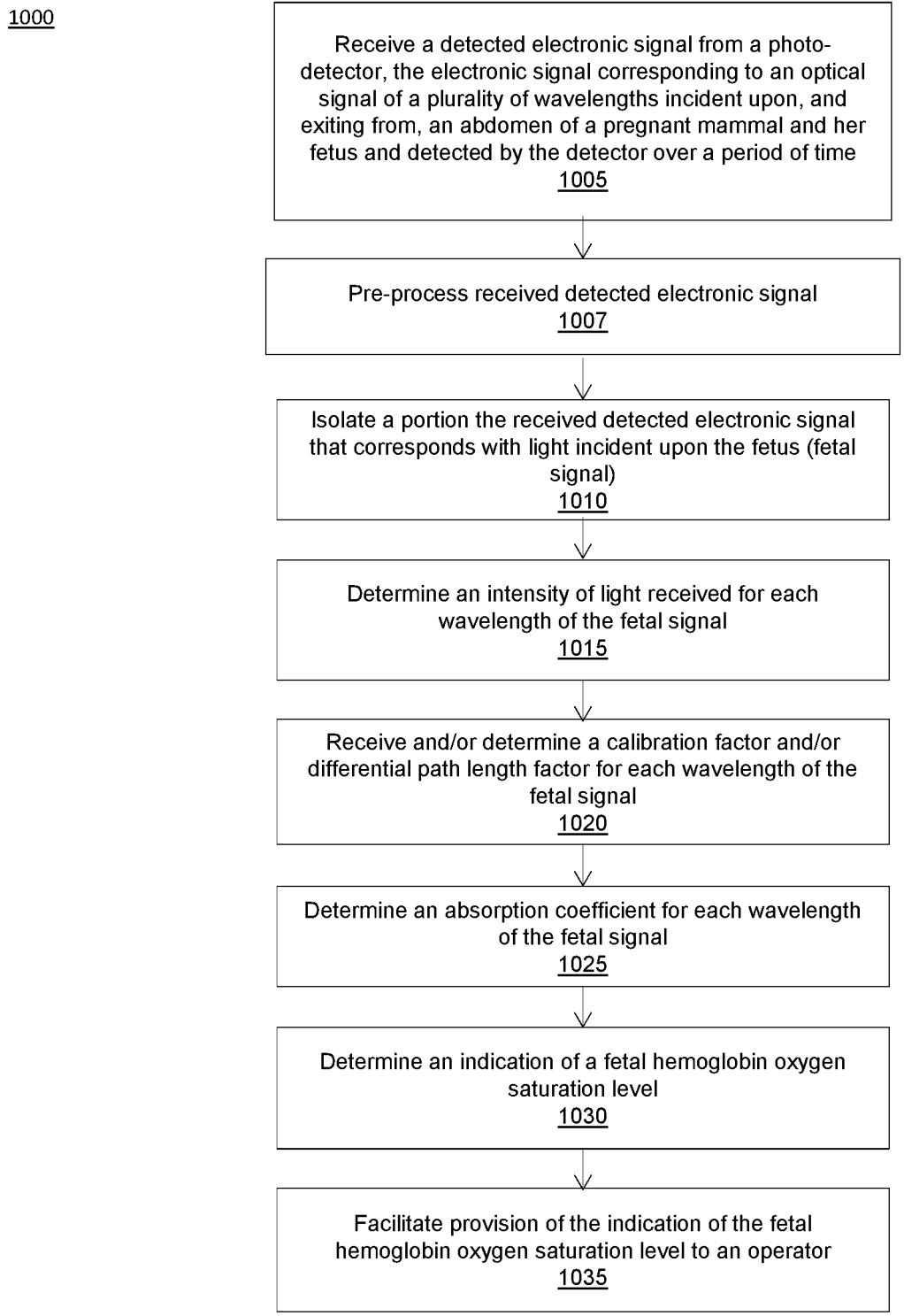
FIG. 10 is a flowchart illustrating an exemplary process for, determining a fetal hemoglobin oxygen saturation level, consistent with some embodiments of the present invention.

FIG. 10 provides a flowchart illustrating an exemplary process 1000 for determining a fetal hemoglobin oxygen saturation level using broad spectrum light. Process 1000 may be executed by, for example, system 100 and/or a component thereof.

Initially, in step 1005, a detected electronic signal may be received from a photo-detector, like detector 160. The detected electronic signal may correspond to an optical signal of a plurality of wavelengths (e.g., a broad spectrum of wavelengths) incident upon, and exiting from, an abdomen of a pregnant mammal and her fetus that has been detected by the detector over a period of time. Detection of the optical signal may include counting photons of different wavelengths that are received by the detector and/or are incident on optical fibers coupled to the detector. On some occasions, the received detected electronic signals may resemble the detected electronic signals received in step 405 of process 400 discussed above.

Optionally, in step 1007, the detected electronic signal may be pre-processed in order to, for example, remove noise and/or amplify a desired portion of the detected electronic signal(s). This pre-processing may be similar to the pre-processing executed in step 407 of process 400 and discussed above with regard to FIG. 4.

In step 1010, a portion of the detected electronic signal of step 1005 and/or pre-processed signal of step 1007 that has been incident upon the fetus may be isolated from the detected electronic signal received in step 1005. This isolated portion of the received detected electronic signal may be referred to herein as a fetal signal. Step 1010 may be executed using any appropriate method of isolating the fetal signal from the detected electronic signal. Appropriate methods include, but are not limited to, reducing noise in the signal via, for example, application of filtering or amplification techniques, determining a portion of the detected electronic signal that is contributed by the pregnant mammal and then subtracting, or otherwise removing, that portion of the detected electronic signal from the received detected electronic signals and/or receiving information regarding fetal a heart rate and using that information to lock in (via, for example, a lock-in amplifier) on a portion of the received detected electronic signals generated by the fetus. In some embodiments, the fetal signal may be generated via execution of, for example, process(es) 400, 500, 600, 700, and/or 800 discussed above with regard to FIGS. 4, 5, 6, 7, 8, respectively.

An intensity of light for each wavelength of the optical signal included in the fetal signal may then be determined (step 1015). At times, the intensity may be determined by counting each photon of each wavelength that is received over a period of time. In some embodiments, execution of step 1015 may include processing the fetal signal using, for example, a continuous wave photon migration model.

In step 1020, a calibration factor and/or a differential path length factor (DPF) may be determined for each wavelength of light included in the fetal signal. In some embodiments, the calibration factor may be empirically determined based on experimental data. In some instances, empirically determining the calibration factor may involve fitting intensity data for the detected electronic signal to, for example, a curve or other value to extract DFP over wavelength. In some instances, the DPF may be derived from an empirically based model designed to compensate for diffusion path length factor differences of different wavelengths of light. In some embodiments, the empirically based model may be guided by simulations of how (e.g., absorption and scattering) light travels through layers of maternal and/or fetal tissue. In some instances, the empirically based model may be informed by structural models of the maternal abdomen, fetus, and/or tissue layers that may include one or more approximations (e.g., depth, density, etc.) and/or optical properties (e.g., absorption and/or scattering) that are derived using the structural model. In some instances, (e.g., prior to execution of step 1020) a range of values for the empirically based model may be simulated or tested to see what their respective impact is on determining the path length factor and/or correcting for the spectral dependence of the path length. These simulations and/or tests may be informed by, for example, ultrasound and/or MRI imaging of a subject pregnant mammal and/or a group of pregnant mammals, which may use images like those provided in FIGS. 2A and 2B and/or short separation analysis techniques like those described herein with regard to processes 1100 and 1200.

Then, an absorption coefficient for each wavelength of the fetal signal may be determined (step 1025) via, for example, calculations using, executing the modified Beer-Lambert law, which is presented as Equation 1 below, for each wavelength.

$$\Delta\mu_a(\lambda) = -\frac{1}{r*DPF(\lambda)}\frac{\Delta I(\lambda)}{I_0} \quad \text{Equation 1}$$

where:
$\Delta\mu_a(\lambda)$=the change in the absorption coefficient for a given wavelength $\lambda$ over a defined time period;
r=a distance between the light source and detector;
DPF=the differential path length factor for the given wavelength $\lambda$;
$I_0$=the intensity of emitted light of the given wavelength $\lambda$ (e.g., the number of photons emitted by the broadband light source) and time (t)=0; and
$\Delta I(\lambda)$=the change in the measured light intensity of detected light (e.g., the number of photons detected by the detector) for the given wavelength A over the defined time period.

Next, an indication of fetal hemoglobin oxygen saturation may be determined (step 1030) via, for example, calculations using Equation 2, provided below:

$$\Delta\mu_a(\lambda)=\Delta c_{HbO}*\varepsilon_{HbO}(\lambda)+\Delta c_{Hb}*\varepsilon_{Hb}(\lambda) \quad \text{Equation 2}$$

where:
$\Delta\mu_a(\lambda)$=the change in the absorption coefficient for a given wavelength A over a defined time period;
$\Delta c_{HbO}$=a change in the concentration of oxygenated hemoglobin (HbO) over the defined time period;
$\Delta c_{Hb}$=a change in the concentration of deoxygenated hemoglobin (Hb) over the defined time period;
$\varepsilon_{HbO}(\lambda)$=the extinction coefficient for oxygenated hemoglobin (HbO) for the given wavelength; and
$\varepsilon_{Hb}(\lambda)$=the extinction coefficient for deoxygenated hemoglobin (Hb) for the given wavelength.

Equation 1 may be solved for two or more wavelength pairs by inputting the change in intensity, as a function of wavelength, $\lambda$. From this, changes in absorption coefficients may be determined using Equation 2, $\Delta\mu_a$, and inputting known extinction coefficients, $\varepsilon_{HbO}(\lambda)$ and $\varepsilon_{Hb}(\lambda)$ for a particular wavelength, which may be looked up in, for example, a look-up table stored on, for example, computer 150. The wavelength pairs used to perform the calculations of Equation 2 may be any pair of wavelengths included in the spectrum of wavelengths of the optical signal incident upon the pregnant mammal's abdomen. In some embodiments, the calculation of Equation 2 may be performed many times (e.g., 10s, 100s, or 1000s), in different combinations of wavelengths, in order to arrive at multiple values for $\Delta c_{HbO}$ and $\Delta c_{Hb}$ which may be weighted and/or averaged according to one or more criteria to arrive at robust values (e.g., statistically valid and/or with an acceptable level of confidence and error rate) for $\Delta c_{HbO}$ and $\Delta c_{Hb}$. Additionally, or alternatively, the calculation of Equation 2 may be performed many times (e.g., 10s, 100s, or 1000s), to fit a plurality of wavelengths at the same time to the equation.

The values for $\Delta c_{HbO}$ and $\Delta c_{Hb}$ generated via Equation 2 are relative values, not absolute values, for the concentrations of oxygenated and deoxygenated hemoglobin in the fetus's blood, which may be useful in monitoring the fetal hemoglobin oxygen saturation levels of the fetus over time. In some embodiments, the determination of step 1030 may also include determining an overall oxygen saturation for the fetus's hemoglobin by determining a ratio of the change in concentration of oxygenated hemoglobin to the change in concentration of total hemoglobin, which may be the sum of oxygenated and deoxygenated hemoglobin.

Figure 11:
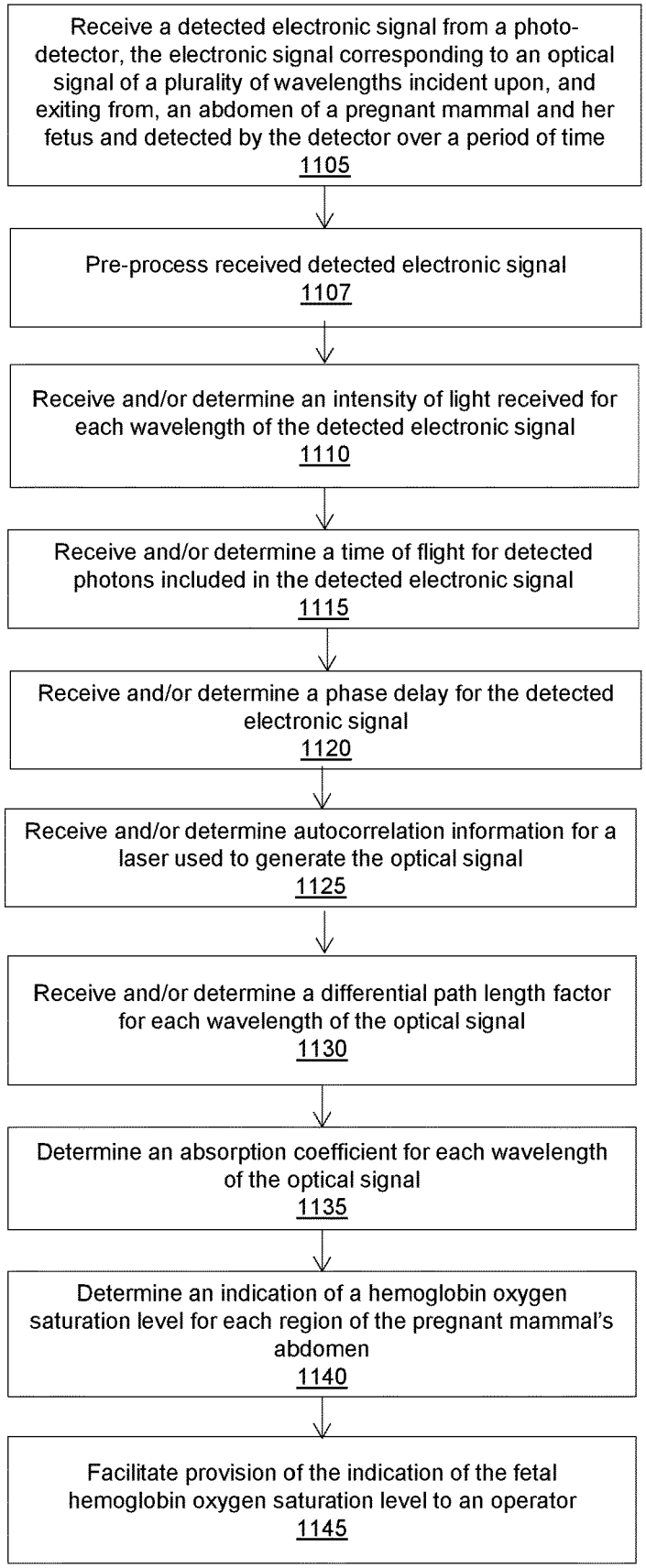
FIG. 11 is a flowchart illustrating an exemplary process for determining a fetal hemoglobin oxygen saturation level, consistent with some embodiments of the present invention.

FIG. 11 provides a flowchart illustrating an exemplary process 1100 for determining a fetal hemoglobin oxygen saturation level using broad spectrum light. In some embodiments, process 1100 may be executed to generate a two-and/or three-dimensional map of the hemoglobin saturation of a pregnant mammal's abdomen may be generated using a broad spectrum of light. Process 1100 may be executed by, for example, system 100 and/or a component thereof.

In step 1105, a detected electronic signal may be received from a photo-detector, like detector 160. The detected electronic signal may correspond to an optical signal of a plurality of wavelengths (e.g., 4, 8, 20, or a broad spectrum of wavelengths) incident upon, and exiting from, an abdomen of a pregnant mammal and her fetus that have been detected by the detector over a period of time. Detection of the optical signal may include counting photons of different wavelengths that are received by the detector and/or are incident on optical fibers coupled to the detector like detector 160. On some occasions, the received detected electronic signal may resemble the detected electronic signals received in step 405 of process 400 discussed above.

Optionally, in step 1107, the first and/or second detected electronic signal(s) may be pre-processed in order to, for example, remove noise and/or amplify a desired portion of the respective first and/or second detected electronic signal(s). This pre-processing may be similar to the pre-processing executed in step 407 of process 400 and discussed above with regard to FIG. 4.

The received detected electronic signal may include information regarding a position (e.g., x-, y-, and/or z-components) for where a portion of the signal is detected (e.g., where a particular photon is detected) on the pregnant mammal's abdomen and/or a trajectory of a photon or beam of photons that may, in some cases, include a time measurement. Additionally, or alternatively, position information for the received detected electronic signal and/or a portion thereof (e.g., a photon or an intensity of a particular wavelength) may be determined mathematically via, for example, geometrical or probabilistic determinations. In some embodiments, the pregnant mammal's abdomen and/or a portion of it (e.g., a cross section or a region where the fetus is located) may be divided into regions of a particular dimension (e.g., 2 $mm^2$, 5 $mm^2$, 10 $mm^2$, 2 $mm^3$, 5 $mm^3$, 10 mm³, etc.) that may be represented and/or reconstructed as, for example, pixels in an image. Additionally, or alternatively, the detected electronic signal may be detected by the photo-detector via a scanning operation (e.g., raster scanning) of an area so that a position for each counted photon and/or an intensity of a detected signal of one or more wavelength(s) of light may be detected, determined, and/or recorded.

Optionally, an intensity of light for each wavelength of the detected electronic signal and/or pre-processed detected electronic signal may be determined for each region of the maternal abdomen (step 1110). In some instances, the intensity may be determined by counting each photon of each wavelength that is associated with a particular region of the pregnant mammal's abdomen over a period of time. In some embodiments, execution of step 1110 may include processing the fetal signal using, for example, a continuous wave photon migration model. At times, execution of step 1110 may include determining a position for a portion (e.g., a photon or group of photons of a given wavelength) of the received detected electronic signal using, for example, information regarding where or when the portion of the detected electronic signal is received.

Additionally, or alternatively, a time of flight for detected photons included in the detected electronic signal may be received and/or determined (step 1115). In some cases, the time of flight for detected photons may be specific to a wavelength (or range of wavelengths) of detected photon.

Additionally, or alternatively, a phase delay of the detected electronic signal and/or optical signal corresponding to the detected electronic signal may be received and/or determined (step 1120) when, for example, process 1100 and/or a portion thereof is using frequency domain analysis. In some cases, the phase delay may be specific to a wavelength (or range of wavelengths) of a detected photon.

Additionally, or alternatively, autocorrelation information for a laser being used to generate the optical signal delivered to the pregnant mammal's abdomen that corresponds to the detected electronic signal may be received and/or determined (step 1125).

In step 1130, a differential path length factor (DPF) may be determined for each wavelength of light included in the detected electronic signal. At times, step 1130 may be executed in a manner similar to the execution of step 1020. In some instances, this determination may be regional (i.e., determined for each region and/or layer of the pregnant mammal's abdomen) using, for example, physiological and/or anatomical characteristics of the pregnant mammal's abdomen.

Then, an absorption coefficient for each wavelength of the fetal signal may be determined for each region of the pregnant mammal's abdomen (step 1135). At times, step 1135 may be executed in a manner similar to the execution of step 1025 and Equation 1 may be used to determine the absorption coefficients for step 1135. In some embodiments, execution of steps 1130 and/or 1135 may use the intensity, time of flight, phase delay and/or laser autocorrelation information received and/or determined in steps 1110-1125, respectively.

Next, an indication of hemoglobin oxygen saturation level may be determined for each region of the pregnant mammal's abdomen (step 1140). Step 1140 may be executed in a manner similar to step 1045 and Equation 2 may be used to determine the indication of hemoglobin oxygen saturation level for each region of the pregnant mammal's abdomen.

Then, an indication of the fetal hemoglobin oxygen saturation may be provided to a user via, for example, display on display device 155 (step 1145). In some instances, the indication of fetal hemoglobin oxygen saturation may be provided/displayed as a two- and/or three-dimensional map of the determined hemoglobin oxygen saturation level for each region of the pregnant mammal's abdomen. This two- and/or three-dimensional map may, in some instances, be generated by mapping each hemoglobin oxygen saturation level with its respective region of the pregnant mammal's abdomen so that different regions of hemoglobin oxygen saturation within the pregnant mammal's abdomen are visually displayed via, for example, color coding and/or grey scale. When the user views the map, he or she may be able to determine the fetal hemoglobin oxygen saturation by looking at the region of the map that corresponds with the fetus's position as known through, for example, ultrasound and/or MRI determinations.

FIG. 12 is a flowchart illustrating a process 1200 for determining an individualized ratio of ratios (R) value for a pulse oximeter that may be used to performed transabdominal fetal pulse oximetry. Process 1200 may be performed by, for example, system 100 or components therein.

Initially, a first detected electronic signal that corresponds to an optical signal of a first wavelength, or first range of wavelengths, exiting from the abdomen of a pregnant mammal and a fetus contained therein may be received by, for example, a computer or processor such as computer 150 (step 1205). In step 1210, a second detected electronic signal that corresponds to an optical signal of a second wavelength, or second range of wavelengths, exiting from the abdomen of a pregnant mammal and a fetus contained therein may be received by, for example, the computer or processor. The first and second detected electronic signals may be communicated directly, or indirectly, to the computer by/from a detector, like detector 160, that has received an optical signal and converted the optical signal into an electronic signal.

The first and second optical signals may be incident upon and/or directed into the pregnant mammal's abdomen by one or more light sources like light source 105. In many instances, the first and second optical signals may have similar wavelengths and may be within the same band of the electromagnetic spectrum. For example, both the first and second optical signals may be within the red, NIR, or infrared bands of the electromagnetic spectrum. In many instances, the wavelengths of the first and second optical signals may be chosen so that a path length of the respective first and second optical signals may be the same or sufficiently close to one another to be mathematically insignificant. For example, a first optical signal may be 790 nm and a second optical signal may be 805 nm or a first optical signal may be 780 nm and a second optical signal may be 800 nm. In another example, a first optical signal may be 810 nm and a second optical signal may be 825 nm or a first optical signal may be 820 nm and a second optical signal may be 833 nm. In many instances, the light sources used to generate the first and second optical signal may be light source(s) capable of generating mono-chromatic light and/or light within a narrow band of wavelengths such as a laser or LED. In some embodiments, the received detected electronic signals may resemble the detected electronic signals received in step 405 of process 400 discussed above. In some embodiments, process 1200 may be executed with many (e.g., 4, 5, 10, 15, 40, 400, broadband or white light, etc.) different optical signals and/or corresponding detected electronic signals.

Optionally, in step 1212, the first and/or second detected electronic signal(s) may be pre-processed in order to, for example, remove noise and/or amplify a desired portion of the respective first and/or second detected electronic signal(s). This pre-processing may be similar to the pre-processing executed in step 407 of process 400 and discussed above with regard to FIG. 4. Additionally, or alternatively, the pre-processing of step 1212 may include synchronizing the first and second detected electronic signals so that, for example, they align in the time domain. In some cases, this synchronization may be similar to the correlation and/or synchronization of step 425. In some instances, synchronization of the first and second detected electronic signals may be performed using timestamps present within the first and second detected electronic signals. These timestamps may be generated by, for example, time-stamping device 185.

In step 1215, a portion of the first and second detected electronic signals and/or pre-processed first and second detected electronic signals that has been incident upon the fetus (referred to herein as "first fetal signal" and "second fetal signal," respectively) may be isolated from the first and second detected electronic signals received in steps 1205 and 1210, respectively. Step 1215 may be executed using any appropriate method of isolating the first and second fetal signals from the first and second detected electronic signals. Appropriate methods include, but are not limited to, reducing noise in the signal via, for example, application of filtering or amplification techniques (such as those disclosed herein), determining a portion of the first and second detected electronic signals that is contributed by the pregnant mammal and then subtracting or otherwise removing that portion of the first and second detected electronic signals from the first and second detected electronic signals, and/or receiving information regarding fetal heart rate and using that information to lock in (via, for example, a lock-in amplifier) on a portion of the first and second detected electronic signals generated by the fetus.

Next, in step 1220, the first and second fetal signals may be analyzed and processed to determine a value of the PPG pulse amplitude at end diastole for each fetal signal thereby determining a first and second PPG pulse amplitude at end diastole, which may be referred to herein as $I_{D1}$ and $I_{D2}$, respectively. In some instances, the PPG pulse amplitude at end diastole may be understood and/or referred to as an AC signal or value. Then, in step 1225, the first and second fetal signals may be analyzed and processed to determine a value of the PPG pulse amplitude during systole for each fetal signal thereby determining a first and second PPG pulse amplitude during systole, which may be referred to herein as $I_{S1}$ and $I_{S2}$, respectively. In some instances, the PPG pulse amplitude during systole may be understood and/or referred to as a DC signal or value. Because the path lengths for the first and second fetal signals are the same, or mathematically equivalent, the values of $I_{D1}$, $I_{D2}$, $I_{S1}$, and $I_{S2}$ may be determined without factoring in path length.

Then, a ratio of ratios (also referred to as "R") may be determined (step 1230). Step 1230 may be executed via performing the following calculation via Equation 3:

$$R = \frac{[(I_D - I_S)/I_S]_1}{[(I_D - I_S)/I_S]_2} \quad \text{Equation 3}$$

In some instances, R may be an average value determined via, for example, executing steps 1205-1220 a plurality of times to derive average values for $I_{D1}$, $I_{D2}$, $I_{S1}$, and $I_{S2}$ and then plugging these average values into Equation 3. Additionally, or alternatively, R may be determined by executing process 1200 a plurality of times (e.g., 20, 40, 50, etc.) to determine a plurality of R values that may then be averaged to determine an average R value.

In some embodiments, the R value determined via execution of process 1200 may be determined on a case-by-case basis for each individual pregnant mammal and/or fetus to customize, or personalize, the R value for each situation, pregnant mammal, and/or fetus. This specificity of individualized R values may be of clinical importance because it provides a more accurate determination of R than when a value for R is determined by a pulse oximeter manufacturer as an average across all situations. Typically, a R value is provided by a pulse oximeter manufacturer and it is based on an evaluation of experimentally determined results averaged across a number of situations/individuals. A problem with this approach is that it presumes conditions under which the pulse oximeter will be used from patient to patient or situation to situation will be relatively uniform as is the case with a finger or ear lobe, which are traditional locations on the body where pulse oximetry measurements are taken from. However, such an assumption may not be appropriate for a pregnant mammal because it may not be sufficiently accurate for all pregnant mammals/fetuses due to a wide variety of variations between pregnant mammals and their fetuses.

At times, process 1200 may be executed a plurality of times during a monitoring session on, for example, a periodic or as-needed basis to specifically tailor the R value to a point in time or situation. For example, process 1200 may be executed every hour, half-hour, or minute during labor and delivery of the fetus in order to adjust R values when, for example, a fetus and/or the pregnant mammal or her uterus moves.

FIG. 13 is a flowchart illustrating a process 1300 for determining a level of oxygen saturation for fetal hemoglobin using a pulse oximeter. Process 1300 may be performed by, for example, system 100 or components therein.

Initially, a first detected electronic signal that corresponds to an optical signal of a first wavelength, or first range of wavelengths, exiting from the abdomen of a pregnant mammal and a fetus contained therein may be received (step 1305) by, for example, a computer or processor such as computer 150. In step 1310, a second detected electronic signal that corresponds to an optical signal of a second wavelength, or second range of wavelengths, exiting from the abdomen of a pregnant mammal and a fetus contained therein may be received by, for example, the computer or processor. The first and second detected electronic signals may be communicated directly, or indirectly, to the computer by/from a detector like detector 160.

The first and second optical signals may be incident upon and/or directed into the pregnant mammal's abdomen by one or more light sources like light source 105. In many instances, the wavelengths of the first and second optical signals are chosen so that a path length of the respective first and second optical signals will be the same or sufficiently close to one another to be mathematically insignificant. For example, a first optical signal may be 790 nm and a second optical signal may be 810 nm or, a first optical signal may be 795 nm and a second optical signal may be 815 nm. In many instances, the light sources used to generate the first and second optical signal will be light source(s) capable of generating mono-chromatic light and/or light within a narrow band of wavelengths such as a laser or LED. Optionally, in step 1312, the first and/or second detected electronic signal(s) may be pre-processed in order to, for example, remove noise and/or amplify a desired portion of the respective first and/or second detected electronic signal(s). This pre-processing may be similar to the pre-processing executed in step 407 of process 400 and discussed above with regard to FIG. 4. Additionally, or alternatively, the pre-processing of step 1312 may include synchronizing the first and second detected electronic signals so that, for example, they align in the time domain. In some cases, this synchronization may be similar to the correlation and/or synchronization of step 425. In some instances, synchronization of the first and second detected electronic signals may be performed using timestamps present within the first and second detected electronic signals. These timestamps may be generated by, for example, timestamping device 185.

In step 1315, a portion of the first and second detected electronic signals that has been incident upon the fetus (referred to herein as "first fetal signal" and "second fetal signal", respectively) may be isolated from the first and second detected electronic signals received in steps 1305 and 1310, respectively and/or pre-processed in step 1307. Step 1315 may be executed using any appropriate method of isolating the first and second fetal signals from the first and second detected electronic signals. Appropriate methods include, but are not limited to, reducing noise in the signal via, for example, application of filtering or amplification techniques, determining a portion of the first and second detected electronic signals that is contributed by the pregnant mammal and then subtracting or otherwise removing that portion of the first and second detected electronic signals to isolate the first and second fetal signals from the first and second detected electronic signals and/or receiving information regarding fetal heart rate and using that information to lock in on a portion of the first and second detected electronic signals generated by the fetus.

In step 1320, an R value for the fetus and/or pulse oximetry device (e.g., fetal probe 115) may be received. In some instances, an R value for the fetus may be generated via execution of process 1200 and may be the R value determined at step 1230. Additionally, or alternatively, the R value may also be provided by the manufacturer of the pulse oximetry device, or may be an otherwise known R value.

Next, in step 1325, the first and second fetal signals may be analyzed and processed to determine a fetal hemoglobin oxygen saturation level. In some instances, execution of step 1325 may include determining an extinction coefficient for oxygenated hemoglobin ($\varepsilon_O$) and deoxygenated hemoglobin ($\varepsilon_d$) for the first and second fetal signals. The extinction coefficient of hemoglobin may be understood as an absorption constant of the sample divided by the hemoglobin concentration. Once the extinction coefficients are determined, they may be plugged into the following equation (Equation 4) to determine the hemoglobin oxygen saturation (SpO$_2$) for the fetus:

$$SpO_2 = \frac{\varepsilon_{d1} - R(I_2/I_1)\varepsilon_{d2}}{R(I_2/I_1)(\varepsilon_{02} - \varepsilon_{d2}) + (\varepsilon_{d1} - \varepsilon_{01})} \quad \text{Equation 4}$$

Where:
$\varepsilon_{d1}$=the extinction coefficient for deoxygenated hemoglobin for $\lambda_1$;
$\varepsilon_{d2}$=the extinction coefficient for deoxygenated hemoglobin for $\lambda_2$;
$\varepsilon_{01}$=the extinction coefficient for oxygenated hemoglobin for $\lambda_1$;
$\varepsilon_{02}$=the extinction coefficient for oxygenated hemoglobin for $\lambda_2$;

$I_1$=the path length for $\lambda_1$; and
$I_2$=the path length for $\lambda_2$.

However, when the path length for $\lambda_1$ and $\lambda_2$ are the same, or sufficiently close, the calculation of $I_2/I_1$ results in a value of 1, or close to 1, and may be removed from Equation 4, resulting in Equation 5:

$$SpO_2 = \frac{\varepsilon_{d1} - R\varepsilon_{d2}}{R(\varepsilon_{02} - \varepsilon_{d2}) + (\varepsilon_{d1} - \varepsilon_{01})} \quad \text{Equation 5}$$

Once determined, provision of the fetal oxygen hemoglobin saturation (SpO$_2$) value to a user (e.g., doctor, nurse, or patient) may be facilitated (step 1330) via, for example, providing the indication to a display device (e.g., display device 155), or a computer (e.g., computer 150) screen or screen of a device (e.g., fetal probe 115).

Figure 14A:
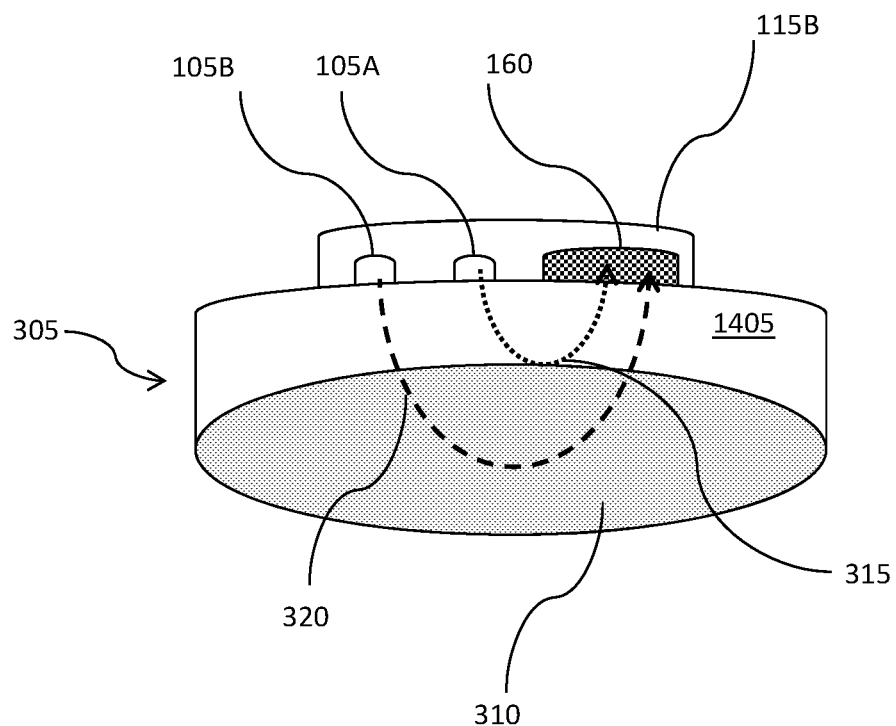
FIG. 14A illustrates an exemplary fetal probe configured to detect short separation and long separation signals in contact with a pregnant mammal's abdomen where the layers of the maternal abdomen are depicted as a single layer, consistent with some embodiments of the present invention.

FIG. 14A illustrates an exemplary fetal probe 115B in contact with a pregnant mammal's abdomen in a manner similar to that shown in FIG. 3. In FIG. 14A the layers of maternal tissue as shown in, for example, FIGS. 2A and 2B are resolved, or simplified, into a simplified layer of maternal tissue 1405 that approximates the properties of the multiple layers of tissue under study. In other embodiments, the maternal tissue layers may be resolved into a two or more simplified layers (not shown). Fetal probe 115B is configured to enable short separation (SS) analysis of light emitted from the pregnant mammal's abdomen and the fetus contained therein.

Fetal probe 115B includes a first light source 105A that emits first optical signal 315, a second light source 105B that emits second optical signal 320, and a detector 160. First and/or second light beams 315 and/or 320 may include light of a single, or multiple, wavelengths and may be within, for example, the red, NIR, or infra-red spectrum. In some circumstances, characteristics of optical signal 315 may be different from the wavelength of optical signal 320 and/or may be projected into the pregnant mammal's abdomen at a different time to enable distinguishing light projected from the two light sources when it is received by detector 160 and processed according to one or more of the processes described herein. In some embodiments, fetal probe 115B may include a filter (not shown) for detector 160 that may be attenuated to so that, for example, detector 160 detects and equal amount of light from first and second light sources 105A and 105B.

In many instances, a depth of light propagation through the pregnant mammal's abdomen is dependent on a distance between a light source and a detector. In some embodiments, the position of first light source 105A and/or second light source 105B may be adjusted (e.g., moved closer to, or further away from, detector 160) so as to, for example, adjust a depth of penetration for the light emitted therefrom. The adjustment may be facilitated by, for example, a track or other positioning device included in fetal probe 115B (not shown). In some instances, the positioning of first light source 105A and/or second light source 105B may be adjusted responsively to a depth of fetus 310 within the pregnant mammal's abdomen (i.e., a measurement of the width of maternal tissue 1405 positioned between the fetal probe 115B and the fetus 310). A measurement of a depth of fetus 310 within the pregnant mammal's abdomen may be provided by, for example, an ultrasound or Doppler probe like Doppler/ultrasound probe 135 and/or an MRI image like illustrations 201 and 202.

In some embodiments, first light source 105A may be positioned relative to detector 160 so that light emitted from first light source (i.e., optical signal 315) only propagates through the maternal tissue 1405 and does not reach fetus 310. Second light source 105B may be positioned further away (relative to first light source 105A) from detector 160 so that light projected by second light source 105B (i.e., optical signal 320) projects deeper into the pregnant mammal's abdomen than optical signal 315 and back scattering therefrom and/or transmission therethrough are detected by detector 160. Stated differently, light source 105A may be positioned so optical signal 315 only projects into maternal tissue 1405 so that the portion of optical signal 315 detected by detector 160 may only be back scattered from and/or transmitted through maternal tissue 1405 and not the fetus 310 while light source 105B may be positioned so optical signal 320 projects into both maternal tissue 1405 and fetus 310 so that the portion of optical signal 320 detected by detector 160 may be back scattered from and/or transmitted through from maternal tissue 1405 and the fetus 310. This positioning of first light source 105A may facilitate short separation (SS) measurements and the path of first optical signal 315 and/or the detected amounts of first optical signal 315 by detector 160 may be referred to herein as a SS channel. This positioning of second light source 105B may facilitate long separation (LS) measurements and the path of second optical signal 320 and/or the detected amounts of second optical signal 320 by detector 160 may be referred to herein as a LS channel.

Figure 14B:
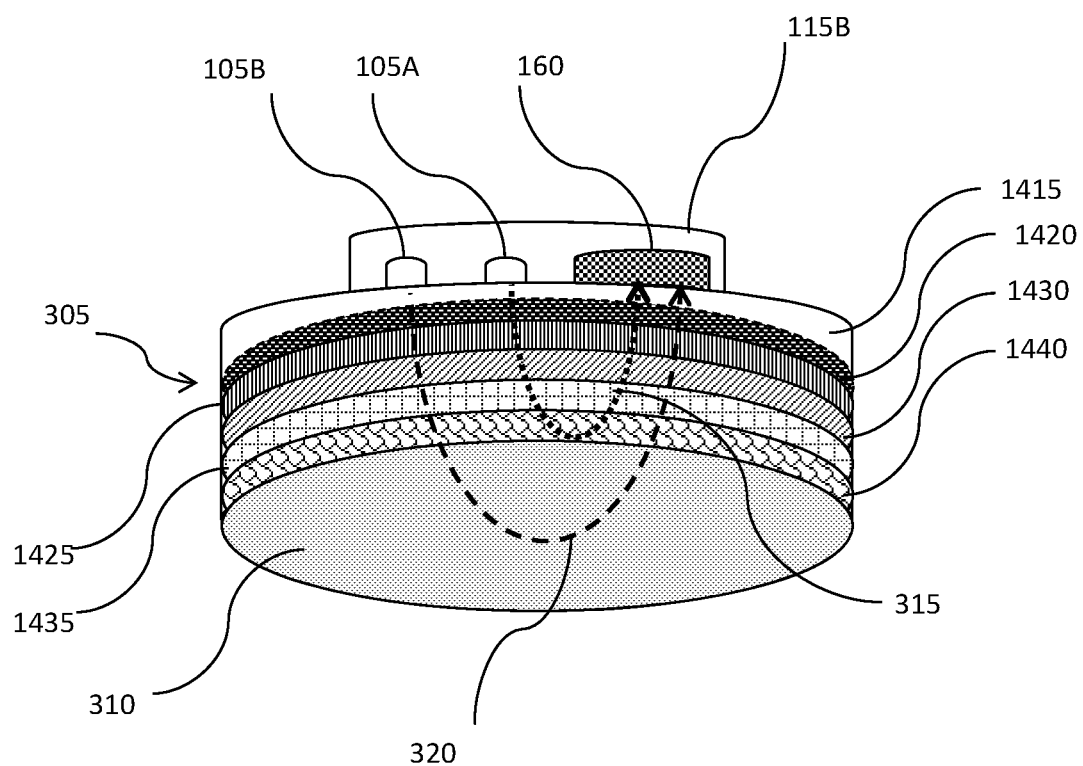
FIG. 14B illustrates an exemplary fetal probe configured to detect short separation and long separation signals in contact with a pregnant mammal's abdomen showing the different layers of maternal tissue, consistent with some embodiments of the present invention.

FIG. 14B provides a set up similar to that of FIG. 14A with the exception that the layers of tissue have not been resolved into simplified layer of maternal tissue 1405 and instead an approximation of each individual layer of maternal and fetal tissue is shown. More specifically, FIG. 14B shows a first layer that represents/approximates a maternal skin layer 1415, a second layer that represents/approximates a maternal subcutaneous fat layer 1420, a third layer that represents/approximates a maternal abdominal muscle (skeletal muscle) layer 1425, a fourth layer that represents/approximates a maternal intraperitoneal fat layer 1430, a fifth layer that represents/approximates a uterine wall (smooth muscle) layer 1435, a sixth layer that represents/approximates an amniotic fluid layer 1440, and a seventh layer that represents/approximates the fetus 310. In some embodiments, representations and/or approximations of these tissue layers may include a manner in which the layer may influence the behavior (e.g., scattering and/or absorption) of light and/or photons passing through the respective tissue layer. At times, these approximations and/or representations may be made with the aid of computer modeling techniques via, for example, MATLAB or other computer modeling software.

In some embodiments, actual measurements and/or approximate dimensions for maternal and/or fetal tissue used to develop the representation and/or approximation of a feature of a tissue layer may be based on, for example, ultrasound images, MRI images, illustrations like illustrations 201 or 202, and/or other information (e.g., melanin content, body weight, body mass index, fetal gestational age, etc.) regarding the pregnant mammal and/or fetus.

In the embodiment of FIG. 14B, the first light beam 1415 penetrates layers 1415-1440 and may therefore provide information regarding each of these layers separately and/or in the aggregate. In some embodiments, first light beam 1415 may be adjusted so that it only penetrates to a depth of a layer under study (e.g., 1415, 1420, 1425, 1430, 1435) of the maternal tissue to ascertain, for example, properties and/or characteristics (e.g., scattering of light, or absorption of light, and/or hemoglobin saturation level) of the tissue layer of interest.

Figure 15A:
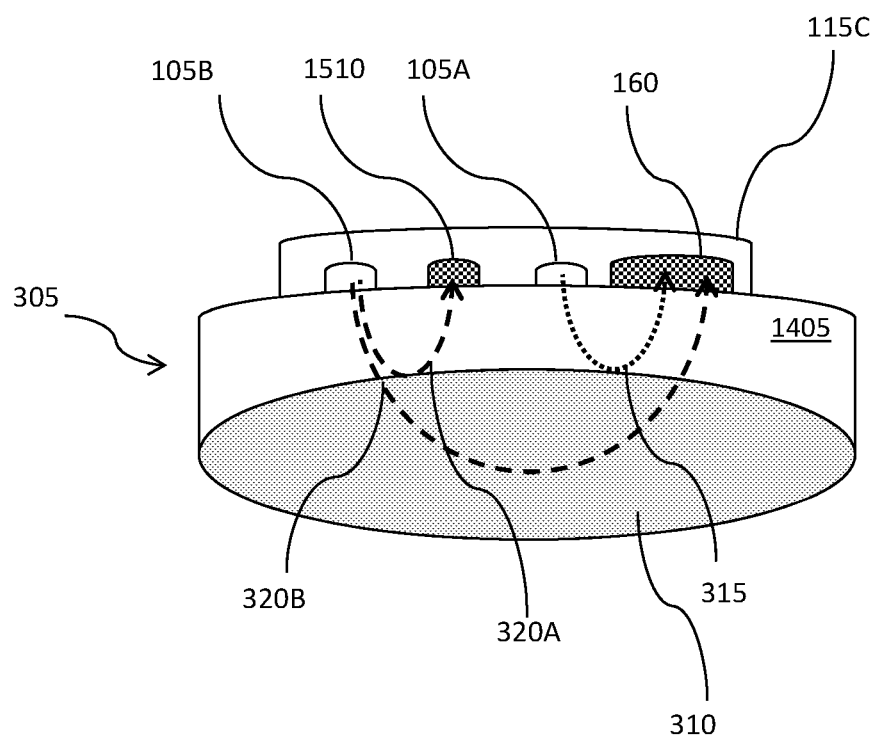
FIG. 15A illustrates an exemplary fetal probe configured to detect two short separation signals and one long separation signal in contact with a pregnant mammal's abdomen where the layers of the maternal abdomen are depicted as a single layer, consistent with some embodiments of the present invention.

FIG. 15A illustrates an exemplary fetal probe 115C in contact with a pregnant mammal's abdomen in a manner similar to that shown in FIGS. 3, 14A, and 14B. The embodiment shown in FIG. 15A utilizes the simplified layer of maternal tissue 1405 and fetal probe 115C is configured to enable double short separation (SS) analysis of light back scattered from and/or transmitted through the pregnant mammal's abdomen and the fetus contained therein.

Fetal probe 115C includes a first light source 105A that emits first optical signal 315, a small detector 1510, a second light source 105B that emits second optical signal 320, and detector 160. A first portion of second optical signal 320A may be detected by small detector 1510 and a second portion of second optical signal 320B may be detected by detector 160. First and/or second light beams 315 and/or 320 may include light of a single, or multiple, wavelengths and may be within, for example, the red, near infra-red, and/or broadband spectrum. In some circumstances, the wavelength for optical signal 315 may be different from the wavelength of optical signal 320 and/or may be projected at different times to enable differentiation between light projected from the two light sources when it is received by detector 160 and processed according to one or more of the processes described herein. Small detector 1510 may be similar to detector 160 but may have, for example, a smaller size and/or decreased sensitivity. In some instances, small detector 1510 may be a small fiber detector. In some embodiments, fetal probe 115C may include a filter (not shown) for detector 160 that may be attenuated to so that detector 160 detects and equal amount of light from first and second light sources 105A and 1056.

In some embodiments, the position of first light source 105A and/or second light source 105B may be adjusted (e.g., moved closer to, or further away from, detector 160) so as to, for example, adjust a depth of penetration for the light emitted therefrom that is detected by detector 160. The adjustment may be facilitated by, for example, manual manipulation and/or placement of a detector and/or moving a detector along a track or other positioning device included in and/or associated with fetal probe 115C (not shown). In some instances, the positioning of first light source 105A and/or second light source 1056 may be adjusted responsively to a depth of fetus 310 within the pregnant mammal's abdomen (i.e., a measurement of the width of maternal tissue 1405 positioned between the fetal probe 115C and the fetus 310). A measurement of a depth of fetus 310 within the pregnant mammal's abdomen may be provided by, for example, an ultrasound or Doppler probe like Doper/ultrasound probe 135 and/or an image of the pregnant mammal's abdomen like illustrations 201 and 202.

In some embodiments, first light source 105A may be positioned relative to detector 160 so that light emitted from first light source (i.e., optical signal 315) only propagates through the maternal tissue 305 and does not reach fetus 310. Second light source 105B may be positioned further away (relative to first light source 105A) from detector 160 so that light projected by second light source 105B (i.e., optical signal 320) projects deeper into the pregnant mammal's abdomen than optical signal 315 so that it reaches fetus 310 so that light back scattered from and/or transmitted through the fetus may be detected by detector 160. Small detector 1510 may be positioned between first and second light sources 105A and 105B so that light (i.e., optical signal 320) only propagates through the maternal tissue 1405 prior to detection by small detector 1510 and does not reach fetus 310. This positioning of first light source 105A may facilitate collection of a first set of short separation (SS) measurements and the path of first optical signal 315 and/or the detected amounts of first optical signal 315 by detector 160 may be referred to herein as a first SS channel. This positioning of second light source 105B may facilitate long separation (LS) measurements and the path of second optical signal 320 and/or the detected amounts of second optical signal 320 by detector 160 may be referred to herein as a LS channel. This positioning of small detector 1510 may facilitate a second set of short separation (SS) measurements and the path of first optical signal 315 and/or the detected amounts of first optical signal 315 by detector 160 may be referred to herein as a second SS channel. Thus, fetal probe 115C provides for SS measurements of both the first and second light sources 105A and 105B.

Figure 16:
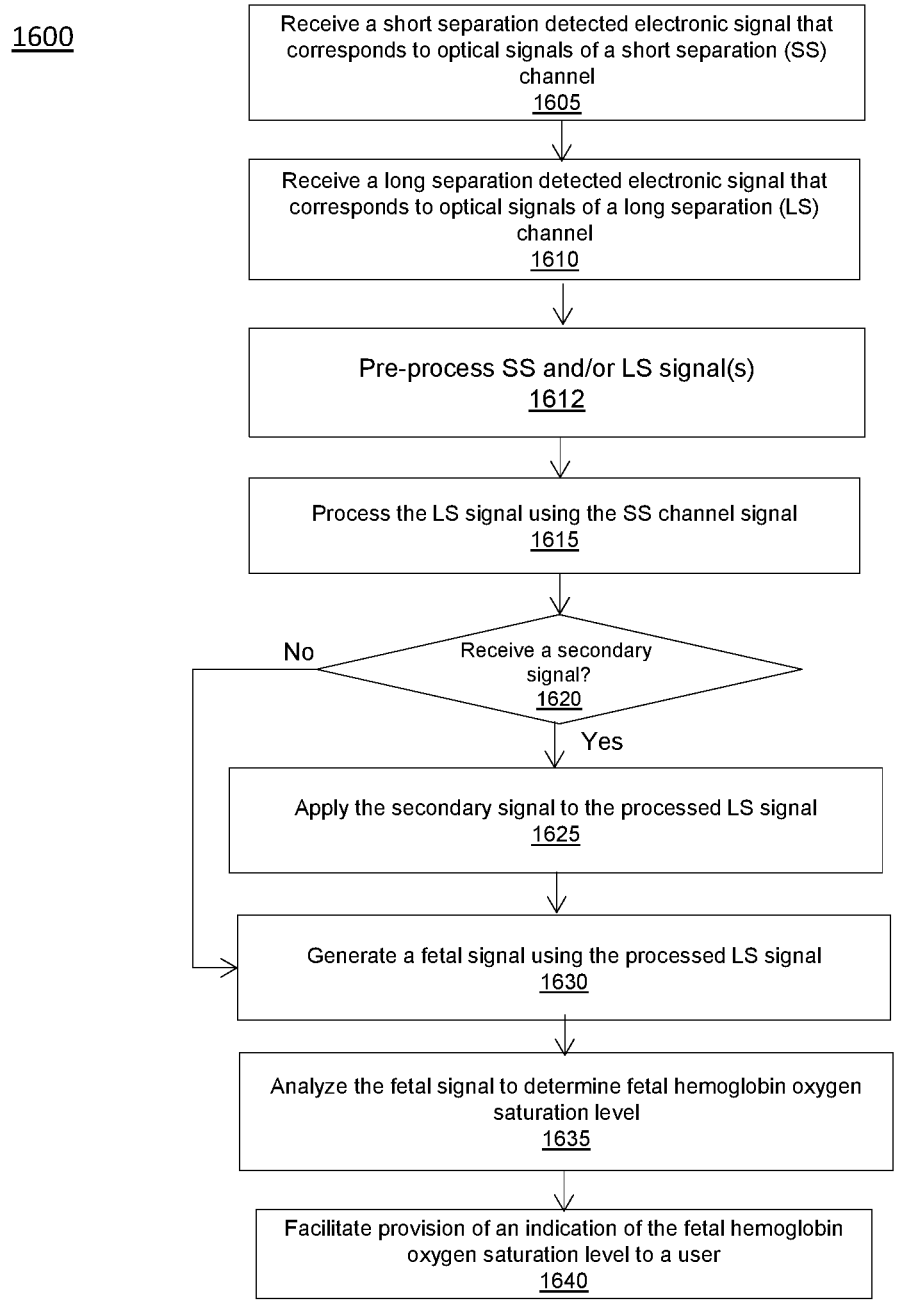
FIG. 16 is a flowchart illustrating an exemplary process for using a set of short separation signals to generate a fetal signal that may be used to determine a fetal hemoglobin oxygen saturation level, consistent with some embodiments of the present invention.

FIG. 16 is a flowchart illustrating an exemplary process 1600 for using a set of short separation (SS) signals to generate a fetal signal that may be used to determine a fetal hemoglobin oxygen saturation level. Process 1600 may be executed by, for example, system 100 and/or components thereof. In particular, process 1600 may be executed by receiving information from fetal probe like fetal probe 115B and/or 115C of depicted in FIGS. 14A and 14B and discussed above.

Initially, in step 1605, a short separation detected electronic signal may be received by, for example, a computer like computer 150 and/or a processor. The short separation detected electronic signal (also referred to herein as a "short separation signal" or "SS signal") may correspond to one or more optical signals of a short separation channel. The SS signal may result from a set of optical signals that are projected into the abdomen of a pregnant mammal from one or more light sources, like light source 105, and exits from the abdomen and, more specifically, from maternal tissue 1405 via, for example, transmission and/or back scattering. The SS signal may be similar to a portion of first optical signal 315 that is detected by a detector like detector 160 as shown in FIGS. 14A and/or 14B.

The SS signal may correspond to optical signals of two or more different wavelengths, or ranges of wavelengths, that may be in, for example, the red and/or near infra-red portion of the electromagnetic spectrum that may be detected by a detector like detector 160 and converted into an electrical signal (i.e., the SS signal) that may be communicated to the computer or processor. A light source for the optical signal that generates the SS signal may be sufficiently close to the detector that only light incident on maternal tissue is detected by the detector due to, for example, a distance between the light source and the detector.

In step 1610, a long separation detected electronic signal may be received by, for example, the computer and/or a processor. The long separation detected electronic signal (also referred to herein as a "long separation signal" or "LS signal") may correspond to one or more optical signals of a long separation channel. The LS signal may result from a second optical signal that is projected into the abdomen of a pregnant mammal from a light source, like second light source 105B and back scattered from and/or transmitted through the abdomen and, more specifically, from/through maternal tissue and/or a fetus contained therein, detected by a detector like detector 160, and converted into an electrical signal (i.e., the LS signal), which may be communicated to the computer or processor. The LS signal may correspond to an optical signal like second optical signal 320, which may travel along a LS channel. The LS signal may be of a second wavelength or a second range of wavelengths that may be in, for example, the red and/or NIR spectrum that may, in some instances, be different from the wavelength or range of wavelengths of the SS signal. This difference may assist with differentiation of the SS and LS optical and/or detected electronic signals. The SS and/or LS signal(s) may have some similarities with the detected electronic signal received in step 405 of process 400 discussed above with regard to FIG. 4.

Optionally, in step 1612, the SS and/or LS signal(s) may be pre-processed in order to, for example, remove noise and/or amplify a desired portion of the respective first and/or second detected electronic signal(s). This pre-processing may be similar to the pre-processing executed in step 407 of process 400 and discussed above with regard to FIG. 4. Additionally, or alternatively, the pre-processing of step 1612 may include synchronizing and/or correlating the SS and LS signals so that, for example, they align in the time domain. In some cases, this synchronization may be similar to the correlation and/or synchronization of step 425. At times, synchronization of the SS and LS signals may be performed using timestamps present within the SS and LS signals that, for example, provide for a simultaneous, or nearly simultaneous, start to the detection of the SS and LS signals. These timestamps may be generated by, for example, timestamping device 185 in a manner similar to that discussed above.

Figure 15B:
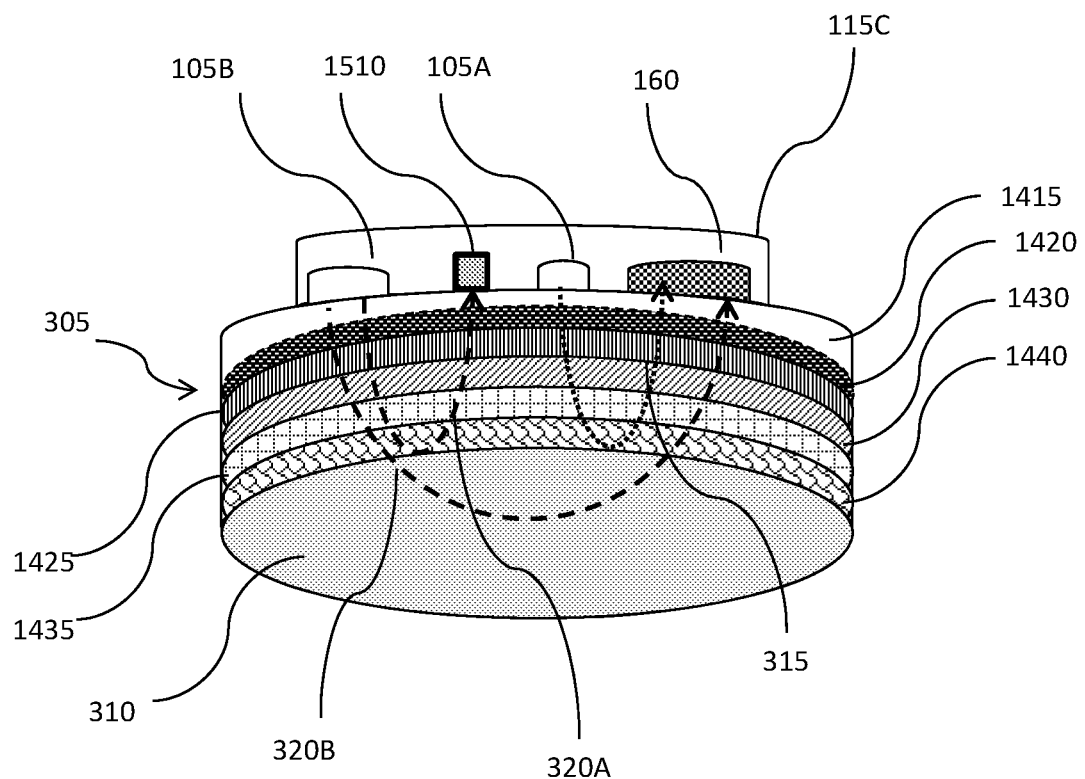
FIG. 15B illustrates an exemplary fetal probe configured to detect two short separation signals and one long separation signal in contact with a pregnant mammal's abdomen where each of the layers of the maternal abdomen are shown, consistent with some embodiments of the present invention.

In step 1615, the LS signal may be processed using the SS signal and/or pre-processed SS and/or LS signal. A purpose of this processing may be to understand features of a signal back scattered from and/or transmitted only through the pregnant mammal's tissue (i.e., not incident on the fetus), which may be represented by the SS signal. Further information regarding and exemplary dimensions of maternal tissue are shown in illustrations 201 and 202 of FIGS. 2A and 2B and provided by FIGS. 14B and 15B and the associated discussions. A result of the processing of the SS signal may be removal, or subtraction, of information similar to the SS signal that may be present in the LS signal. In this way, a maternal contribution to the LS signal may be removed, which may serve to isolate the portion of the LS signal that represents light incident on the fetus, which may be referred to herein as a fetal signal. Additionally, or alternatively, the processing of step 1615 may reduce contamination (e.g., maternal physiological signals like light scattering caused by uterine contractions, light back scattered from and/or transmitted through maternal blood, etc.) in the LS signal so that a fetal signal present in the LS signal and caused by light back scattered from fetus may be more easily identifiable.

The processing of step 1615 may take many forms. At times, when the SS and LS optical signals include light of multiple wavelengths, the processing of 1615 may include separating portions of the SS and LS optical signals into portions that correspond with each of the multiple wavelengths so that, for example, each wavelength may be separately processed.

In some instances, the processing of step 1615 may include use of back-reflection geometry. Additionally, or alternatively, the processing of step 1615 may include subtracting the SS signal from the LS signal. Additionally, or alternatively, the processing of step 1615 may include using the SS signal as a regressor when processing the LS signal. Additionally, or alternatively, the processing of step 1615 may include applying one or more amplification (via e.g., a lock-in amplifier) and/or filtering (via e.g., a bandpass or Kalman filter) to the SS and/or LS signals. In some cases, execution of this filtering may resemble execution of step 435 discussed above with regard to FIG. 4.

In one example, the SS signal(s) may be analyzed to determine how the light of a first optical signal interacts with the maternal tissue. This information may be used to look for similar interactions of the LS signal with the pregnant mammal and the fetus so that these similar interactions may be understood as being transmitted through and/or back scattered from the pregnant mammal. Portions of the LS signal associated with these similar interactions may then be subtracted, or otherwise removed, from the LS signal. This may assist with removing contamination in the LS signal caused by the pregnant mammal and may make the portion of the LS signal contributed by the fetus easier to identify, discern, and/or analyze.

In step 1620, it may be determined whether a secondary signal (e.g., maternal heart rate signal, a fetal heart rate signal, a depth of the fetus within the pregnant mammal's abdomen, a maternal respiratory signal, uterine contraction information, light scattering information, information regarding noise in the signal, etc.) has been received. When a secondary signal has not been received, the processed LS signal may be used to generate a fetal signal (step 1625). The fetal signal may represent a portion of the LS signal contributed by light back scattered from and/or transmitted through the fetus.

When a secondary signal has been received, it may be applied to the processed LS signal of step 1615 (step 1625) to, for example, further remove noise from the signal and/or isolate the portion of the LS signal contributed by the fetus.

In step 1630, the processed LS signal of step 1615 or 1625 may be used to generate a fetal signal (step 1630). In some cases, the processed LS signal of step 1615 or 1625 may be a fetal signal without further processing or analysis to be performed in step 1630. Additionally, or alternatively, one or more additional processes (e.g., process 400, 500, 600, 700, and/or 800) may be applied to the LS signal in order to, for example, further refine the LS signal, amplify the fetus's contribution to the LS signal, and/or clarify the fetal signal.

The fetal signal may then be analyzed to determine a fetal hemoglobin oxygen saturation level using, for example, one or more processes described herein and/or performing calculations involving the Beer-Lambert Law and/or modified Beer-Lambert Law (step 1635) and provision of an indication of the fetal hemoglobin oxygen saturation level to a user (e.g., doctor, nurse, pregnant mammal, etc.) may be facilitated via, for example, a display device like display device 155 (step 1640).

Initially, in step 1705, a first SS signal may be received by, for example, a computer like computer 150 and/or a processor. The first SS signal may result from a first optical signal, like first optical signal 315, that is projected into the abdomen of a pregnant mammal from a light source, like light source 105A (shown and discussed above with regard to FIGS. 15A and 15B), back scattered from and/or transmitted through the abdomen and, more specifically, from/through maternal tissue (examples of which are provided by FIGS. 2A, 2B, 14A, 14B, 14A, and 15B and their associated discussion), and detected by a detector like detector 160. The first optical signal may be detected by a detector like detector 160 and converted into an electrical signal (i.e., the first SS signal) which is communicated to the computer or processor and received in step 1705. The first optical/SS signal may be of a first wavelength or a first range of wavelengths that may be in, for example, the red and/or NIRS spectrum.

In step 1710, a LS signal may be received by, for example, the computer and/or a processor. The LS signal may result from a second portion of a second optical signal, like second portion of second optical signal 320B, that is projected into the abdomen of a pregnant mammal from a light source, like second light source 105B and back scattered from and/or transmitted through the pregnant mammal's abdomen and/or fetus (e.g., from maternal tissue 1405 and/or fetus 310). The second portion of second optical signal may be detected by a detector like detector 160 and converted into an electrical signal (i.e., the LS signal) which may be communicated to the computer or processor. The LS signal may be of a second wavelength or a second range of wavelengths that may be in the NIRS spectrum that may be different from the wavelength or range of wavelengths of the first optical and/or SS signal.

In step 1715, a second SS signal may be received by, for example, the computer and/or a processor. The second SS signal may result from a first portion of the second optical signal that is projected into the abdomen of a pregnant mammal from a light source, like second light source 1056 and back scattered from and/or transmitted through the abdomen and, more specifically, from maternal tissue 1405. The optical signal may be detected by a detector like small detector 1510 and converted into an electrical signal (i.e., the second SS signal) which is communicated to the computer or processor. The second SS signal may correspond to a SS optical signal like the first portion of second optical signal 320A detected by a detector like small detector 1510. The second SS signal may be of the same wavelength or range of wavelengths as the LS signal.

Optionally, in step 1717, the first SS signal, LS signal, and/or second SS signal may be pre-processed in order to, for example, remove noise and/or amplify a desired portion of the respective SS signal, LS signal, and/or second SS signal(s). This pre-processing may be similar to the pre-processing executed in step 407 of process 400 and discussed above with regard to FIG. 4. Additionally, or alternatively, the pre-processing of step 1717 may include synchronizing the SS signal, LS signal, and/or second SS signals so that, for example, they align in the time domain. In some cases, this synchronization may be similar to the correlation and/or synchronization of step 425. In some instances, synchronization of the SS signal, LS signal, and/or second SS signal(s) may be performed using timestamps present within the SS signal, LS signal, and/or second SS signals. These timestamps may be generated by, for example, timestamping device 185.

In step 1720, the LS signal may be processed using both of the first and second SS signals. A purpose of the processing of step 1720 may be to understand features of a signal back scattered from and/or transmitted through maternal tissue at two different locations on the abdomen of the pregnant mammal so that these features may be removed from the LS signal to reveal a portion of the LS signal corresponding to light back scattered from and/or transmitted through the fetus. In some embodiments, the processing of step 1720 may reduce contamination (e.g., maternal physiological signals like scattering caused by uterine contractions or breathing, back scattering from and/or transmissions through from maternal blood, etc.) of the fetal signal caused by light back scattered from and/or transmitted through the pregnant mammal and/or noise. Receiving SS signals from two different locations may facilitate better understanding of spatially inhomogeneous reactions of the pregnant mammal's abdomen to incident light (e.g. the first and second optical signals). For example, a thickness of a pregnant mammal's uterine wall may be greater at one location than another and this differential may be accounted for with two SS signals, which may depend on placement of a fetal probe housing first and second detectors and/or placement of detectors and/or light sources within the probe.

The processing of step 1720 may take many forms. In some instances, the processing may include back-reflection geometry. Additionally, or alternatively, the processing of step 1720 may include subtracting both of the SS signals from the LS signal. Additionally, or alternatively, the processing of step 1720 may include using the first and/or second SS signal as a regressor when processing the LS signal. Additionally, or alternatively, the processing of step 1720 may include applying one or more amplification (via e.g., a lock-in amplifier) and/or filtering (via e.g., a bandpass or Kalman filter) processes or techniques to a detected electronic signal. In some instances, the two SS signals may be linearly combined and then used as a regressor input to a Kalman filtering algorithm for processing the LS signal.

In step 1725, it may be determined whether a secondary signal has been received. When a secondary signal has not been received, the processed LS signal may be used to generate a fetal signal (which, in some embodiments, may be the same as the processed LS signal of step 1720) (step 1735). The fetal signal may represent the light back scattered from and/or transmitted through the fetus.

When a secondary signal has been received, it may be applied (step 1730) to the processed LS signal of step 1720 to generate a fetal signal (step 1735). Exemplary secondary signals include, but are not limited to, a maternal heart rate signal, a fetal heart rate signal, a depth of the fetus within the pregnant mammal's abdomen, a maternal respiratory signal, uterine contraction information, light scattering information, information regarding noise in the signal, etc.

The fetal signal may then be analyzed to determine a fetal hemoglobin oxygen saturation level using, for example, one or more processes described herein and/or performing calculations involving the Beer-Lambert Law and/or modified Beer-Lambert Law (step 1740). In step 1745, provision of an indication of the fetal hemoglobin oxygen saturation level to a user (e.g., doctor, clinician, nurse, pregnant mammal, etc.) via, for example, a display device like display device 155 may be facilitated. In some embodiments, determination of fetal hemoglobin oxygen saturation and/or provision of the indication may similar to execution of steps 1635 and/or 1640 discussed above and may include, among other things, determining a TWA for the fetal hemoglobin oxygen saturation level and/or a concurrent display of fetal hemoglobin oxygen saturation level and fetal heart rate and/or a TWA of fetal heart rate.

Figure 18:
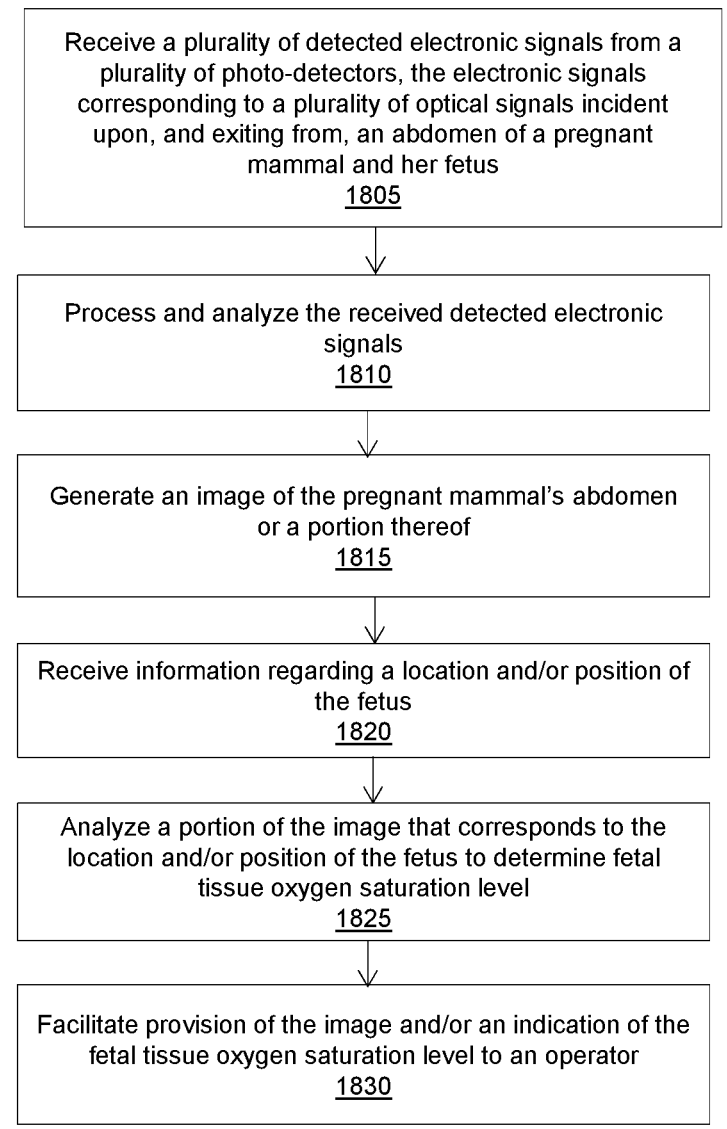
FIG. 18 is a flowchart illustrating an exemplary process for generating an image of a pregnant mammal's abdomen and/or fetus contained therein using diffuse optical tomography (DOT) and determining a fetal tissue oxygen saturation level therefrom, consistent with some embodiments of the present invention.

FIG. 18 provides a flowchart illustrating a process 1800 for generating an image of a pregnant mammal's abdomen and/or fetus contained therein using diffuse optical tomography (DOT) and determining a fetal tissue oxygen saturation level therefrom. Process 1800 may be performed by, for example, system 100 and/or components thereof. When DOT is performed, system 100 may include a plurality light sources 105 that may be lasers (e.g., synchronized picosecond pulsed diode laser) or optical fibers coupled to one or more lasers, a plurality of sensitive photo-electric detectors (e.g., single photon sensitive detectors) like detector 160, and a processor configured to process the output of the photo-electric detectors. In some embodiments, the plurality of lasers or optical fibers and photo-electric detectors may be arranged in an array configured to cover and conform to a portion of a pregnant mammal's abdomen so that a fetus therein may be imaged.

Initially, a plurality of detected electronic signals may be received from a plurality of photo-detectors (e.g., detectors 160) by a processor and/or computer like computer 150 (step 1805). The detected electronic signals may be transmitted directly to the processor or computer by the photo-detectors, a transceiver coupled to the detector, and/or a fetal probe such as fetal probe 115. Light incident upon, and exiting from, the pregnant mammal's abdomen may be generated by a plurality of light sources like light source 105 and may be of any acceptable frequency or wavelength (e.g., red and/or near infra-red (NIR)). On some occasions, the received detected electronic signals may resemble the detected electronic signals received in step 405 of process 400 discussed above. In some embodiments, the received detected electronic signals may be include and/or be associated with a detector identifier (e.g., an identification stamp) so that a position of a particular detected electronic signal may be known. This location may, in some instances, be used when the received detected electronic signals are processed and analyzed to determine various factors of the detected light and/or imaged tissue (step 1810).

At times, the processing and analysis of step 1810 may be performed using, for example, a number of photons detected by a particular detector, which detector detected a particular photon, a location or position of a detector providing a particular detected electronic signal, an intensity of light detected by a particular detected electronic signal, light scattering, an angle of incident light, an angle of exiting light, a photon's path length, a photon's time of flight, and so on. Exemplary factors that may be determined via execution of step 1810 include, but are not limited to, light absorption, light scattering, tissue density, and tissue oxygen saturation. Further details regarding how the detected electronic signals may be processed and analyzed are provided herein.

Optionally, execution of step 1810 may include processing one or more of the received plurality of detected electronic signals to, for example, remove noise and/or amplify a desired portion of the respective first and/or second detected electronic signal(s). This processing may be similar to the pre-processing executed in step 407 of process 400 and discussed above with regard to FIG. 4. Additionally, or alternatively, the processing of step 1810 may include synchronizing the plurality of detected electronic signals so that, for example, they align in the time domain. In some cases, this synchronization may be similar to the correlation and/or synchronization of step 425. In some instances, synchronization of the plurality of detected electronic signals may be performed using timestamps present within the plurality of detected electronic signals. These timestamps may be generated by, for example, timestamping device 185.

Figure 23:
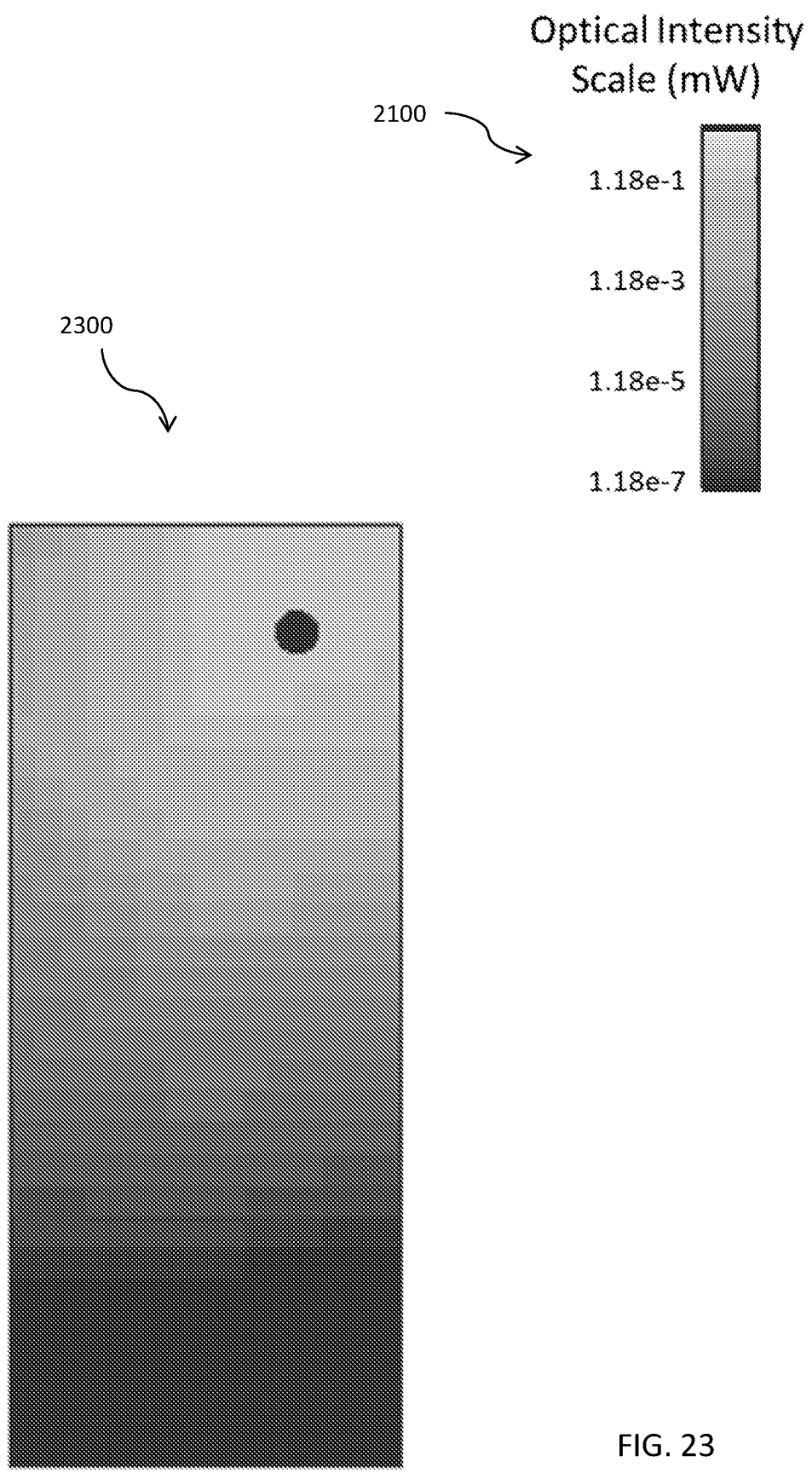
FIG. 23 provides a grey-scale-coded image with regional variations in intensity/quantity of detected photons measured in milliwatts where lighter shading indicates a higher intensity and darker shading indicates a lower intensity.

In step 1815, an image of the pregnant mammal's abdomen, or a portion thereof, may be generated using the results of the processing/analysis performed in step 1810. The image may show, for example, a density and/or an indication of tissue oxygen saturation for various layers of tissue (e.g., skin, fat, uterus, amniotic fluid, fetal skin, fetal brain, fetal muscle, etc.) included in the maternal abdomen and/or fetus. In embodiments where the image of the pregnant mammal's abdomen is generated using information regarding regional variations in tissue oxygen concentration, step 1815 may be executed by, for example, generating a color coded image (e.g., via grey scale or use of different colors to show different levels of tissue oxygen saturation) to indicate tissue oxygen saturation for various layers of maternal and/or fetal tissue and/or only the fetal tissue when, for example, step 1820 is performed prior to step 1815 as explained below. An example of an image 2300 generated via execution of step 1815 is provided in FIG. 23, which shows grey-scale-coded regional variations in intensity/quantity of detected photons measured in milliwatts where lighter shading indicates a higher intensity and darker shading indicates a lower intensity in accordance with a scale 2310. In some embodiments, these intensity values may be used to determine light absorption characteristics, which may be used to determine levels tissue oxygenation within the image. Additionally, or alternatively, the intensity values may be used to directly determine levels tissue oxygenation within the image.

In some embodiments, detected photons incident on the fetus may be differentiated from detected photons incident on the pregnant mammal using time of flight, or a time it takes for an emitted photon to be detected by a photodetector, for the detected photons. This time of flight may be determined using, for example, the location, depth, and/or position of the fetus. Detected photons determined to have been incident on the fetus may be used to generate an image like image 2300 so that tissue oxygenation of the fetus may be determined therefrom.

In step 1820, information regarding a location and/or position of the fetus may be received. This information may be received via, for example, an ultra-sound device or MRI image. At times, the fetal position and/or depth may be directly input into the computer by a user and/or medical care provider (e.g., physician and/or nurse) following his or her analysis of, for example, an ultrasound or MRI image.

In some embodiments, step 1820 may be executed prior to step 1815 so that, for example, information regarding the location and/or position of the fetus may be used to focus in on fetal tissue of interest prior to generation of an image of the pregnant mammal's abdomen so that only an image of the fetus/fetal tissue is generated. This may save considerable time and processing power when compared with executing step 1815 prior to step 1820 because, for example, only the portion of the image that corresponds with the fetus is generated (as opposed to the entire maternal abdomen and/or a portion thereof).

Optionally, in step 1825, a portion of the image corresponding to the location and/or position of the fetus may be examined or analyzed to determine a fetal tissue oxygen saturation level. Step 1825 may be executed by, for example, determining a numerical value for fetal tissue oxygen saturation based on the image generated in step 1815, intensity values associated the image, and/or the processed and analyzed signals of step 1810. Then, in step 1830 the generated image and/or an indication of the determined fetal tissue oxygen saturation level may be provided to a user via, for example, communication of the image/fetal tissue oxygen saturation level to a display device like display device 155. When step 1825 is not performed, a fetal tissue oxygen saturation level may be determined by a user (e.g., physician or technician) who visually observes the image of the maternal abdomen and/or fetus provided via execution of, for example, step 1830.

Figure 19:
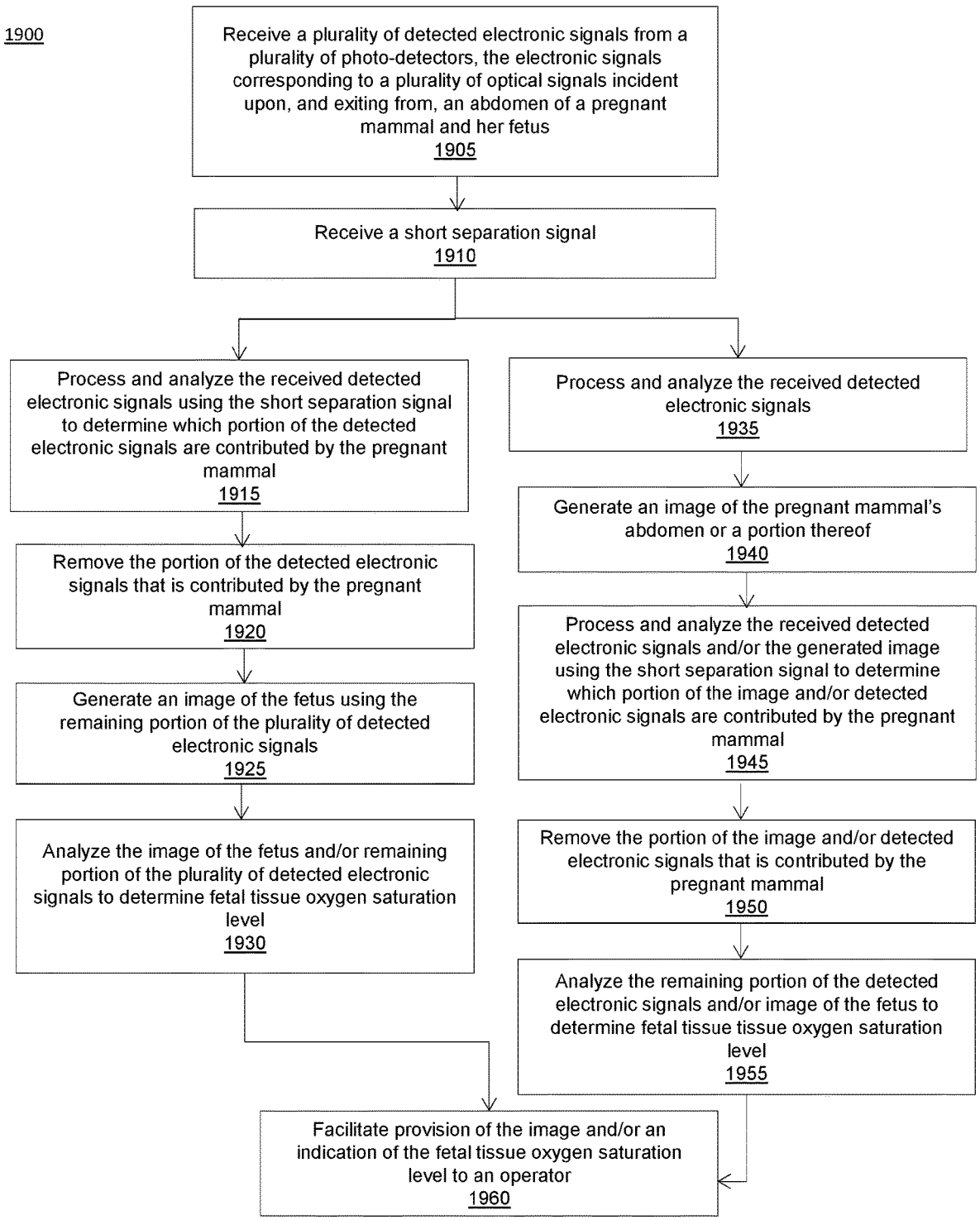
FIG. 19 is a flowchart illustrating an exemplary process for generating an image of a pregnant mammal's abdomen and/or fetus contained therein using DOT and determining a fetal tissue oxygen saturation level therefrom, consistent with some embodiments of the present invention.

FIG. 19 provides a flowchart illustrating a process 1900 for generating an image of a pregnant mammal's abdomen and/or fetus contained therein using DOT and determining a fetal tissue oxygen saturation level therefrom. Process 1900 may be performed by, for example, system 100 and/or components thereof. When DOT is performed, system 100 may include a plurality light sources 105 that may be lasers (e.g., synchronized picosecond pulsed diode laser) or optical fibers coupled to one or more lasers, a plurality of sensitive photo-electric detectors (e.g., single photon sensitive detectors) like detector 160, and a processor configured to process the output of the photo-electric detectors. In some embodiments, the plurality of lasers or optical fibers and photo-electric detectors may be arranged in an array configured to cover and conform to a portion of a pregnant mammal's abdomen so that a fetus therein may be imaged.

Initially, a plurality of detected electronic signals may be received from a plurality of photo-detectors (e.g., detectors 160) by a processor and/or computer like computer 150 (step 1905). Examples of fetal probes that may be used to detect the plurality of electronic signals are provided in FIGS. 1B and 1C. The detected electronic signals may be transmitted directly to the processor or computer by the photo-detectors, a transceiver coupled to the detected electronic signals, and/or a fetal probe such as fetal probe 115. Light incident upon, and exiting from, the pregnant mammal's abdomen may be generated by a plurality of light sources like light sources 105 and may be of any acceptable frequency or wavelength (e.g., red, near infra-red (NIR)). The received detected electronic signals may include and/or be associated with a detector identifier (e.g., modulation format; wavelength; location, orientation, and/or position of detector, etc.) and/or may be projected at a particular time so that a position of a particular detector detecting the electronic signal and/or a light source projecting a photon of the detected electronic signal may be known.

One or more short separation signal(s) may be received in step 1910 via, for example, communication of the short separation(s) signal from, for example, fetal probe 115, 115B, and/or 115C. As noted above, the short separation signal may provide information regarding the contribution of the pregnant mammal's tissue to the plurality of detected electronic signals. In embodiments where two or more short separation signals are received, this plurality of short separation signals may be used to determine information regarding the contribution of pregnant mammal's tissue to the plurality of detected electronic signals and/or features or characteristics of the maternal tissue at different locations on the maternal abdomen.

Figure 17:
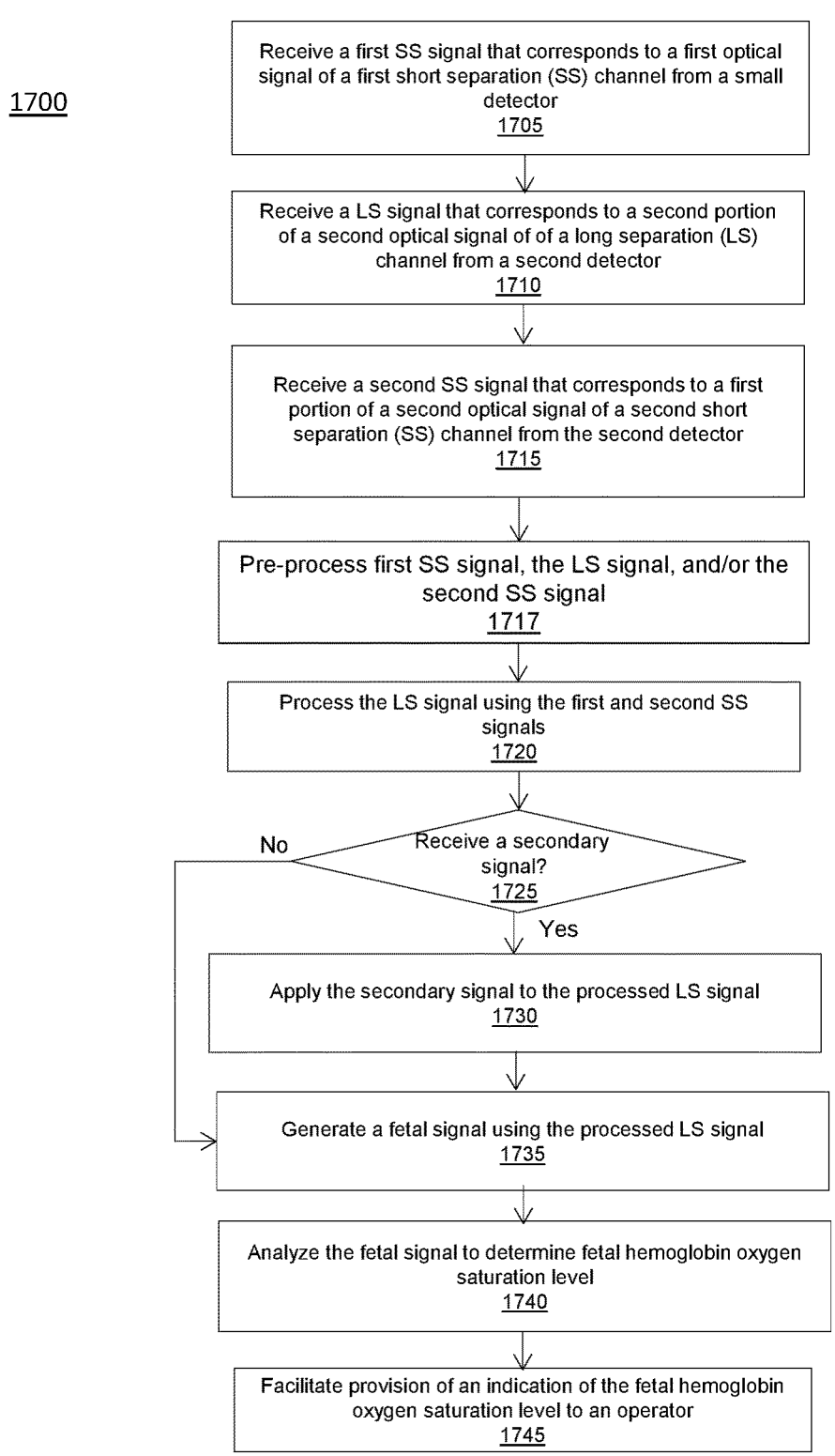
FIG. 17 is a flowchart illustrating an exemplary process for using two short separation measurements to generate a fetal signal that may be used to determine a fetal hemoglobin oxygen saturation level, consistent with some embodiments of the present invention.

In some embodiments, the short separation signal may include information regarding one or more layers of maternal tissue and characteristics thereof (e.g., absorption, scattering, location, width, etc.). For example, a plurality of short separation signals may be received and each short separation signal may include information about a different layer (e.g., skin, abdominal muscle, fat, uterine wall, and/or amniotic fluid). In some embodiments, the short separation signals may resemble the short separation signals received in steps 1605, 1705 and/or 1715 of processes 1600 and/or 1700 discussed herein with regard to FIGS. 16 and 17.

Then, either step 1915 or 1935 may be executed. When step 1915 is executed, the received detected electronic signals may be processed and analyzed using the one or more short separation signal(s) to determine, for example, which portion of the plurality of detected electronic signals are contributed by the pregnant mammal and/or not reflected from, or transmitted through, the fetus. Next, the portion of the plurality of detected electronic signals that are contributed by the pregnant mammal may be removed from the detected electronic signals (step 1920) via, for example, subtraction or application of a filter to the detected electronic signals that includes an indication or approximation of the portion of the plurality of detected electronic signals that are contributed by the pregnant mammal.

Optionally, in step 1925, an image of the fetus and/or fetal tissue, like image 2300, may be generated using the remaining portion of the detected electronic signals. The image may show, for example, an indication of density and/or tissue oxygen saturation for one or more layers of fetal tissue (e.g., skin, fat, brain, etc.). In embodiments where the image of the pregnant mammal's abdomen is generated using information regarding regional variations in tissue oxygen concentration, step 1925 may be executed by, for example, generating a color-coded image (e.g., via grey scale or use of different colors to show varying levels of tissue oxygen saturation) to indicate tissue oxygen saturation for one or more layers of fetal tissue. If the image generated in step 1925 visually shows the tissue oxygen saturation for one or more layers of fetal tissue, then step 1930 may not be executed and process 1900 may proceed to step 1960 whereby the generated image may be provided to a user via, for example, communication of the image/fetal tissue oxygen saturation level to a display device like display device 155.

When step 1925 is executed, the image of the fetus and/or fetal tissue may then be analyzed to determine a tissue oxygen saturation level of the fetus and/or imaged fetal tissue (step 1930) and then, in step 1960, the indication of the determined fetal tissue oxygen saturation level may be provided to a user via, for example, communication of the image/fetal tissue oxygen saturation level to a display device like display device 155.

When step 1925 is not executed, the remaining portion of the plurality of detected electronic signals may be analyzed to determine an indication of fetal tissue oxygen saturation level and this indication of the determined fetal tissue oxygen saturation level may be provided to a user via execution of step 1960.

In step 1935, the received detected electronic signals may be processed and analyzed in a manner similar to the execution of step 1810. Then, in step 1940, an image of the pregnant mammal's abdomen, or a portion thereof, may be generated using the results of the processing/analysis performed in step 1935 in a manner similar to execution of step 1815. Image 2300 discussed above with regard to FIG. 23 is an exemplary image like the one generated in step 1940.

Optionally, execution of step 1935 and/or 1915 may include pre-processing of the plurality of detected electronic signal to, for example, remove noise and/or amplify a desired portion of the respective plurality of detected electronic signal(s). This pre-processing may be similar to the pre-processing executed in step 407 of process 400 and discussed above with regard to FIG. 4. Additionally, or alternatively, execution of step 1935 and/or 1915 may include synchronizing two or more of the plurality of detected electronic signals so that, for example, they align in the time domain. In some cases, this synchronization may be similar to the correlation and/or synchronization of step 425. In some instances, synchronization of the plurality of detected electronic signals may be performed using timestamps present within the plurality of detected electronic signals. These timestamps may be generated by, for example, timestamping device 185.

In step 1945, the generated image and/or received detected electronic signals may be further processed and analyzed using the short separation signal received in step 1910 to, for example, determine which portion of the image and/or detected electronic signals are contributed by the pregnant mammal. Then, the portion of the image and/or received detected electronic signals contributed by the pregnant mammal may be removed from the image of step 1940 and/or the received detected electronic signals of step 1905 (step 1950) and the remaining portion of the image and/or received detected electronic signals may be analyzed to determine a level of fetal tissue oxygen saturation (step 1955). Then, step 1960 may be executed.

In some embodiments, determination of fetal tissue oxygen saturation and/or provision of the indication (e.g., steps 1930, 1955, and 1960) may similar to execution of steps 1825 and/or 1830 discussed above and may include, among other things, determining a time weighted average (TWA) for the fetal tissue oxygen saturation level and/or a concurrent display of fetal tissue oxygen saturation level and fetal heart rate and/or a TWA of fetal heart rate as discussed herein.

At times, the processing and analysis of step(s) 1915, 1930, 1935, 1945, and/or 1955 may be performed using information regarding, for example, a number of photons detected by a particular detector, which detector detected a particular photon or group of photons, a location or position of a detector providing a particular detected electronic signal, an intensity of light (or number of photons) detected by a particular detector, an intensity of light (or number of photons) of a particular wavelength or range of wavelengths detected by a particular detector, a degree of light scattering, an angle of incident light, an angle of exiting light, a photon's path length, a photon's time of flight, and so on. Further details regarding how the detected electronic signals may be processed and analyzed are provided below.

The DOT imaging of processes 1800 and 1900 may be performed using, for example, a time-domain (TD) system, a frequency-domain (FD) system, and/or a steady-state-domain (SSD) system. When a TD system is used, brief (e.g., 10-50 ps) light pulses that may be sinusoidally modulated with a frequency between, for example, 100 and 1000 MHz are projected in the pregnant mammal's abdomen at a repetition rate of, for example, 1-50 MHz. These pulses may yield photon-density waves inside the imaged tissue. From there, amplitude differences and phase shifts between the incident light and detected light may be determined as a function of time. Emitted photons (e.g., back reflected or transmitted) may then be either collected by an optical fiber and guided to a detector (e.g., photomultiplier) like detector 160 or directly detected by the detector like detector 160, which, in some embodiments, may be a microchannel plate photomultiplier (MCP-PMT). The MCP-PMT signals may then be amplified and/or attenuated and input into a constant fraction discriminator (CFD), the output of which may be provided to a time-to-amplitude converter (TAC). Output of the TAC may be counted as discrete events by a pulse-height analyzer (PHA) and accumulated until a peak count is reached (e.g., 100,000 counts, 1,000,000 counts, etc.). This information may be used to generate a time-response curve that is used to generate an image of the pregnant mammal's abdomen and/or determine a fetal tissue oxygen saturation.

When the DOT imaging of processes 1800 and/or 1900 are performed using a FD system, a sinusoidally amplitude-modulated light source may be used to project light into the pregnant mammal's abdomen. The modulation frequency may be between, for example, 100-1000 MHz. Measured parameters for an FD system may include phase shift ($\Phi$), and the demodulation of the light transmitted through the tissue compared with the incident light. Demodulation (M) may be understood via the Equation 6, reproduced below:

$$M=(AC_0/DC_0)/(AC_i/DC_i) \quad \text{Equation 6}$$

Where:
$AC_i$=AC amplitude offset of the intensity of the incident light;
$DC_i$=DC offset of the intensity of the incident light;
$AC_0$=AC amplitude of the exiting light; and $DC_0$=DC offset of the exiting light.

Phase shift (Φ) and M may be measured for all frequencies and, in some instances, a Fourier transform may be performed on the collected data to deduce t and M.

A TD system may include a light source (e.g., laser) (e.g., source 105), an intensity modulator, a light-delivery system (e.g., fetal probe 115), a light collection/detection system (e.g., detector 160), and a processor (like computer 150) for performing a cross-correlation technique that may be used to measure the phase shift and demodulation.

When the DOT imaging of processes 1800 and/or 1900 are performed using a SSD system a light source may continuously emit light of, for example, two different wavelengths (e.g., between 700 and 850 nm) into various points on the pregnant mammal's abdomen and the intensity of light exiting the pregnant mammal's abdomen may be measured via one or more detectors like detector 160. The output voltages of the detectors may be measured and then processed to generate an image of the pregnant mammal's abdomen that may show, for example, regional intensity of detected light.

At times, the processing of data acquired by a DOT system may involve application of a back-projection algorithm where detected electronic signals are fitted to analytical expressions based on diffusion theory to give absorption $\mu_a$ and transport scattering $\mu'_s$ coefficients. Such processing may yield a map of spatially dependent optical properties inside the pregnant mammal's abdomen. The spatially dependent optical properties may show differences between the types of tissue (e.g., skin, muscle, fetus, etc.) the light is passing through, which may be used to understand or determine fetal tissue oxygen saturation. At times these calculations may also factor in a probably that a detected photon has passed through a certain place, or layer, of tissue. These probabilities may be used to assign different characteristics (e.g., weights) to different regions or layers of the pregnant mammal's abdominal tissue.

Additionally, or alternatively, the processing of data acquired by a DOT system may involve application of model-based iterative image reconstruction (MO-BIIR) algorithms to the data. This process may involve three steps with the first step being application of a forward model that provides a prediction of the detected electronic signals and/or measurements based on an approximation of system parameters like $\mu_a$ and $\mu'_s$ for different tissue layers, tissue types, tissue locations, fetus location, and so on. In some embodiments, these predicted parameters may be informed by standard or average values for typical pregnant mammals and may be based on typical values for positions, locations, or optical properties of a pregnant mammal's abdomen or fetus. Additionally, or alternatively, these predicted parameters may be customized for a particular situation using, for example, ultrasound and/or short separation signal information that indicates characteristics of a particular pregnant mammal's abdomen (e.g., uterine thickness, skin thickness, fetal tissue type, fetal tissue thickness, fetal depth, etc.).

A second step may compare the predicted data with the received data. This comparison may result in an error function which may also be referred to as an objective function or norm. A third step may be updating the system parameters of step 1 (i.e., the forward model) to provide a new set of predicted data. This process may be iteratively repeated until, for example, the error function is of an acceptable value.

On some occasions, the detected electronic signals received in processes 700 and/or 1900 may be the result of light of two different wavelengths being projected into the maternal abdomen. Exemplary values for the first wavelength (λ1) range between 760 nm and 805 nm and exemplary values for the second wavelength (λ2) range between 808 nm and 830 nm. Often, the light of λ1 and λ2 will be monochromatic or within a narrow band of the electromagnetic spectrum. Light of both wavelengths may be incident upon the pregnant mammal's abdomen and collected via optical cables and passed to one or more detectors like detector 160 and/or may be directly detected by detector 160. The data collected by the detectors may then be processed via, for example, the Beer-Lambert law to determine changes in absorption coefficients at each detector and changes in oxyhemoglobin saturation (Δ[HbO]) and deoxyhemoglobin saturation (Δ[Hb]), respectively.

A reconstruction algorithm may be applied to account for path length differences between various source and detector positions and may be used to reconstruct predicted changes in the absorption coefficient $\Delta\mu_a$ at each detector. Then Equations 8a and 8b may be solved to determine changes in oxyhemoglobin saturation (Δ[HbO]) and deoxyhemoglobin saturation (Δ[Hb]). These values may then be used to generate a two- or three-dimensional map of the pregnant mammal's abdomen which show regional changes in oxyhemoglobin saturation (Δ[HbO]) and deoxyhemoglobin saturation (Δ[Hb]). The changes in oxyhemoglobin saturation (Δ[HbO]) and deoxyhemoglobin saturation (Δ[Hb]) may be shown using, for example, grey scale, color-coding and the images may be topographic, cross-sectional, and/or volumetric. While this process does not provide an absolute value for fetal hemoglobin oxygen saturation, it does provide a relative value for fetal hemoglobin oxygen saturation which may be used to monitor fetal hemoglobin oxygen saturation over time to determine changes thereto that may indicate the fetus is in distress as may be the case with a rapidly or slowly declining fetal hemoglobin oxygen saturation level.

Figure 20:
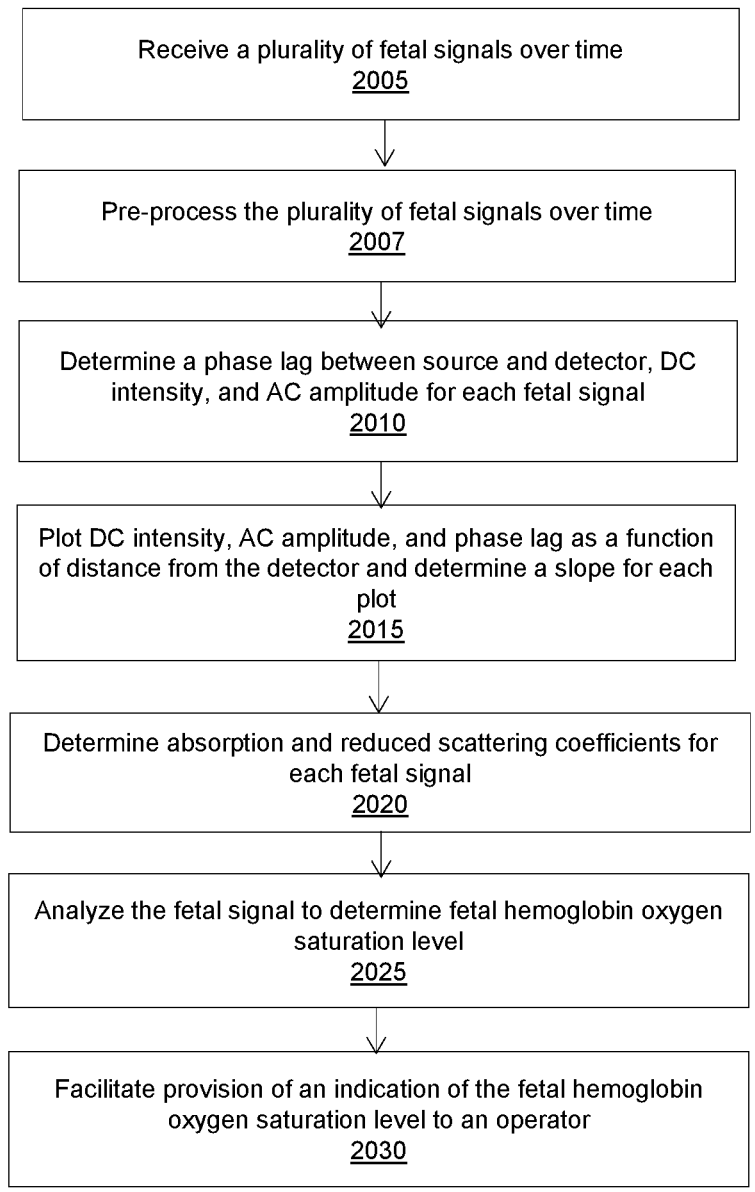
FIG. 20 is a flowchart illustrating a process for noninvasively determining a fetal hemoglobin oxygen saturation level using a multisource frequency-domain spectrometer, in accordance with some embodiments of the present invention.

FIG. 20 provides a flowchart of a process 2000 for noninvasively determining a fetal hemoglobin oxygen saturation level using a multisource frequency-domain spectrometer. Process 2000 may be performed by, for example, system 100 or any component or combination of components thereof.

Initially, a plurality of fetal signals, like the fetal signal generated by process 400, 500, 600, 700, 1000, 1200, 1300, 1600, 1700, 1900, may be received (step 2005). The received fetal signals may be of two or more wavelengths and may correspond to light projected by a plurality of light sources, like light sources 105 and detected by a detector like detector 160. A position of each light source within a probe like fetal probe 115, 115A, 115A', 115B, and/or 115C and/or a distance between each light source and the detector (r) may be known. The light used to generate the fetal signals (i.e., light projected into the pregnant mammal's abdomen) may be sinusoidally modulated. Light may be emitted from each of the light sources in successive manner (i.e., one at a time) which may, in some instances, be regulated by a multiplexer circuit so that, for example, light from each light source may be separately detected/analyzed. In some cases, each of the light sources may be set to emit light for a time that is a multiple of a desired frequency (e.g., 300, 400, or 500 MHz) for a desired number of periods. This may also be regulated by the multiplexer circuit.

Optionally, in step 2007, the plurality of fetal signals may be processed to, for example, remove noise and/or amplify a desired portion of the fetal signals. This pre-processing may be similar to the pre-processing executed in step 407 of process 400 and discussed above with regard to FIG. 4.

Additionally, or alternatively, execution of step 1935 and/or 1915 may include synchronizing two or more of the fetal signals so that, for example, they align in the time domain. In some cases, this synchronization may be similar to the correlation and/or synchronization of step 425. In some instances, synchronization of the plurality of fetal signals may be performed using timestamps present within the first and second detected electronic signals. These timestamps may be generated by, for example, timestamping device 185.

The received and/or pre-processed fetal signals may be processed (e.g., fast Fourier transform) to yield values for a phase lag between source and detector ($\Phi$), DC intensity, and AC amplitude (step 2010).

Then, these values may be individually plotted as a function of distance from the detector, r, and the slope of each graph may be determined thereby yielding values for $S_{ac}$, $S_{dc}$, and $S_\Phi$ (step 2015).

The values for $S_{ac}$, $S_{dc}$, and/or $S_\Phi$ may be used to determine an absorption coefficient pa and a reduced scattering coefficient µs for each fetal signal (step 2020). One way to determine $\mu_s$ and $\mu_a$ using $S_{ac}$, $S_{dc}$, and/or $S_\Phi$ is via infinite geometry calculations using equations 7, 8, and/or 9 as provided below:

$$\ln(rU_{dc}) = rS_{dc}(\mu_a, \mu_s') + K_{dc} \qquad \text{Equation 7}$$

where:
$U_{dc}$=the average photon density;
$S_{dc}$=the DC intensity slope;
r=the distance between the source and detector; and
$K_{dc}$=a DC intensity constant independent of r, $$\ln(rU_{ac}) = rS_{ac}(\mu_a, \mu_{K}') + K_{ac} \qquad \text{Equation 8}$$

where:
$U_{ac}$=the amplitude of the photon density oscillations;
$S_{ac}$=the AC amplitude slope; and
$K_{ac}$=an AC amplitude constant independent of r.

$$\Phi = rS_\Phi(\mu_a, \mu_s') + K_\Phi \qquad \text{Equation 9}$$

where:
$\Phi$=the phase lag between emission by the source and detection by the detector;
$S_\Phi$=the phase lag slope; and
$K_\Phi$=a phase lag constant independent of r.

Two of the measured quantities (DC intensity, AC amplitude, or phase lag) may be used to solve for $\mu_s$ and $\mu_a$ via equations like Equations 10 and 11 below, which use values for phase lag and DC intensity.

$$\mu_a = -\frac{\omega}{2v}\frac{S_{dc}}{S_{dp}}\left(\frac{S_\Phi^2}{S_{dc}^2}+1\right)^{-1/2} \qquad \text{Equation 10}$$

where:
$\omega/2\Pi$=the modulation frequency; and
v=the velocity of light in the medium.

$$\mu_s' = \frac{S_{dc}^2}{3\mu_a} - \mu_a \qquad \text{Equation 11}$$

Determining the scattering coefficients this way allows for the determination of fetal hemoglobin oxygen saturation without regard to path length. This may be helpful when doing transabdominal fetal oximetry because path length may vary substantially from pregnant mammal to pregnant mammal and, as such, approximations based on standard path lengths may not be accurate. Removing path length from the calculations of fetal hemoglobin oxygen saturation may allow for calculations of fetal hemoglobin oxygen saturation that do not need to be calibrated to account for path length. This removes considerable complexity from these determinations and also removes a possible source of error from these determinations.

Once $\mu_s$ and $\mu_a$ are solved for, the fetal hemoglobin oxygen saturation level may then be determined using, for example, Equations 12 and 13 below (step 2025).

$$[HbO_2] = \frac{\mu_a^{\lambda_1}\varepsilon_{Hb}^{\lambda_2} - \mu_a^{\lambda_2}\varepsilon_{Hb}^{\lambda_1}}{\varepsilon_{HbO_2}^{\lambda_1}\varepsilon_{Hb}^{\lambda_2} - \varepsilon_{HbO_2}^{\lambda_2}\varepsilon_{Hb}^{\lambda_1}} \qquad \text{Equation 12}$$

where:
$HbO_2$=the concentration value for oxygenated hemoglobin;
$\mu_a^{\lambda_1}$=the absorption coefficient for the first wavelength;
$\mu_a^{\lambda_2}$=the absorption coefficient for the second wavelength;
$\varepsilon_{HbO2}^{\lambda_1}$=the extinction coefficient for oxygenated hemoglobin for the first wavelength;
$\varepsilon_{HbO2}^{\lambda_2}$=the extinction coefficient for oxygenated hemoglobin for the second wavelength;
$\varepsilon_{Hb}^{\lambda_1}$=the extinction coefficient for deoxygenated hemoglobin for the first wavelength; and
$\varepsilon_{Hb}^{\lambda_2}$=the extinction coefficient for deoxygenated hemoglobin for the second wavelength.

The extinction coefficients are the molar extinction coefficients of the first and second wavelengths when being projected into the tissue or blood under study and are known quantities.

$$[Hb] = \frac{\mu_a^{\lambda_2}\varepsilon_{HbO_2}^{\lambda_1} - \mu_a^{\lambda_1}\varepsilon_{HbO_2}^{\lambda_2}}{\varepsilon_{HbO_2}^{\lambda_1}\varepsilon_{Hb}^{\lambda_2} - \varepsilon_{HbO_2}^{\lambda_2}\varepsilon_{Hb}^{\lambda_1}} \qquad \text{Equation 13}$$

where:
Hb=the concentration value for deoxygenated hemoglobin;

Once determined, a ratio of the Hb and HbO concentrations may be calculated to determine a hemoglobin oxygen saturation level for the fetus. An indication of this determined fetal hemoglobin oxygen saturation level may then be provided to a user (step 2030) via, for example, facilitating display of the fetal hemoglobin oxygen saturation level on a computer display device like display device 155.

In some embodiments, determination of fetal hemoglobin oxygen saturation and/or provision of the indication (steps 2025 and 2030, respectively) may similar to execution of steps 240 and/or 245 discussed above and may include, among other things, determining a TWA for the fetal hemoglobin oxygen saturation level and/or a concurrent display of fetal hemoglobin oxygen saturation level and fetal heart rate and/or a TWA of fetal heart rate.

Figure 21:
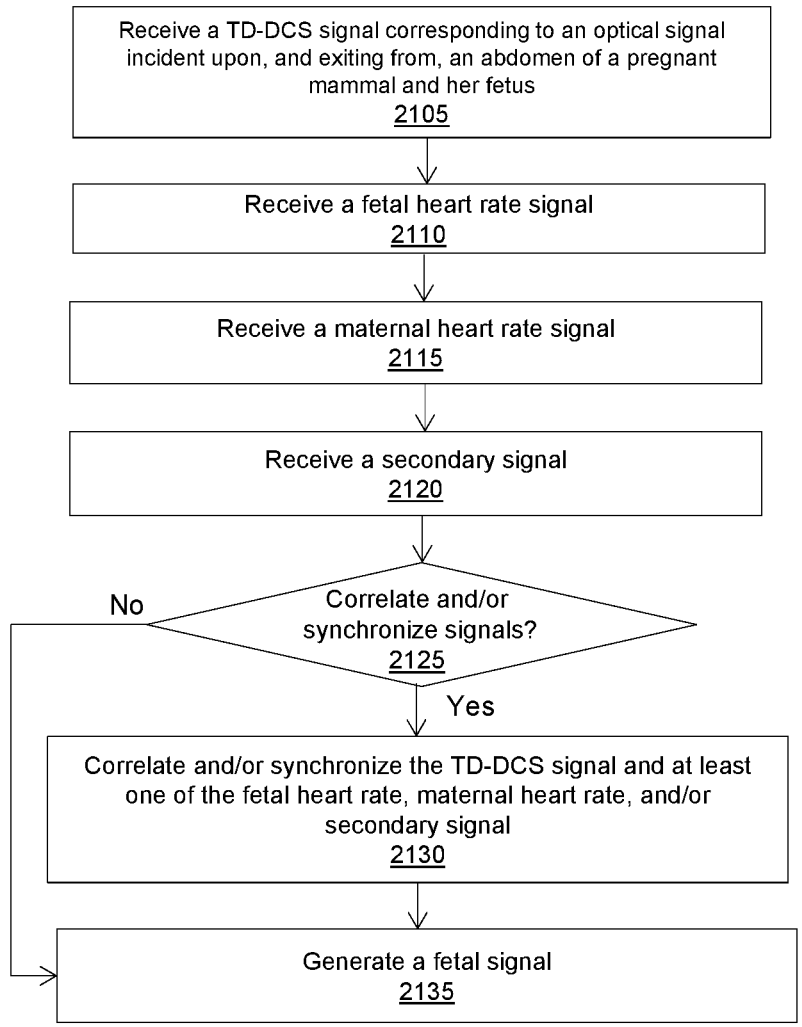
FIG. 21 is a flowchart illustrating an exemplary process for processing a received time-domain diffuse imaging correlation spectroscopy (TD-DCS) signal to generate a fetal signal, consistent with some embodiments of the present invention.

FIG. 21 is a flowchart illustrating a process 2100 for processing a received TD-DCS signal to generate a fetal signal. Process 2100 may be performed by, for example, system 100 and/or components thereof. When a TD system is used, system 100 may be configured to perform DCS by causing one or more light sources 105 to emit brief (e.g., 10-50 ps) light pulses that may be sinusoidally modulated with a frequency between, for example, 100 and 1000 MHz. These light pulses may be projected into the pregnant mammal's abdomen at a repetition rate of, for example, 1-50 MHz. These pulses may yield photon-density waves inside the imaged tissue. From there, amplitude differences and phase shifts between the incident light and detected light may be determined as a function of time. Emitted photons (e.g., back reflected or transmitted) may then be either collected by an optical fiber and guided to a detector (e.g., photomultiplier) or directly detected by the detector, which may be a microchannel plate photomultiplier (MCP-PMT). The MCP-PMT signals may then be amplified and/or attenuated and input into a constant fraction discriminator (CFD), the output of which may be provided to a time-to-amplitude converter (TAC). Output of the TAC may be counted as discrete events by a pulse-height analyzer (PHA) and accumulated until a peak count is reached (e.g., 100,000 counts, 1,000,000 counts, etc.). This information may be used to generate a time-response curve that is used to generate an image of the pregnant mammal's abdomen and/or determine a fetal hemoglobin oxygen saturation.

In some instances, system 100 may include a light source 105 that is, for example, a long-coherence-length (>5 m) laser operating in the NIR to deliver light to the tissue; detector 160 may be a single photon counting avalanche photodiode (SPAD) detector that outputs an electronic pulse for every photon received. System 100 may also include a photon correlator (that may be a stand-alone device and/or included in computer 150) that keeps track of the arrival times of all photons detected by the APDs and derives an intensity correlation function from the temporal separations of all pairs of photons (see FIG. 1). The correlator may be a piece of hardware and/or software configured to perform computation of temporal correlation functions.

Initially, a TD-DCS signal that corresponds to an optical signal incident upon, and exiting from the abdomen of a pregnant mammal and a fetus contained therein, may be received (step 2105) by, for example, a computer or processor such as computer 150. The detected electronic signal may be communicated directly, or indirectly, to the computer by/from a detector like detector 160.

In step 2110, a fetal heart rate signal may be received from, for example, Doppler/ultra sound probe 135. In step 2115, a maternal heart rate signal may be received from, for example, pulse oximetry probe 130, NIRS adult hemoglobin probe 125, and/or a blood pressure sensing device. Optionally, a secondary signal may be received in step 2120. Exemplary secondary signals include, but are not limited to, a respiratory signal for the pregnant mammal, an indication of whether meconium has been detected in the amniotic fluid of the pregnant mammal, a signal indicating uterine tone, a signal indicating a hemoglobin oxygen saturation level of the pregnant mammal, a pulse oximetry signal of the pregnant mammal, and combinations thereof.

In step 2125 it may be determined whether to correlate and/or synchronize the fetal heart rate signal, maternal heart rate signal, and/or secondary signal. If so, a synchronization and/or correlation process may be performed (step 2130). At times, execution of step 2130 may include synchronization of the signals in the time domain and/or correlation of one or more scales of measurement by which the signals are recorded. In some cases, this synchronization may be similar to the correlation and/or synchronization of step 425. In some instances, synchronization of the plurality of fetal signals may be performed using timestamps present within the first and second detected electronic signals. These timestamps may be generated by, for example, timestamping device 185. When the signals are not to be synchronized and/or correlated, process 2100 may proceed to step 2135.

In step 2135, a fetal signal may be generated using two or more of the received signals, at least one of which is the detected electronic signal. In many instances, execution of step 2135 involves using the fetal heart rate signal, maternal heart rate signal, and/or one or more secondary signals to isolate, or otherwise extract, a portion of the received detected electronic signal such as the portion of the signal contributed by the fetus. Execution of step 2135 may be similar to the isolation of a fetal signal described herein with regard to process 400, 500, 600, 700, 1000, 1200, 1300, 1600, 1700, 1900. In some embodiments, execution of steps 2130 and/or 2135 may include execution of one or more procedures to, for example, reduce the signal-to-noise ratio or amplify the signal including, but not limited to, application of filters, subtraction of a known noise component, multiplication of two signals, normalization, and the like. In some instances, execution of step 2135 may include processing the detected electronic signal with a lock-in amplifier to amplify a preferred portion of the signal and/or reduce noise in the signal. The preferred portion of the signal may, in some instances, correspond to known quantities (e.g., wavelength or frequency) of the light incident on the pregnant mammal's abdomen.

Figure 22:
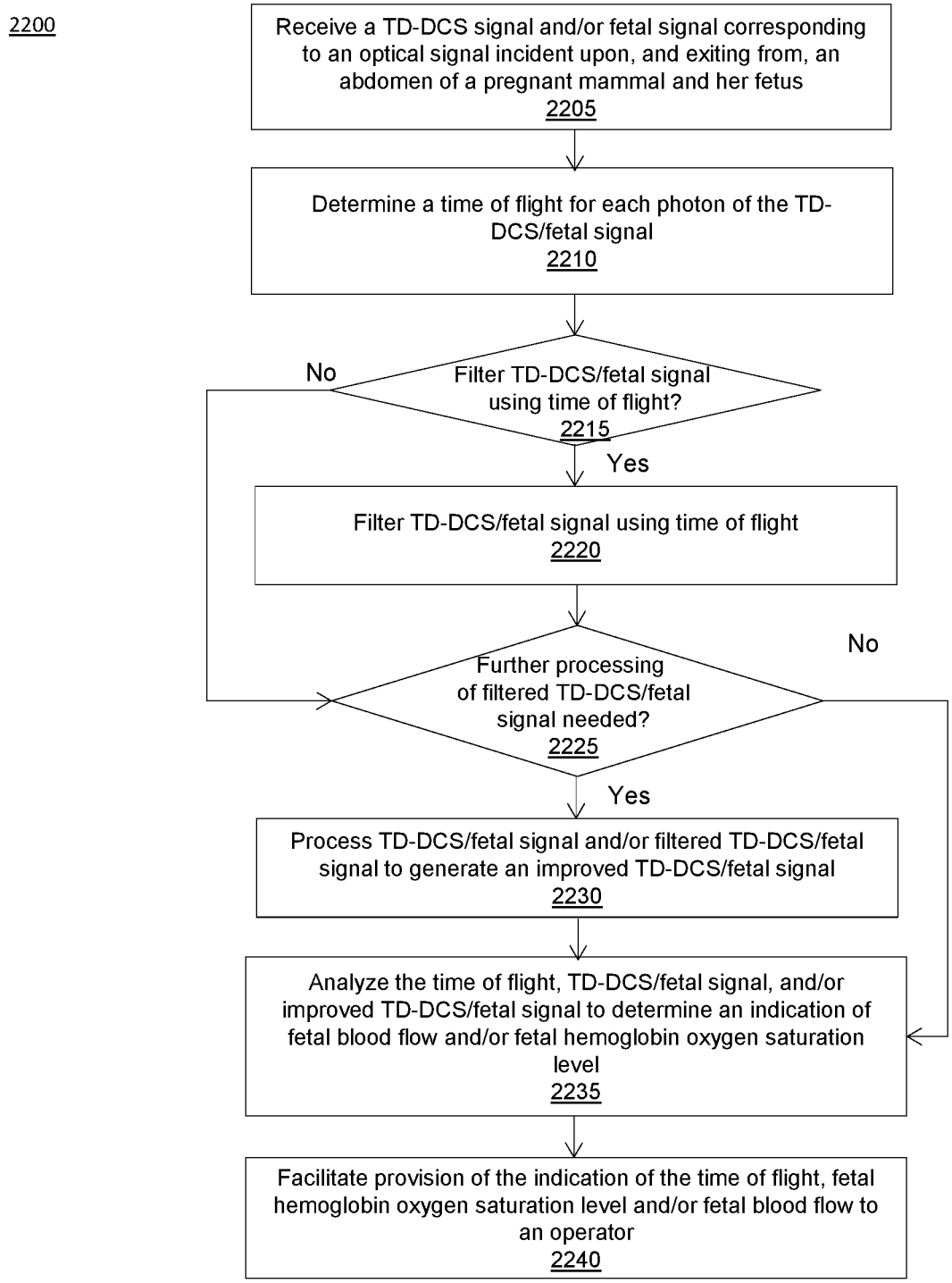
FIG. 22 is a flowchart illustrating an exemplary process for determining an indication of fetal blood flow and/or a fetal hemoglobin oxygen saturation level, consistent with some embodiments of the present invention.

FIG. 22 provides a flowchart of a process 2200 for using TD-DCS and/or fetal signals to determine an indication of fetal blood flow and/or fetal hemoglobin oxygen saturation. Process 2200 may be performed by, for example, system 100 and/or components therein.

In step 2205, a TD-DCS and/or a fetal signal corresponding to an optical signal incident upon and exiting from a pregnant mammal's abdomen and her fetus may be received. The fetal signal may be a TD-DCS signal and may be generated via execution of one or more of processes process 400, 500, 600, 700, 1000, 1200, 1300, 1600, 1700, 1900, and/or 2100. At times, the TD-DCS signal received in step 2205 may be pre-processed to, for example, remove noise and/or isolate a portion of the TD-DCS signal that corresponds to light incident on the fetus by, for example, removing one or more confounding effects of the pregnant mammal from the TD-DCS signal.

In step 2210, a time of flight for each counted photon of the TD-DCS/fetal signal may be determined. In some embodiments, a time of flight (TOF) may be measured as the difference between a time of emission and the time of detection. In other embodiments, a time of flight may be a relativistic determination (e.g., relatively short or long time of flight). In some instances, the absolute and/or relative time of flight may be determined via application of time-gated strategies to the TD-DCS/fetal signal and/or mathematical analysis of the TD-DCS/fetal signal via, for example, DCS autocorrelation functions. With the time of flight information, it is possible to differentiate between short and long photon paths through the pregnant mammal's and/or fetal tissue which may then be used to determine, for example, a blood flow index and/or a hemoglobin saturation level for different depths and/or layers of pregnant mammal/fetal tissue. the time of flight for photons may be used.

In some embodiments, the TD-DCS/fetal signal may be achieved via time-correlated single-photon counting (TCSPC), which may be used to time-tag each detected photon with two values, a TOF from the source to the detector to obtain the TPSF and the absolute arrival time. The absolute arrival time may be used to calculate a temporal autocorrelation function for DCS. In these embodiments, step 2210 may be performed by analyzing the correlation functions over different times, or gates, of the temporal point-spread function (TPSF), which may enable differentiation between short and long times of flight for a plurality of photons. This may then be used to evaluate characteristics (e.g., rate of blood flow, hemoglobin saturation, etc.) of different depths of tissue. In some instances, TPSF information may also be used to determine scattering and/or absorption coefficients for different layers of tissue in the pregnant mammal's abdomen. At times the evaluation of characteristics of different depths and/or layers of tissue may incorporate information obtained using single and/or double separation analysis as explained above with regard to processes 1100 and 1200 of FIGS. 11 and 12, respectively.

In step 2215, it may be determined whether the received TD-DCS/fetal signal is to be filtered using, e.g., a preferred TOF, a preferred range of TOFs, and/or TOF information (e.g., fastest or slowest TOF) for the photons included in the signal. When the received TD-DCS/fetal signal is not to be filtered, process 2200 may proceed to step 2225.

When the determination of step 2215 is affirmative, the received TD-DCS/fetal signal may be filtered using one or more TOF-based criteria. In some instances, the TOF-based filtering criteria used in step 2220 may be a minimum and/or maximum TOF threshold so that only photons with a TOF within a selected range are considered. In some instances, differentiation between short and long TOFs may be facilitated by application of time-gated strategies to the DCS autocorrelation functions.

In general, photons with a longer TOF have penetrated deeper into tissue. If the depths of various layers of maternal tissue are known and/or may be approximated via, for example, data regarding the pregnant mammal's anatomy as may be provided by ultrasound and/or MRI images like images 201 and 202 of FIGS. 2A and 2B, respectively, approximations of tissue location, density, or other optical properties as may be provided by the layers of pregnant mammal tissue discussed above with regard to FIGS. 14A, 14B, 15A, and 15B, short separation analysis techniques like those described above with regard to processes 1600 and 1700, and/or tissue or tissue layer modeling that may be facilitated by, for example, the diffusion equation, then the range of TOFs to be filtered for may be set to TOFs consistent with the depth of the fetus and/or set to exclude photons that have only passed through the pregnant mammal's tissue. In this way, the received TD-DCS/fetal signal may be filtered (step 2220) to remove, for example, photons with a TOF that indicates they passed through the pregnant mammal only. Thus, the remaining part of the TD-DCS/fetal signal may carry information regarding photons incident on the fetus. This remaining part of the TD-DCS/fetal signal may be referred to as the filtered TD-DCS/fetal signal.

In some instances, the filtering of step 2220 may be based upon an understanding that light passing through upper layers of tissue will have a shorter TOF than light passing through deeper layers of tissue. The difference in TOF may be caused by the motion of red blood cells within the tissue, which may cause flow-dependent fluctuations in the detected intensity (i.e., number of photons) detected. This allows for separation of photons with a TOF consistent with traveling deep enough into the pregnant mammal's abdomen to be incident upon the fetus and affected by the fetal blood flow from the overall TD-DCS and/or fetal signal.

In step 2225, it may be determined whether further processing of the TD-DCS/fetal signal and/or improved TD-DCS/fetal signal may be desired and/or necessary. This determination may be based on, for example, a signal-to-noise ratio, a clarity of the fetal signal, and/or a strength or intensity of the fetal signal. When further processing of the filtered and/or TD-DCS/fetal signal is not desired and/or necessary, process 2200 may proceed to step 2235. Otherwise, in step 2230, the TD-DCS and/or fetal signal may be further processed to generate an improved fetal signal. The processing of step 2230 may include, but is not limited to, filtering, amplification, and so on. Examples of types of further processing for the signal received in step 2230 are provided above with regard to processes process 400, 500, 600, 700, 1000, 1200, 1300, 1600, 1700, 1900, 2000, 2100 discussed herein with regard to FIGS. 4, 5, 6, 7, 10, 12, 13, 16, 17, 19, 20, and 21, respectively.

Next, the TOF, TD-DCS/fetal signal, and/or improved TD-DCS/fetal signal may be analyzed to determine an indication of fetal blood flow and/or fetal hemoglobin oxygen saturation level (step 2235) using any appropriate method, including, but not limited to, the Beer-Lambert law. In step 2240, provision of the indication to a user (e.g., clinician, physician, nurse, etc.) may be facilitated via, for example, display as a GUI or other indicator on display device 155. In some embodiments, the received TD-DCS/fetal may include an indication of a speckle pattern, and/or a change in a speckle pattern, caused by red blood cells moving through fetal tissue. At times, execution of process 2200 includes quantifying speckle variations and measuring the temporal intensity autocorrelation curve of a single speckle. The decay of this autocorrelation curve over time may be input into a version of the diffusion equation adapted for process 2200 and/or portions thereof to yield an index of blood flow (BFi).

In some embodiments, determination of a fetal hemoglobin oxygen saturation level (i.e., execution of steps 440, 1030, 1325, 1635, 1740, 1825, 1930, 1955, and/or 2235) and/or presentation of same to the user (i.e., execution of steps 445, 1035, 1330, 1640, 1745, 1830, 1960, and/or 2240) may include calculating a running average of fetal blood flow and/or fetal hemoglobin oxygen saturation levels and/or a time weighted average (TWA) of fetal blood flow and/or fetal hemoglobin oxygen saturation levels over one or more time periods (e.g., 5, 10, 15, 30, 60, etc. minutes) so that a clinician may observe average values of fetal blood flow and/or fetal hemoglobin oxygen saturation and determine how they may have changed over time and/or how long a fetus has had a particular blood flow and/or hemoglobin oxygen saturation level. In this way, a clinician may be able to determine whether, or when, the fetus may be at risk of significant metabolic acidosis. A TWA may be calculated via Equation 16:

$$TWA = t_1 l_1 + t_2 l_2 + \ldots t_n l_n / t_1 + t_2 + \ldots t_n \qquad \text{Equation 16}$$

Where:
t=duration; and
l=fetal hemoglobin oxygen saturation level.

For example, if the duration under study were 15 minutes and a fetus had a fetal hemoglobin oxygen saturation level of 70 for 7 minutes, 61 for 5 minutes, and 55 for 3 minutes, the TWA for this time period according to Equation 1 would be:

$$TWA \text{ for } 15 \text{ minutes} = [(7*70) + (5*61) + 3*55)] / (7+5+3) = 64$$

One or more indicators (e.g., mild, moderate, severe, etc.) and/or inflection point(s) of metabolic acidosis may be provided to the clinician along with the fetal blood flow and/or hemoglobin oxygen saturation level and/or average of fetal blood flow and/or hemoglobin oxygen saturation levels. These indicators/inflection points may be based on, for example, information gathered during previously conducted fetal metabolic experimentation and/or clinical studies/trials. In some embodiments, the indicator(s)/inflection point(s) may be provided to the clinician via, for example, a graph of fetal blood flow/hemoglobin oxygen saturation level and/or an average of fetal blood flow/hemoglobin oxygen saturation levels that shows one or more indicators or inflection points thereon or a change in a manner (e.g., color, font, etc.) of how the fetal blood flow/hemoglobin oxygen saturation level and/or an average of fetal blood flow/hemoglobin oxygen saturation levels are displayed to the clinician. Additionally, or alternatively, an alarm or other indicator may be provided to a clinician when it is determined that the fetal blood flow and/or hemoglobin oxygen saturation level is below a critical threshold, or is below a critical TWA for a critical duration, which may represent inflection points for metabolic acidosis and/or indicate significant metabolic acidosis may be occurring.

Additionally, or alternatively, execution of step 2235 and/or 2240 may include concurrent provision of fetal heart rate along with a time weighted average of fetal hemoglobin oxygen saturation levels via, for example, plotting both values on one or more graphs so that they may be visually displayed at the same time. Additionally, or alternatively, a TWA of fetal blood flow and/or hemoglobin oxygen saturation levels may be combined with a TWA of fetal heart rate by, for example, concurrently providing them for display via a graph or table.

The systems, methods, devices, and apparatus described herein may be used to assess fetal tissue and/or hemoglobin oxygenation during pregnancy for many different indications including, but not limited to, monitoring fetal health during labor and deliver, monitoring fetal health prior to the onset of labor, monitoring fetal health during an in-utero fetal procedure, and/or monitoring fetal health during administration of a medical treatment (e.g., surgery, medication, etc.) to the pregnant mammal.

We claim:

1. A method comprising:
    receiving, by a processor, a plurality of detected electronic signals from a detector communicatively coupled to the processor, the plurality of detected electronic signals corresponding to light emitted from a pregnant mammal's abdomen and a fetus contained therein that has been detected by the detector and converted into the detected electronic signal, the emitted light being a portion of light projected, by a light source, into the pregnant mammal's abdomen and fetus contained therein;
    receiving, by the processor, an indication of a depth of the fetus within the pregnant mammal's abdomen;
    isolating, by the processor, a portion of the detected electronic signals that correspond to light that was incident upon the fetus responsively to the indication of the depth of the fetus;
    determining, by the processor, a fetal tissue oxygen saturation level using the isolated portion of the detected electronic signals that correspond to light that was incident upon the fetus; and
    facilitating, by the processor, provision of the fetal tissue oxygen saturation level to a user.

2. The method of claim 1, further comprising:
    generating, by the processor, an image of the fetus, or a portion thereof, using the portion of the detected electronic signals that correspond to light that was incident upon the fetus.

3. The method of claim 2, wherein the image indicates regional variations of fetal tissue oxygen saturation level.

4. The method of claim 1, wherein the determining of the portion of the detected electronic signals that correspond to light that was incident upon the fetus further comprises:
    receiving, by the processor, a secondary signal; and
    analyzing, by the processor, the received plurality of detected electronic signals using the secondary signal to isolate the portion of the processed portion of the received plurality of detected electronic signals corresponding to light that was incident upon the fetus.

5. The method of claim 1, wherein the determining of the portion of the detected electronic signals that correspond to light that was incident upon the fetus further comprises:
    receiving, by the processor, a heartrate signal for the pregnant mammal; and
    analyzing, by the processor, the received plurality of detected electronic signals using the heartrate signal for the pregnant mammal to isolate the portion of the plurality of detected electronic signals corresponding to light that was incident upon the fetus.

6. The method of claim 1, wherein the determining of the portion of the detected electronic signals that correspond to light that was incident upon the fetus further comprises:
    receiving, by the processor, a respiratory signal for the pregnant mammal; and
    analyzing, by the processor, the received plurality of detected electronic signals using the respiratory signal for the pregnant mammal to isolate the portion of the plurality of detected electronic signals corresponding to light that was incident upon the fetus.

7. The method of claim 1, wherein the determining of the portion of the detected electronic signals that correspond to light that was incident upon the fetus further comprises:
    receiving, by the processor, a heartrate signal for the fetus; and
    analyzing, by the processor, the received plurality of detected electronic signals using the heartrate signal for the fetus to isolate the portion of the plurality of detected electronic signals corresponding to light that was incident upon the fetus.

8. The method of claim 1, wherein the determining of the portion of the detected electronic signals that correspond to light that was incident upon the fetus further comprises:
    receiving, by the processor, a short separation signal, the short separation signal corresponding to light that is only incident upon the abdomen of the pregnant mammal; and
    analyzing, by the processor, the received plurality of detected electronic signals using the short separation signal to remove portions of the detected electronic signals that correspond to the short separation signal.

9. The method of claim 1, wherein the plurality of detected electronic signals are received from a plurality of detectors.

10. The method of claim 1, wherein the received plurality of detected electronic signals are synchronized in a time domain.

11. A system comprising:
    a detector configured to receive a plurality of optical signals and convert the plurality of optical signals into a respective plurality of detected electronic signals and communicate the plurality of detected electronic signals to a processor, the plurality of optical signals corresponding to light emitted from a pregnant mammal's abdomen and a fetus contained therein the emitted light being a portion of light projected, by a light source, into the pregnant mammal's abdomen and fetus contained therein;

a processor communicatively coupled to the detector and a memory; and the memory, the memory having a set of instructions stored therein which when executed by the processor cause the processor to:
- receive an indication of a depth of the fetus within the pregnant mammal's abdomen;
- isolate a portion of the detected electronic signals that correspond to light that was incident upon the fetus responsively to the indication of the depth of the fetus;
- determine a fetal tissue oxygen saturation level using the isolated portion of the detected electronic signals that correspond to light that was incident upon the fetus; and
- facilitate provision of the fetal tissue oxygen saturation level to a user.

12. The system of claim 11, wherein the set of instructions further cause the processor to:
- generate an image of the fetus, or a portion thereof, using the portion of the detected electronic signals that correspond to light that was incident upon the fetus.

13. The system of claim 12, wherein the image indicates regional variations of fetal tissue oxygen saturation level.

14. The system of claim 11, wherein the set of instructions further cause the processor to determine the portion of the detected electronic signals that correspond to light that was incident upon the fetus further causing the processor to:
- receive a secondary signal; and
- analyze the received plurality of detected electronic signals using the secondary signal to isolate the portion of the processed portion of the received plurality of detected electronic signals corresponding to light that was incident upon the fetus.

15. The system of claim 11, wherein the set of instructions further cause the processor to determine the portion of the detected electronic signals that correspond to light that was incident upon the fetus further causing the processor to:
- receive a heartrate signal for the pregnant mammal; and
- analyze the received plurality of detected electronic signals using the heartrate signal for the pregnant mammal to isolate the portion of the plurality of detected electronic signals corresponding to light that was incident upon the fetus.

16. The system of claim 11, wherein the set of instructions further cause the processor to determine the portion of the detected electronic signals that correspond to light that was incident upon the fetus further causing the processor to:
- receive a respiratory signal for the pregnant mammal; and
- analyze the received plurality of detected electronic signals using the respiratory signal for the pregnant mammal to isolate the portion of the plurality of detected electronic signals corresponding to light that was incident upon the fetus.

17. The system of claim 11, wherein the set of instructions further cause the processor to determine the portion of the detected electronic signals that correspond to light that was incident upon the fetus further causing the processor to:
- receive a heartrate signal for the fetus; and
- analyze the received plurality of detected electronic signals using the heartrate signal for the fetus to isolate the portion of the plurality of detected electronic signals corresponding to light that was incident upon the fetus.

18. The system of claim 11, wherein the set of instructions further cause the processor to determine the portion of the detected electronic signals that correspond to light that was incident upon the fetus further causing the processor to:
- receive a short separation signal, the short separation signal corresponding to light that is only incident upon the abdomen of the pregnant mammal; and
- analyze the received plurality of detected electronic signals using the short separation signal to remove portions of the detected electronic signals that correspond to the short separation signal.

19. The system of claim 11, wherein the received plurality of detected electronic signals are synchronized in a time domain.

* * * * *